US006861247B1

(12) United States Patent
Miller

(10) Patent No.: US 6,861,247 B1
(45) Date of Patent: Mar. 1, 2005

(54) *SALMONELLA* SECRETED PROTEINS AND USES THEREOF

(75) Inventor: Samuel I. Miller, Seattle, WA (US)

(73) Assignee: The General Hospital Corporation, Boston, MA (US)

(*) Notice: Subject to any disclaimer, the term of this patent is extended or adjusted under 35 U.S.C. 154(b) by 0 days.

(21) Appl. No.: 09/068,804

(22) PCT Filed: Nov. 14, 1996

(86) PCT No.: PCT/US96/18504

§ 371 (c)(1),
(2), (4) Date: Oct. 19, 1998

(87) PCT Pub. No.: WO97/18225

PCT Pub. Date: May 22, 1997

Related U.S. Application Data

(60) Provisional application No. 60/066,733, filed on Nov. 14, 1995.

(51) Int. Cl.$^7$ .............................. C12N 1/20; C12Q 1/68; C12Q 1/18; C07H 21/04; A61K 39/112
(52) U.S. Cl. .............................. 435/252.8; 435/4; 435/6; 435/30; 435/32; 435/38; 435/252.1; 435/243; 536/22.1; 536/23.1; 536/23.7; 424/234.1; 424/258.1
(58) Field of Search .......................... 435/4, 6, 30, 32, 435/38, 252.1, 243, 252.8; 536/22.1, 23.1, 23.7, 184.1; 424/234.1, 258.1

(56) References Cited

U.S. PATENT DOCUMENTS

| 4,603,152 | A |   | 7/1986  | Laurin et al.    |        |
|-----------|---|---|---------|------------------|--------|
| 5,972,899 | A | * | 10/1999 | Zychlinsky et al.| 514/44 |

FOREIGN PATENT DOCUMENTS

| WO | WO 90/11687 |   | 10/1990 |           |
|----|-------------|---|---------|-----------|
| WO | WO 92/17785 |   | 10/1992 |           |
| WO | WO 95/02048 | * | 1/1995  | C12N/15/00|

OTHER PUBLICATIONS

Boehringer Mannheim Biochemicals (1991 Catalog p. 557).*
Stratagene (1991 Product Catalog, p. 66).*
Gibco BRL (Catalogue & Reference Guide 1992, p. 292).*
Promega (1993/1994 Catalog, pp. 90–91).*
New England BioLabs (Catalog 1986/1987, pp. 60–62).*
Collazo et al 1995, Molecular Microbiology, 15(1), 25–38.*
Harris et al. J. of he Am Society of Nephrology 6:1125–33, 1995.*
Anh et al. Nature Genetics 3(4): 283–91, 1993.*
Cawthon et al. Genomics 9(3): 446–60, 1991.*
Hermant et al. "Functional conservation of the Salmonella and Shigella effectors of entry into epithelial cells" *Molecular Microbiology* 17,4:781–789 (1995).
Kangia et al. "Homologs of the Shigell IpaB and IpaC Invasins Are Require for *Salmonella typhimurium* Entry into Cultured Epithelial Cells" *Journal of Bateriology* 117,14:3965–3971 (1995).
Pegues et al. "PhoP/PhoQ transcriptional repression of *Salmonella typhimurium* invasion gene: evidence for a role in protein secretion" *Molecular Microbiology* 17,1:169–181 (1995).
EMBL Accession No. U25631, Sep. 6, 1995, Kaniga et al.
EMBL Acession No. x82670, Oct. 4, 1995, Hermant et al.
Allaoui et al., "MxiD, an outer membrane protein necessary for the secretion of the *Shigella flexneri* Ipa invasins" Molecular Microbiology 7:59–68 (1993).
Allaoui et al., MxiJ, a Lipoprotein Involved in Secretion of Shigella Ipa Invasins, Is Homolgous to YscJ, a Secretion Factor of the Yersinia Yop Proteins Journal of Bacteriology, 174:7661–7669 (1992).
Andrews et al., "Two Novel Virulence Loci, mxiA an mxiB, in *Shigella flexneri* 2a Facilitate Excretion of Invasion Plasmid Antigens" Infection and Immunity, 59:1997–2005 (1991).
Andrews et al., "mxiA of *Shigella flexneri* 2a, Which Facilitates Export of Invasion Plasmid Antigens, Encodes a Homolog of the Low–Calcium–Response Protein, LcrD, of *Yersinia pestis*" Infect. & Immun., 60:3287–3295 (92).
Babinet et al., "Specific Expression of Hepatitis B Surface Antigen (HBsAg) in Transgenic Mice" Science, 230:1160–1163 (1985).
Baudry et al., "Localization of Plasmid Loci Necessary for the Entry of *Shigella flexneri* into HeLa Cells, and Characterization of One Locus Encoding Four Immunogenic Polypeptides" Journal Gen. Microbiology 133: 3403–3413 (1987).
Behlau et al., "A PhoP–Repressed Gene Promotes *Salmonella typhimurium* Invasion of Epithelial Cell" J. Bacteriol. 175:4475–4484 (1993).
Collazo et al., "Functional analysis of the *Salmonella typhimurium* invasion gene invL and invJ and identication of a target of the protein secretion apparatus encoded in the inv Locus" Mol. Micro. 15:25–38,(1995).
Feng et al., "Progressive Sequence Alignment as a Prerequisite to Correct Phylogenetic Trees" J. Mol. Evol. 25:351–360 (1987).
Groisman et al., Cognate gene clusters govern invasion of host epithelial cells by *Salmonella typhimrium* and *Shigella flexneri*, The Embo Journal, 3779–3787 (1993).

(List continued on next page.)

Primary Examiner—Nita Minnifield
Assistant Examiner—Padma Baskar
(74) Attorney, Agent, or Firm—Fish & Richardson P.C.

(57) ABSTRACT

Substantially pure Salmonella secreted proteins (Ssp), the sercetion of which is dependent upon the expession of PrgH; methods of diagnosing Salmonella infection; and live attenuated vaccine strains in which Ssp secretion is decreased.

52 Claims, 24 Drawing Sheets

OTHER PUBLICATIONS

Hantman et al., "Defective Extracellular Protein Secretion by *Salmonella typhimurium* Mutants Impaired in Induction of Eucaryotic Cell Membrane Ruffling and Macrophinocytosis" American society for Microbiology (May 21–25, 1995) pp. 183–185.

Hermant et al., "Functional conservation of the Salmonella and Shigella effectors of entry into epithelial cells," Molecular Microbiology, 17:781–789, (1995).

Higgins et al., "Fast and sensitive multiple sequence alignments on a microcomputer" Cabios Communications, 5:151–153 (1989).

Hueck et al., "*Salmonella typhimurium* secreted invasion determinants are homologous to Shigella Ipa proteins," Molecular Microbiology, 18:479–490, (1995).

Kaniga et al., "Homologs of the Shigella IpaB and IpaC Invasins Are Required for *Salmonella typhimurium* Entry into Cultured Epithelial Cells", Journal of Bacteriology, 177:3965–3971, (1995).

Menard et al., "The secretion of the *Shigella flexneri* Ipa invasins is activated by epithelial cells and controlled by IpaB an IpaD" The Embo Journal 5293–5302 (1994).

Miller et al., "A two-component regulatory system (phoP phoQ) controls *Salmonella typhimurium* virulence" Proc. Natl. Acad. Sci. USA, 86:5054–5085, (1989).

Miller et al., "Salmonella Vaccines with Mutations in the phoP Virulence Regulon" Res. Microbiol. 141:817–821, (1990).

Miller et al., "Constitutive Expression of the PhoP Regulon Attenuates Salmonella Virulence and Survival within Macrophages" J. Bacteriol., 172:2485–2490, (1990).

Mills et al., "A 40 kb chromosomal fragment encoding *Salmonella typhimurium* invasion genes is absent from the corresonding region of the *Eschericia coli* K–12 chromosome" Molecular Microbiology 15:749–759 (1995).

Paradee et al., "Assay of β–Galactosidase" Journal of Bacteriology, 174:352–355 Experiment 48 (1992).

Pegues et al., "PhoP/PhoQ transcriptional repression of *Salmonella typhimurium* invasion genes: evidence for a role in protein secretion" Molecular Microbiology, 17:169–181 (1995).

Pulkkinen et al., "A *Salmonella typhimurium* Virulence Protein Is Similar to a *Yersinia enterocolitica* Invasion Protein and a Bacteriophage Lambda Outer Membrane Protein"Journal of Bacteriology, 173:86–93 (1991).

Sasakawa et al., "Functional organization and nucleotide sequence of virulence Region–2 on the large virulence plasmid in *Shigella flexneri 2a*" Molecular Microbiology 3:1191–1201 (1989).

Sory et al., "Translocation of a hybrid YopE–adenylate cyclase from *Yersinia enterocolitica* into HeLa cells" Molecular Microbiology, 14:583–594 (1994).

Venkatesan et al., "Characterization of invasion plasmid antigen genes (ipaBDC) from *Shigella flexneri*" Proc. Natl. Acad. Sci. 85:9317–9321 (1988).

Supplementary European Search Report (EP 92 90 4089).

* cited by examiner

```
            * **       +* **  ** *  **  ** *****+*  +* +
PrgI   1  ..MATPWSGY........LDDVSAKFDTGVDNLQTQVTEALDKLAAKPSDP   41
MxiH   1  MSVTVPNDDWT.......LSSLSETFDDGTQTLQGELTLALDKLAKNPSNP   44
YscF   1  ...MSNFSGFTKGNDIADLDAVAQTLKKPADDANKAVNDSIAALKDTPDNP   48

*+++ *+****** ***+**+**+** ++ ***+*+*+*
PrgI  42  ALLAAYQSKLSEYNLYRNAQSNTVKVFKDIDAAIIQNFR   80  SEQ ID NO:32:
MxiH  45  QLLAEYQSKLSEYTLYRNAQSNTVKVIKDVDAAIIQNFR   83  SEQ ID NO:33:
YscF  49  ALLADLQHSINKWSVIYNISSTIVRSMKDLMQGILQKFP   87  SEQ ID NO:34:
```

FIG. 4A

```
           + + ++  +  +   ++ +++ +          +       +
PrgJ   1  MSIATIVPENAV.IGQAVNIRSMETDIVSLDDRLLQAFSGSAIATAVDKQT   50
MxiI   1  ..MNYIYPVNQVDIIKASDFQSQE..ISSLEDVVSAKYSDIKMDTDIQVSQ   47

+     +     + ++   +  + +    ++    ++ ++ + ++++++ +        SEQ ID
PrgJ  51  ITNRIEDPNLVTDPKELAISQEMISDYNLYVSMVSTLTRKGVGAVETLLRS  101  NO:35
MxiI  48  IMEMVSNPESL.NPESLAKLQTTLSNYSIGVSLAGTLARKTVSAVETLLKS   97  SEQ ID
                                                                    NO:36
```

FIG. 4B

```
          ***  * *   +****+ ++*  *+ ** + **++ ****+ *** + +
PrgK   1  .MIRRYLYTFLLVMTLAGCKDK.DLLKGLDQEQANEVIAVLQMHNIEANKI   49
MxiJ   1  .MIRYKGFILFLLLMLIGCEQREELISNLSQRQANEIISVLERHNITARKV   50
YscJ   1  MKVKTSLSTLILILFLTGCK..VDLYTGISQKEGNEMLALLRQEGLSADKE   49

* ** * *   + * **   +*   * + *+    ** * **++  +*+*+*+*
PrgK  50  DSGKLGYSITVAEPDFTAAVYWIKTYQLPPRPRVEIAQMFPADSLVSSPR    99
MxiJ  51  DGGKQGISVQVEKGTFASAVDLMRMYDLPNPERVDISQMFPTDSLVSSPR   100
YscJ  50  PDKDGKIKLLVEESDVAQAIDILKRKGYPHESFSTLQDVFPKDGLISSPI    99

*+*+++++*+*+*****+    ++*+****+  ***    * *   ** * +
PrgK 100  AEKARLYSAIEQRLEQSLQTMEGVLSARVHISYDIDAGENGRPPKPVHLS   149
MxiJ 101  AEKARLYSAIEQRLEQSLVSIGGVISAKIHVSYDLE..EKNISSKPMHIS   148
YscJ 100  EELARLNYAKAQEISRTLSEIDGVLVARVHVVLPEEQNNKGKKGVAASAS   149

* *        ** +******* ** +**+++ +           *    *
PrgK 150  ALAVYERGSPLAHQISDIKRFLKNSFADVDYDNISVVL....SERSDAQL   195
MxiJ 149  VIAIYDSPKESELLVSNIKRFLKNTFSDVKYENISVIL....TPKEEYVY   195
YscJ 150  VFIKHAADIQFDTYIPQIKQLVNNSIEGLAYDRISVILPSVDVRQSSHL   199

*  **      *  * +* ****  +*  *            +     +
PrgK 196  Q..APGTPVKRNSFATSWIVLIILLSVMSAGFGVWYYKNHYARNKKGITA   243  SEQ ID
MxiJ 196  TNVQPVKEVKSEFLTNEVIYLFLGMAVLVVILLVWAFKTGWFKRNKI     242  NO:37
YscJ 200  P..RNTSILSIQVSEESKGRLIGLLSLLILLLPVTNLAQYFWLQRKK    244  SEQ ID
                                                                      NO:38
PrgK 243  DDKAKSSNE   252   SEQ ID NO:39
```

```
SspB       RKAEETNRIMGCIGKVLGALLTIVSVVAAVFTGGASLALAAVGLAVMVADEIVKAATGVSFIQQALNPIMEHVLKPLMELIGKAITRALEGLGVDKKTAE
           |||||  || ||| ||  ||||||||||  |    |  ||||||||||||| ||||| ||||||||||| | ||||| ||||| |||  |||||  |
IpaB  298  RKAEELNRVMGCVGKILGALLTIVSVVAAFSGGASLALAAVGIALMVTDAIVQAATGNSFMEQALNPIMKAVIEPLIKLLSDAFTKMLEGLGVDSKKAK

SspB       MAGSIVGAIVAAIAMVAVIVVVAVVGKGAAAKIGNALSKMMGETIKKLVPNVLKQLAQNGSKLFTQGHQRITSGLGNVGSKMGLQTNALSKELVGNTLNK
           |  ||||||   | |||||  |||||||| |||||||||    ||   |  |||||||| ||| | | ||||||| ||| ||| || ||||| |  |
IpaB  398  MIGSILGAIAGALVLVAAVLVLVATVGKQAAAKLAENIGKIIGKTLTDLIPKFLKNFSSQLDDLITNAVARLNKFLGAAGDEV......ISKQIISTHLNQ

SspB       VALGMEVTNTAAQSAGGVABGVFIKNASEALADFMLARFAMDQIQQMLKQSVEIFGENQKVTAELQKAMSSAVQQNADASRFILRQSRA        SEQ ID NO:40
            |  ||  ||  || | | |||| | ||| |  |   |  | ||| ||| |||| ||| || || |||||||||| |||||||||||
IpaB  492  AVLLGESVNSATQAGGSVASASAVFQNSASTNLADLTLSKYQVEQLSKYISEAIEKFGQLQEVIADLLASMSNSQANRTDVAKAILQQTTA 580   SEQ ID NO:41
```

FIG. 13

```
SspC    1        MLISNVGINPAAYLNNHSVENSSQTASQVSAKDILNSIGI.SSSKVSDLGLSPTLSAPAPGVLTQTPGTITSFLKASIQNTDMNQDLNAL
                 |    |   |  |    |    |   | ||| || |   |  |  |           |      |  |   | |   |   | | |
IpaC    1  MLQKQFCNKLLLDTNKENVMEIQN....TKPTQTLYTDISTKQTQSSSETQKSQNYQQIAAHIPLNVGKNPVLTTLND.DQILKLSEQVQHDSEIARL

SspC   91  ANNVTTKANEVVQTQLREQQAEVGKFFDISGMSSSSAVALLAAANTIMLTLNQADSKLSGKLSLVSFDAAKTTASSMMREGMNALSGSISQSALQIGITGV
           |||  |   |   | |   |  |    | |  ||||||    |     || ||||| ||||||| | | ||||||    |||||||||||   || ||
IpaC   96  TDKKMKDLSEMSHTLTPENT.....LDISSLSSNAVSLIISVAVLLSALRTAETKIGSQLSLIAFDATKSAAENIVRQGLAALSSSITGAVTQVGITGI

SspC  191  GAKLEYKGLQNERGALKHNAAKIDKLTTESHSIKNVLNGQNSVKLGAEGVDSLKSLNMKKTGTDATKNLNDATLKSNAGTSATESLGIKDSNKQISPEIQ
           |||  | |  || || ||    |            |                  |  |||||  |                         ||| |
IpaC  190  GAKKTHSGISDQKGALRKNLATAQSLEKELAGSKLGLNKQIDTNITSPQTNS...........STKFLGKNKLAPD..............NISLSTEHK

SspC  291  AILSKRLESVESDIRLEQNTMDMTRIDARKMQMTGDLIMKNSVTVGGIAGASGQYAATQERSEQQISQVNNRVASTASDEARESSRKSTSLIQEMLKTME
           |    |       |  | |     |        | |      ||  |  || ||   |    ||||  |   |     |  |    | |||  |
IpaC  264  TSLSSPDISLQDKIDTQRRTYELNTLSAQQKQNIGRATMETSAVAGNISTSGGRYASALEEEEQLISQASSKQAEEASQVSKEASQATNQLIQKLLNIID

SspC  391  SINQSKASALAAIAGNIRA 409 SEQ ID NO:42
           ||||||  ||| |||||||
IpaC  364  SINQSKNSAASQIAGNIRA 382 SEQ ID NO:43
```

```
SspD    1  MLNIQNYSASPHPGIVAERPQTPSASEHVETAVVPSTTEHRGTDIISLSQAATKIHQAQQTLQ...STPPISEENNDERTLARQQLTSSLNALAKSGVSL
           ||  |                                                     ||     | |||       |
IpaD    1  MNITTLTNSISTSSFSPNNTNGSSTETVNSDIKTTTSSHPVSSLTMLNDTLHNIRTTNQALKKELSQKTLTKTSLEEIALHSSQISMDVNKSAQLLDIL

SspD   98  SAEQ...NENLRSAF.SAPTSALFSASPMAQPRTTISDAEIWDMVSQNISAIGDSYLGVYENVAVYTDFYQAFSDILSKMGGWLLP.GKDGNTVKLDVT
           |  |       |    |   |                    |  |   |   ||                        ||    ||  |  ||| |
IpaD  100  SRNEYPINKDARELLHSAPKEAELDGDQM......ISHRELWAKIANSINDINEQYLKVYEHAVSSYTQMYQDFSAVLSSLAGWISPGGNDGNSVKLQVN

SspD  193  SLKNDLNSLVNKYNQINSNTVLFPAQSGSGVKVATEAEARQWLSELNLPNSCLKSYGSGYVVTVDLTPLQKMVQDIDGIGAPGKDSKLEMDNAKYQAWQS
           |||  |  |        |          |||          |                |||        |||                |||||||
IpaD  194  SLKKALEELKEKYK....DKPLYPANNT.....VSQEQANKWILTELGGTIGKVSQKNGGYVVSINMTPIDNMLKSLDNLGGNG...EVVLDNAKYQAWNA

SspD  293  GFKAQEENMKTTLQTLTQKYSNANSLYDNLVKVLSSTISSSLETAKSFLQG  343   SEQ ID NO:44
           || |||  ||  ||| ||||||| ||||||||||||||||||  |  ||
IpaD  282  GFSAEDETMKNNLQTLVQKYSNANSIFDNLVKVLSSTISSCTDTDKLFLHF  332   SEQ ID NO:45
```

FIG. 14

```
SspA    1  MVTSVRTQPPVIMPGMQTEIKTQATNLAANLSAVRESATATLSGEIKGPQLEDFPALIKQASLD  64   SEQ ID NO:46
```

FIG. 15

SEQ ID NO:1:

```
CGCAAAGCCG AGGAAACGAA CCGCATTATG GGATGTATCG GGAAAGTCCT CGGCGCGCTG    60
CTAACCATTG TCAGCGTTGT GGCCGCTGTT TTTACCGGTG GGGCGAGTCT GGCGCTGGCT   120
GCGGTGGGAC TTGCGGTAAT GGTGGCCGAT GAAATTGTGA AGGCGGCGAC GGGAGTGTCG   180
TTTATTCAGC AGGCGCTAAA CCCGATTATG GAGCATGTGC TGAAGCCGTT AATGGAGCTG   240
ATTGGCAAGG CGATTACCAA AGCGCTGGAA GGATTAGGCG TCGATAAGAA AACGGCAGAG   300
ATGGCCGGCA GCATTGTTGG TGCGATTGTC GCCGCTATTG CCATGGTGGC GGTCATTGTG   360
GTGGTCGCAG TTGTCGGGAA AGGCGCGGCG GCGAAACTGG GTAACGCGCT GAGCAAAATG   420
ATGGGCGAAA CGATTAAGAA GTTGGTGCCT AACGTGCTGA ACAGTTGGC GCAAAACGGC    480
AGCAAACTCT TACCCAGGG GATGCAACGT ATTACTAGCG GTCTGGGTAA TGTGGGTAGC    540
AAGATGGGCC TGCAAACGAA TGCCTTAAGT AAAGAGCTGG TAGGTAATAC CCTAAATAAA   600
GTGGCGTTGG GCATGGAAGT CACGAATACC GCAGCCCAGT CAGCCGGTGG TGTTGCCGAG   660
GGCGTATTTA TTAAAAATGC CAGCGAGGCG CTTGCTGATT TTATGCTCGC CCGTTTTGCC   720
ATGGATCAGA TTCAGCAGTG GCTTAAACAA TCCGTAGAAA TATTTGGTGA AAACCAGAAG   780
GTAACGGCGG AACTGCAAAA AGCCATGTCT TCTGCGGTAC AGCAAAATGC GGATGCTTCG   840
CGTTTTATTC TGCGCCAGAG TCGCGCATAA                                    870
```

FIG. 19

SEQ ID NO:2:

```
ATGTTAATTA GTAATGTGGG AATAAATCCC GCCGCTTATT TAAATAATCA TTCTGTTGAG    60
AATAGTTCAC AGACAGCTTC GCAATCCGTT AGCGCTAAAG ATATTCTGAA TAGTATTGGT   120
ATTAGCAGCA GTAAAGTCAG TGACCTGGGG TTGAGTCCTA CACTGAGCGC GCCTGCGCCA   180
GGGGTATTAA CGCAAACCCC CGGAACGATC ACGTCCTTTT TAAAAGCCAG TATTCAAAAT   240
ACCGACATGA ATCAGGATTT GAATGCTCTG GCAAATAATG TCACGACTAA AGCGAATGAG   300
GTTGTGCAAA CCCAGTTACG CGAGCAGCAG GCAGAAGTCG GAAAGTTTTT TGATATTAGC   360
GGAATGTCTT CCAGTGCCGT TGCGCTGTTG GCTGCCGCGA ATACGTTAAT GCTGACGTTG   420
AACCAGGCTG ATAGCAAACT GTCTGGTAAG TTGTCATTAG TCAGTTTTGA TGCAGCTAAA   480
ACGACGGCAA GCTCCATGAT GCGCGAAGGG ATGAATGCGT TGTCCGGTAG TATTTCCCAG   540
AGCGCGCTTC AGTTGGGGAT CACTGGCGTG GGCGCCAAAC TGGAATATAA GGGGCTGCAG   600
AATGAAAGAG GCGCGCTTAA ACATAATGCC GCGAAGATCG ATAAACTGAC CACTGAAAGC   660
CACAGTATTA AAAACGTGCT GAACGGGCAG AATAGCGTCA ACTCGGTGC TGAAGGCGTC    720
GATTCTCTGA AATCGTTAAA TATGAAGAAA ACCGGTACCG ATGCGACGAA AAATCTTAAT   780
GATGCGACGC TTAAATCTAA TGCCGGAACC AGCGCCACGG AAAGTCTGGG TATTAAAGAC   840
AGTAATAAAC AAATCTCCCC TGAACATGCA GCTATTCTGT CGAAACGTCT TGAGTCTGTC   900
GAATCCGATA TTCGTCTTGA GCAGAATACC ATGGATATGA CCCGAATCGA TGCGCGCAAG   960
ATGCAGATGA CGGGCGATCT GATTATGAAG AACTCGGTCA CGGTCGGTGG TATTGCAGGG  1020
GCGTCCGGGC AGTACGCCGC TACTCAGGAA CGTTCCGAGC AGCAAATTAG CCAGGTGAAT  1080
AACCGGGTTG CCAGCACCGA ATCGGACGAA GCCCGTGAAA GTTCACGTAA ATCGACCAGC  1140
CTGATTCAGG AAATGCTGAA AACAATGGAG AGCATTAACC AGTCGAAAGC ATCCGCACTC  1200
GCTGCTATCG CAGGCAATAT TCGCGCTTAA                                   1230
```

FIG. 20

SEQ ID NO:3:

```
ATGCTTAATA TTCAAAATTA TTCCGCTTCT CCTCATCCGG GGATCGTTGC CGAACGGCCG    60
CAGACTCCCT CGGCGAGCGA GCACGTCGAG ACTGCCGTGG TACCGTCTAC CACAGAACAT   120
CGCGGTACAG ATATCATTTC ATTATCGCAG GCGGCTACTA AAATCCACCA GGCACAGCAG   180
ACGCTGCAGT CAACGCCACC GATCTCTGAA GAGAATAATG ACGAGCGCAC GCTGGCGCGC   240
CAGCAGTTGA CCAGCAGCCT GAATGCGCTG GCGAAGTCCG GCGTGTCATT ATCCGCAGAA   300
CAAAATGAGA ACCTGCGGAG CGCGTTTTCT GCGCCGACGT CGGCCTTATT TAGCGCTTCG   360
CCTATGGCGC AGCCGAGAAC AACCATTTCT GATGCTGAGA TTTGGGATAT GGTTTCCCAA   420
AATATATCGG CGATAGGTGA CAGCTATCTG GGCGTTTATG AAAACGTTGT CGCAGTCTAT   480
ACCGATTTTT ATCAGGCCTT CAGTGATATT CTTTCCAAAA TGGGAGGCTG GTTATTACCA   540
GGTAAGGACG GTAATACCGT TAAGCTAGAT GTTACCTCAC TCAAAAATGA TTTAAACAGT   600
TTAGTCAATA AATATAATCA AATAAACAGT AATACCGTTT TATTTCCAGC GCAGTCAGGC   660
AGCGGCGTTA AGTAGCCAC TGAAGCGGAA GCGAGACAGT GGCTCAGTGA ATTGAATTTA   720
CCGAATAGCT GCCTGAAATC TTATGGATCC GGTTATGTCG TCACCGTTGA TCTGACGCCA   780
TTACAAAAAA TGGTTCAGGA TATTGATGGT TTAGGCGCGC CGGGAAAAGA CTCAAAACTC   840
GAAATGGATA ACGCCAAATA TCAAGCCTGG CAGTCGGGTT TTAAAGCGCA GGAAGAAAAT   900
ATGAAAACCA CATTACAGAC GCTGACGCAA AAATATAGCA ATGCCAATTC ATTGTACGAC   960
AACCTGGTAA AAGTGCTGAG CAGTACGATA AGTAGCAGCC TGGAAACCGC CAAAAGCTTC  1020
CTGCAAGGAT AA                                                      1032
```

FIG. 21

ATGGTTACAA GTGTAAGGAC TCAGCCCCCC GTCATAATGC CAGGTATGCA GACCGAGATC
AAAACGCAGG CCACGAATCT TGCGGCGAAT CTTTCCGCAG TCAGAGAAAG TGCCACAGCG
ACGCTGTCAG GGGAAATTAA AGGCCCGCAA CTGGAAGATT TTCCCGCGCT GATCAAACAG
GCGAGTCTGG ATGC   SEQ ID NO:4

RKAEETNRIMGCIGKVLGALLTIVSVVAAVFTGGASLALAAVGLAVMVADEIVKAATGVS
FIQQALNPIMEHVLKPLMELIGKAITKALEGLGVDRKRQRWPAALLVRLSPLCHGDAVIV
VVAVVGKGAAAKLGNALSKMMGETIKKLVPNVLKQLAQNGSKLFTQGMQRITSGLGNVGS
KMGLQTNALSKELVGNTLNKVALGMEVTNTAAQSAGGVAEGVFIKNASEALADFMLARFA
MDQIQQWLKQSVEIFGENQKVTAELQKAMSSAVQQNADASRFILRQSRAZ   SEQ ID NO:5

FIG. 22

```
MLISNVGINPAAYLNNHSVENSSQTASQSVSAKDILNSIGISSSKVSDLGLSPTLSAPAP
GVLTQTPGTITSFLKASIQNTDMNQDLNALANNVTTKANEVVQTQLREQQAEVGKFFDIS
GMSSSAVALLAAANTLMLTLNQADSKLSGKLSLVSFDAAKTTASSMMREGMNALSGSISQ
SALQLGITGVGAKLEYKGLQNERGALKHNAAKIDKLTTESHSIKNVLNGQNSVKLGAEGV
DSLKSLNMKKTGTDATKNLNDATLKSNAGTSATESLGIKDSNKQISPEHQAILSKRLESV
ESDIRLEQNTMDMTRIDARKMQMTGDLIMKNSVTVGGIAGASGQYAATQERSEQQISQVN
NRVASTASDEARESSRKSTSLIQEMLKTMESINQSKASAL AAIAGNIRAZ
SEQ ID NO:6

MLNIQNYSASPHPGIVAERPQTPSASEHVETAVVPSTTEHRGTDIISLSQAATKIHQAQQ
TLQSTPPISEENNDERTLARQQLTSSLNALAKSGVSLSAEQNENLRSAFSAPTSALFSAS
PMAQPRTTISDAEIWDMVSQNISAIGDSYLGVYENVVAVYTDFYQAFSDILSKMGGWLLP
GKDGNTVKLDVTSLKNDLNSLVNKYNQINSNTVLFPAQSGSGVKVATEAEARQWLSELNL
PNSCLKSYGSGYVVTVDLTPLQKMVQDIDGLGAPGKDSKLEMDNAKYQAWQSGFKAQEEN
MKTTLQTLTQKYSNANSLYDNLVKVLSSTISSSLETAKSFLQGZ
SEQ ID NO:7

MVTSVRTQPPVIMPGMQTEIKTQATNLAANLSAVRESATATLSGEIKGPQLEDFPALIKQ
ASLD
SEQ ID NO:8
```

FIG. 23

```
ATGCATTATTTTTTTATCATCGTAATCTGGTTGCTTAGCATAAATACGGCATGGGCTGAT
TCTGGCTTCAGGCTGAAAAAATGTTCAATATTGAATCCGAACTACTTTACGCTATCGCCCAGCAG
GAATCGGCGATGAAACCTGGCGCCATTGGTCATAACCGAGATGGTTCAACCGATCTTGGCCTGAT
GCAAATTAACAGCTTCCATATGAAAAGGCTGAAAAAAATGGGGATTAGTGAAAAACAGTTGTTAC
AGGACCCCTGCATTTCTGTCATTGTGGGCGACCTCCATTTTATCAGATATGATGAAAATCTACGG
TTATAGCTGGGAGGCCGTTGGCGCTTATAATGCCGGGACGTCGCCGAAACGATCGGATATAAGGA
AACGTTATGCTAAAAAAATTTGGGAGAATTACAGAAAATTAAAAGGAATGTCAGCAGAAGAGAAA
AACAAAAGACTTTCTATCGCGGCAAACAAATAA        (SEQ ID NO:9)

ATCAGCTTGCCGTCGTCATAAGCAACTGGGCTTGCATTGCTTTTAGTTGTACAAACTGTGCAGGC
GTCTTCCAGCATTCTATTGTTCCGTGAATCCGGAAATCTGCACGTACCTGCTCCAGATTACTATG
AGGATTATCCTTAAGTACAAGGGCCGCCGCCATCGTTCCGGTTCTTCCCACTCCGCCCAGACAAT
GAATCATCGGTAAATGCTTATCTGATGAACTACGCCCCGGCGCGCCATTTTGGTTACTATTTTTC
ACCCTATCCGCCAGGTATTCTAACTGATCCGTAGACGGTAACGGCTGGTGATCTGGCCAATTTTT
CACATGCAATACCGGGATTGTATACCGCTTTCCCCGCAGGACAGTTGCATATTGTATTGGTCTAT
CGCTTCTCCCTGACTGGCTGAGCTCTCTTTTTGGCTGTTGGTATGCACCTCGCCAAAGGTGTAGC
TCCCTCTGAAATAGGTGGTAATTGTTTTGCCTGCATCTGATCTTCCGACGTTAACACCACCAGGC
ACGAGCATTCTTTTTCAAGAAGCATTTTCATATGCGCTTCCAGCGCATCCCGGCGATTT
(SEQ ID NO:10)
```

FIG. 24

MHYFFIIVIWLLSINTAWADSGFRLKKCSILNPNYFTLSPSRNRRZNLAPLVITEMVQPI
LAZCKLTASIZKGZKKWGLVKNSCYRTPAFLSLWATSILSDMMKIYGYSWEAVGAYNAGT
SPKRSDIRKRYAKKIWENYRKLKGMSAEEKNKRLSIAANK
                                                    SEQ ID NO:11

WPGTICGQQHSINQQTQVKLSDGMPVPVIRLTFDGKPVALAGIRTQKIRPDRLEAHMKML
LEKECSCLVVLTSERSDAGKTITTYFRGSYTFGEVHTNSQKVSSASQGEAIDQYNMQLSC
GEKRYTIPVLHVKNWPDHQPLPSTDQLEYLADRVKNSNQNGAPGRSSSDKHLPMIHCLGG
VGRTGTMAAALVLKDNPHSNLEQVRADFRIHGTIECWKTPAQFVQLKAMQAQLLMTTAS
                                                    SEQ ID NO:12

FIG. 25

MRDCLNNGNPVLNVGASGLTTLPDRLPPHITTLVIPDNNLTSLPELPEGLRELEVSGNLQ
LTSLPSLPQGLQKLWAYNNWLASLPTLPPGLGDLAVSNNQLTSLPEMPPALRELRVSGNN
LTSLRALPSGLQKLWAYNNRLTSLPEMSPGLQELDVSHNQLTRLPQSLTGLSSAARVYLD
GNPLSVRTRDRLCGHHWPFRHQDTLRYGGAFRPREARALHLAVADWLTSAREGEAAQADR
WQAFGLEDNAAAFSLVLDRLRETENFKKDAGFKAQISSWLTQLAEDAALRAKTFAMATEA
TSTCEDRVTHALHQMNNVQLVHNAEKGEYDNNLQGLVSTGREMFRLATLEQIAREKAGTL
ALVDDVEVYLAFQNKLKESLELTSVTSEMRFFDVSGVTVSDLQAADVQVKTAENSGFSKW
ILQWGPLHSVLERKVPERFNALREKQISDYEDTYRKLYDEVLKSSGLVDDTDAERTIGVS
AMDSAKKEFLDGLRALVDEVLGSYLTARWRLNZ
                                                    SEQ ID NO:14

FIG. 27

```
ATGCGTGATT GCCTGAATAA CGGCAATCCA GTGCTTAACG TGGGAGCGTC AGGTCTTACC
ACCTTACCAG ACCGTTTACC ACCGCATATT ACAACACTGG TTATTCCTGA TAATAATCTG
ACCAGCCTGC CGGAGTTGCC GGAAGGACTA CGGGAGCTGG AGGTCTCTGG TAACCTACAA
CTGACCAGCC TGCCATCGCT GCCGCAGGGA CTACAGAAGC TGTGGGCCTA TAATAATTGG
CTGGCCAGCC TGCCGACGTT GCCGCCAGGA CTAGGGGATC TGGCGGTCTC TAATAACCAG
CTGACCAGCC TGCCGGAGAT GCCGCCAGCA CTACGGGAGC TGAGGGTCTC TGGTAACAAC
CTGACCAGCT GCGCGCGCTG CCGTCAGGAC TACAGAAGCT GTGGGCCTAT AATAATCGGC
TGACCAGCCT GCCGGAGATG TCGCCAGGAC TACAGGAGCT GGATGTCTCT CATAACCAGC
TGACCCGCCT GCCGCAAAGC CTCACGGGTC TGTCTTCAGC GGCACGCGTA TATCTGGACG
GGAATCCACT GTCTGTACGC ACTCGTGACA GGCTCTGCGG ACATCATTGG CCATTCAGGC
ATCAGGATAC ACTTCGATAT GGCGGGGCCT TCCGTCCCCG GAAGCCCGG GCACTGCACC
TGGCGGTCGC TGACTGGCTG ACGTCTGCAC GGGAGGGGGA AGCGGCCCAG GCAGACAGAT
GGCAGGCGTT CGGACTGGAA GATAACGCCG CCGCCTTCAG CCTGGTCCTG GACAGACTGC
GTGAGACGGA AAACTTCAAA AAAGACGCGG GCTTTAAGGC ACAGATATCA TCCTGGCTGA
CACAACTGGC TGAAGATGCT GCGCTGAGAG CAAAAACCTT TGCCATGGCA ACAGAGGCAA
CATCAACCTG CGAGGACCGG GTCACACATG CCCTGCACCA GATGAATAAC GTACAACTGG
TACATAATGC AGAAAAAGGG AATACGACA ACAATCTCCA GGGGCTGGTT TCCACGGGGC
GTGAGATGTT CCGCCTGGCA ACACTGGAAC AGATTGCCCG GGAAAAAGCC GGAACACTGG
CTTTAGTCGA TGACGTTGAG GTCTATCTGG CGTTCCAGAA TAAGCTGAAG GAATCACTTG
AGCTGACCAG CGTGACGTCA GAAATGCGTT TCTTTGACGT TTCCGGCGTG ACGGTTTCAG
ACCTTCAGGC TGCGGACGTT CAGGTGAAAA CCGCTGAAAA CAGCGGGTTC AGTAAATGGA
TACTGCAGTG GGGGCCGTTA CACAGCGTGC TGGAACGCAA AGTGCCGGAA CGCTTTAACG
CGCTTCGTGA AAAGCAAATA TCGGATTATG AAGACACGTA CCGGAAGCTG TATGACGAAG
TGCTGAAATC GTCCGGGCTG GTCGACGATA CCGATGCAGA ACGTACTATC GGAGTAAGTG
CGATGGATAG TGCGAAAAAA GAATTTCTGG ATGGCCTGCG CGCTCTTGTG GATGAGGTGC
TGGGTAGCTA TCTGACAGCC CGGTGGCGTC TTAACTGA
```

SEQ ID NO:13

FIG. 26

```
CGCAAAGCCGAGGAAACGAACCGCATTATGGGATGTATCGGGAAAGTCCTCGGCGCGCTG
CTAACCATTGTCAGCGTTGTGGCCGCTGTTTTTACCGGTGGGGCGAGTCTGGCGCTGGCT
GCGGTGGGACTTGCGGTAATGGTGGCCGATGAAATTGTGAAGGCGGCGACGGGAGTGTCG
TTTATTCAGCAGGCGCTAAACCCGATTATGGAGCATGTGCTGAAGCCGTTAATGGAGCTG
ATTGGCAAGGCGATTACCAAAGCGCTGGAAGGATTAGGCGTCGATAAGAAAACGGCAGAG
ATGGCCGGCAGCATTGTTGGTGCGATTGTCGCCGCTATTGCCATGGTGGCGGTCATTGTG
GTGGTCGCAGTTGTCGGGAAAGGCGCGGCGGCGAAACTGGGTAACGCGCTGAGCAAAATG
ATGGGCGAAACGATTAAGAAGTTGGTGCCTAACGTGCTGAAACAGTTGGCGCAAAACGGC
AGCAAACTCTTTACCCAGGGGATGCAACGTATTACTAGCGGTCTGGGTAATGTGGGTAGC
AAGATGGGCCTGCAAACGAATGCCTTAAGTAAAGAGCTGGTAGGTAATACCCTAAATAAA
GTGGCGTTGGGCATGGAAGTCACGAATACCGCAGCCCAGTCAGCCGGTGGTGTTGCCGAG
GGCGTATTTATTAAAAATGCCAGCGAGGCGCTTGCTGATTTTATGCTCGCCCGTTTTGCC
ATGGATCAGATTCAGCAGTGGCTTAAACAATCCGTAGAAATATTTGGTGAAAACCAGAAG
GTAACGGCGGAACTGCAAAAAGCCATGTCTTCTGCGGTACAGCAAAATGCGGATGCTTCG
CGTTTTATTCTGCGCCAGAGTCGCGCATAAAAACTGCCAAAATAAAGGGAGAAAAATATG
TTAATTAGTAATGTGGGAATAAATCCCGCCGCTTATTTAAATAATCATTCTGTTGAGAAT
AGTTCACAGACAGCTTCGCAATCCGTTAGCGCTAAAGATATTCTGAATAGTATTGGTATT
AGCAGCAGTAAAGTCAGTGACCTGGGGTTGAGTCCTACACTGAGCGCGCCTGCGCCAGGG
GTATTAACGCAAACCCCCGGAACGATCACGTCCTTTTTAAAAGCCAGTATTCAAAATACC
GACATGAATCAGGATTTGAATGCTCTGGCAAATAATGTCACGACTAAAGCGAATGAGGTT
GTGCAAACCCAGTTACGCGAGCAGCAGGCAGAAGTCGGAAAGTTTTTTGATATTAGCGGA
ATGTCTTCCAGTGCCGTTGCGCTGTTGGCTGCCGCGAATACGTTAATGCTGACGTTGAAC
CAGGCTGATAGCAAACTGTCTGGTAAGTTGTCATTAGTCAGTTTTGATGCAGCTAAAACG
ACGGCAAGCTCCATGATGCGCGAAGGGATGAATGCGTTGTCCGGTAGTATTTCCCAGAGC
GCGCTTCAGTTGGGGATCACTGGCGTGGGCGCCAAACTGGAATATAAGGGGCTGCAGAAT
GAAAGAGGCGCGCTTAAACATAATGCCGCGAAGATCGATAAACTGACCACTGAAAGCCAC
AGTATTAAAAACGTGCTGAACGGGCAGAATAGCGTCAAACTCGGTGCTGAAGGCGTCGAT
TCTCTGAAATCGTTAAATATGAAGAAAACCGGTACCGATGCGACGAAAAATCTTAATGAT
GCGACGCTTAAATCTAATGCCGGAACCAGCGCCACGGAAAGTCTGGGTATTAAAGACAGT
AATAAACAAATCTCCCCTGAACATCAGGCTATTCTGTCGAAACGTCTTGAGTCTGTCGAA
TCCGATATTCGTCTTGAGCAGAATACCATGGATATGACCCGAATCGATGCGCGCAAGATG
CAGATGACGGGCGATCTGATTATGAAGAACTCGGTCACGGTCGGTGGTATTGCAGGGGCG
TCCGGGCAGTACGCCGCTACTCAGGAACGTTCCGAGCAGCAAATTAGCCAGGTGAATAAC
CGGGTTGCCAGCACCGCATCGGACGAAGCCCGTGAAAGTTCACGTAAATCGACCAGCCTG
ATTCAGGAAATGCTGAAAACAATGGAGAGCATTAACCAGTCGAAAGCATCCGCACTCGCT
GCTATCGCAGGCAATATTCGCGCTTAATCTGAAAGGTCATCTATACGCCATCATGGGTGT
GATTTAATCGCGCTCCTGATGGCGAACTGGGGATATTATGCTTAATATTCAAAATTATTC
CGCTTCTCCTCATCCGGGGATCGTTGCCGAACGGCCGCAGACTCCCTCGGCGAGCGAGCA
CGTCGAGACTGCCGTGGTACCGTCTACCACAGAACATCGCGGTACAGATATCATTTCATT
ATCGCAGGCGGCTACTAAAATCCACCAGGCACAGCAGACGCTGCAGTCAACGCCACCGAT
CTCTGAAGAGAATAATGACGAGCGCACGCTGGCGCCAGCAGTTGACCAGCAGCCTGAA
TGCGCTGGCGAAGTCCGGCGTGTCATTATCCGCAGAACAAAATGAGAACCTGCGGAGCGC
GTTTTCTGCCGACGTCGGCCTTATTTAGCGCTTCGCCTATGGCGCAGCCGAGAACAAC
CATTTCTGATGCTGAGATTTGGGATATGGTTTCCCAAAATATATCGGCGATAGGTGACAG
CTATCTGGGCGTTTATGAAAACGTTGTCGCAGTCTATACCGATTTTTATCAGGCCTTCAG
TGATATTCTTTCCAAAATGGGAGGCTGGTTATTACCAGGTAAGGACGGTAATACCGTTAA
GCTAGATGTTACCTCACTCAAAAATGATTTAAACAGTTTAGTCAATAAATATAATCAAAT
AAACAGTAATACCGTTTTATTTCCAGCGCAGTCAGGCAGCGGCGTTAAAGTAGCCACTGA
AGCGGAAGCGAGACAGTGGCTCAGTGAATTGAATTTACCGAATAGCTGCCTGAAATCTTA
TGGATCCGGTTATGTCGTCACCGTTGATCTGACGCCATTACAAAAAATGGTTCAGGATAT
TGATGGTTTAGGCGCGCCGGGAAAAGACTCAAAACTCGAAATGGATAACGCCAAATATCA
AGCCTGGCAGTCGGGTTTTAAAGCGCAGGAAGAAAATATGAAAACCACATTACAGACGCT
GACGCAAAAATATAGCAATGCCAATTCATTGTACGACAACCTGGTAAAAGTGCTGAGCAG
TACGATAAGTAGCAGCCTGGAAACCGCCAAAAGCTTCCTGCAAGGATAACAGAAGAGGAT
ATTAATAATGGTTACAAGTGTAAGGACTCAGCCCCCGTCATAATGCCAGGTATGCAGAC
CGAGATCAAAACGCAGGCCACGAATCTTGCGGCGAATCTTTCCGCAGTCAGAGAAAGTGC
CACAGCGACGCTGTCAGGGGAAATTAAAGGCCCGCAACTGGAAGATTTTCCCGCGCTGAT
CAAACAGGCGAGTCTGGATGC
```
SEQ ID NO:15

FIG. 28

```
GAGCTCAGCAACGTGTCGAAAGCCTGTAAAATCATGGGCGTCTCGCGCGATACGTTTTAC
CGTTATCGTGAACTGGCCGATGAAGGCGGCGTTGATGCGCTGATAAATCGTAGTCGCCGC
GTACCTAACCTTAAGAACCGTACCGATGAGGCAACTGAGCAAGCTGTTGTTGATTATGCC
GTTGCGTTCCCGGCCCATGGTCAGCACCGAACTGCGCAAACAGGACGTTTTTATCTCCGG
TAGTGATGTCCATTCCGTCTGGCTGCGCACAACCTTGAGAACTTCAAAAAACGCCTGAAA
GCGCTGGAAGAAAAAGTGGCCCGCGATGGCATTGAACTGACTGCCAGATCGCCGCGCTGG
AGCGTAAAGCCAGTGATGATGAAGCCTGTGGTGAGATTGAAACCGTTCATCCGGGATATC
TGGGGTCACAGGACACGTTCTACGTGGGCAACCTGAAAGGCGTTGGGCGAATCTATCAGC
AGACGTTCGTTGATACATACTCGAAGGTGGCTCACTGCAAGCGCTATATCACCAAAACGC
CGATTACAGCGGCTGATTTGCTGAATGATCGTGTACTGCCGTTTATGAGTCTCAGGGCCT
GCCGATGCTAAGGATACTGACAGACAGGGGTACAGAATATTGCGGCAAAGTGGAACATCA
TGATTATCAGCTTTATCTGGAGATAAATGACATCGAACACACGAAAACGAAGGCGATGTC
CCCGCAGACCAATGGCATCTGCGAGCGGTTCCATAAAACGATACTGAACGAATTTTATCA
GGTGACGTTCCGCAAAAAGTTATATGGCGATTTTGATACATTACAATCGGATCTTGATGA
ATGGCTGGTTCACTATAATAATGAGCGAACCCATCAGGGAAAATGTGCTGTGGCCGGAC
GCCGATGGAAACGTTACTTGATGGAAAACGCATCTGGTCTGAGAAGAATTTAAGCCAGAT
GTAATCTGACAGATACCTGTATAAATAACCGGTAACTGTCAGATCAGGTCTGAGCTAATA
CAACTAATTGTATGTTATTTGTCGTTTATTGCTAAATATATCGTTAATTGAAGGCTTG
ATGCGTGTGTCTGCGTTAATCTCTTTTCATTGTGCTGTAAATTAGGCAGTGGAATATGTT
TAATATCCGCAATACACAACCTTCTGTAAGTATGCAGGCTATTGCTGGTGCAGCGGCACC
AGAGGCATCTCCGGAAGAAATTGTATGGGAAAAATTCAGGTTTTTTCCCGCAGGAAAAT
TACGAAGAAGCGCAACAGTGTCTCGCTGAACTTTGCCATCCGGCCCGGGGAATGTTGCCT
GATCATATCAGCAGCCAGTTTGCGCGTTTAAAAGCGCTTACCTTCCCCGCGTGGGAGGAG
AATATTCAGTGTAACAGGGATGGTATAAATCAGTTTTGTATTCTGGATGCAGGCAGCAAG
GAGATATTGTCAATCACTCTTGATGATGCCGGGAACTATACCGTGAATTGTCAGGGGTAC
AGTGAAGCACATGACTTCATCATGGACACAGAACCGGGAGAGGAATGCACAGAATTCGCG
GAGGGGGCATCCGGGACATCCCTCCGCCCTGCCACAACGGTTTCACAGAAGGCAGCAGAG
TATGATGCTGTCTGGTCAAATGGGAAAGGGATGCACCAGCAGGAGAGTCACCCGGCCGCG
CAGCAGTGGTACAGGAAATGCGTGATTGCCTGAATAACGGCAATCCAGTGCTTAACGTGG
GAGCGTCAGGTCTTACCACCTTACCAGACCGTTTACCACCGCATATTACAACACTGGTTA
TTCCTGATAATAATCTGACCAGCCTGCCGGAGTTGCCGGAAGGACTACGGGAGCTGGAGG
TCTCTGGTAACCTACAACTGACCAGCCTGCCATCGCTGCCGCAGGGACTACAGAAGCTGT
GGGCCTATAATAATTGGCTGGCCAGCCTGCCGACGTTGCCGCCAGGACTAGGGGATCTGG
CGGTCTCTAATAACCAGCTGACCAGCCTGCCGGAGATGCCGCCAGCACTACGGGAGCTGA
GGGTCTCTGGTAACAACCTGACCAGCTGCGCGCGCTGCCGTCAGGACTACAGAAGCTGTG
GGCCTATAATAATCGGCTGACCAGCCTGCCGGAGATGTCGCCAGGACTACAGGAGCTGGA
TGTCTCTCATAACCAGCTGACCCGCCTGCCGCAAAGCCTCACGGGTCTGTCTTCAGCGGC
ACGCGTATATCTGGACGGGAATCCACTGTCTGTACGCACTCGTGACAGGCTCTGCGGACA
TCATTGGCCATTCAGGCATCAGGATACACTTCGATATGGCGGGGCCTTCCGTCCCCGGGA
AGCCCGGGCACTGCACCTGGCGGTCGCTGACTGGCTGACGTCTGCACGGGAGGGGAAGC
GGCCCAGGCAGACAGATGGCAGGCGTTCGGACTGGAAGATAACGCCGCCGCCTTCAGCCT
GGTCCTGGACAGACTGCGTGAGACGGAAAACTTCAAAAAGACGCGGGCTTTAAGGCACA
GATATCATCCTGGCTGACACAACTGGCTGAAGATGCTGCGCTGAGAGCAAAAACCT
TTGCCATGGCAACAGAGGCAACATCAACCTGCGAGGACCGGGTCACACATGCCCTGCACC
AGATGAATAACGTACAACTGGTACATAATGCAGAAAAAGGGGAATACGACAACAATCTCC
AGGGGCTGGTTTCCACGGGGCGTGAGATGTTCCGCCTGGCAACACTGGAACAGATTGCCC
GGGAAAAAGCCGGAACACTGGCTTTAGTCGATGACGTTGAGGTCTATCTGGCGTTCCAGA
ATAAGCTGAAGGAATCACTTGAGCTGACCAGCGTGACGTCAGAAATGCGTTTCTTTGACG
TTTCCGGCGTGACGGTTTCA
GACCTTCAGGCTGCGGACGTTCAGGTGAAAACCGCTGAAAACAGCGGGTTCAGTAAATGG
ATACTGCAGTGGGGGCCGTTACACAGCGTGCTGGAACGCAAAGTGCCGGAACGCTTTAAC
GCGCTTCGTGAAAAGCAAATATCGGATTATGAAGACACGTACCGGAAGCTGTATGACGAA
GTGCTGAAATCGTCCGGGCTGGTCGACGATACCGATGCAGAACGTACTATCGGAGTAAGT
GCGATGGATAGTGCGAAAAAGAATTTCTGGATGGCCTGCGCGCTCTTGTGGATGAGGTG
CTGGGTAGCTATCTGACAGCCCGGTGGCGTCTTAACTGAGCACGATATTCTCCGCACCAG
GCGAATGTGGTGCGGTGAACAAAGATATTCCTTGGACAAACAACATGAGACAGCACTGAT
GATGCACAGGTGAAACAGGGGAGACTTCTTCAGTCAGGGCGTACGCAACTCAACCTTTTC
GACGATACGCGCC/
```

SEQ ID NO:16

SEQUENCE LISTING (1) GENERAL INFORMATION:

(iii) NUMBER OF SEQUENCES: 47

(2) INFORMATION FOR SEQ ID NO:1:

(i) SEQUENCE CHARACTERISTICS:
      (A) LENGTH: 870 base pairs
      (B) TYPE: nucleic acid
      (C) STRANDEDNESS: double
      (D) TOPOLOGY: linear (ii) MOLECULE TYPE: Genomic DNA (xi) SEQUENCE DESCRIPTION: SEQ ID NO:1:

```
CGCAAAGCCG AGGAAACGAA CCGCATTATG GGATGTATCG GGAAAGTCCT CGGCGCGCTG      60

CTAACCATTG TCAGCGTTGT GGCCGCTGTT TTTACCGGTG GGGCGAGTCT GGCGCTGGCT     120

GCGGTGGGAC TTGCGGTAAT GGTGGCCGAT GAAATTGTGA AGGCGGCGAC GGGAGTGTCG     180

TTTATTCAGC AGGCGCTAAA CCCGATTATG GAGCATGTGC TGAAGCCGTT AATGGAGCTG     240

ATTGGCAAGG CGATTACCAA AGCGCTGGAA GGATTAGGCG TCGATAAGAA AACGGCAGAG     300

ATGGCCGGCA GCATTGTTGG TGCGATTGTC GCCGCTATTG CCATGGTGGC GGTCATTGTG     360

GTGGTCGCAG TTGTCGGGAA AGGCGCGGCG GCGAAACTGG GTAACGCGCT GAGCAAAATG     420

ATGGGCGAAA CGATTAAGAA GTTGGTGCCT AACGTGCTGA AACAGTTGGC GCAAAACGGC     480

AGCAAACTCT TTACCCAGGG GATGCAACGT ATTACTAGCG GTCTGGGTAA TGTGGGTAGC     540

AAGATGGGCC TGCAAACGAA TGCCTTAAGT AAAGAGCTGG TAGGTAATAC CCTAAATAAA     600

GTGGCGTTGG GCATGGAAGT CACGAATACC GCAGCCCAGT CAGCCGGTGG TGTTGCCGAG     660

GGCGTATTTA TTAAAAATGC CAGCGAGGCG CTTGCTGATT TTATGCTCGC CCGTTTTGCC     720

ATGGATCAGA TTCAGCAGTG GCTTAAACAA TCCGTAGAAA TATTTGGTGA AAACCAGAAG     780

GTAACGGCGG AACTGCAAAA AGCCATGTCT TCTGCGGTAC AGCAAAATGC GGATGCTTCG     840

CGTTTTATTC TGCGCCAGAG TCGCGCATAA                                     870
```

(2) INFORMATION FOR SEQ ID NO:2:

(i) SEQUENCE CHARACTERISTICS:
      (A) LENGTH: 1230 base pairs
      (B) TYPE: nucleic acid
      (C) STRANDEDNESS: double
      (D) TOPOLOGY: linear (ii) MOLECULE TYPE: Genomic DNA (xi) SEQUENCE DESCRIPTION: SEQ ID NO:2:

```
ATGTTAATTA GTAATGTGGG AATAAATCCC GCCGCTTATT TAAATAATCA TTCTGTTGAG      60

AATAGTTCAC AGACAGCTTC GCAATCCGTT AGCGCTAAAG ATATTCTGAA TAGTATTGGT     120

ATTAGCAGCA GTAAAGTCAG TGACCTGGGG TTGAGTCCTA CACTGAGCGC GCCTGCGCCA     180

GGGGTATTAA CGCAAACCCC CGGAACGATC ACGTCCTTTT TAAAAGCCAG TATTCAAAAT     240

ACCGACATGA ATCAGGATTT GAATGCTCTG GCAAATAATG TCACGACTAA AGCGAATGAG     300

GTTGTGCAAA CCCAGTTACG CGAGCAGCAG GCAGAAGTCG GAAAGTTTTT TGATATTAGC     360

GGAATGTCTT CCAGTGCCGT TGCGCTGTTG GCTGCCGCGA ATACGTTAAT GCTGACGTTG     420

AACCAGGCTG ATAGCAAACT GTCTGGTAAG TTGTCATTAG TCAGTTTTGA TGCAGCTAAA     480

ACGACGGCAA GCTCCATGAT GCGCGAAGGG ATGAATGCGT TGTCCGGTAG TATTTCCCAG     540

AGCGCGCTTC AGTTGGGGAT CACTGGCGTG GGCGCCAAAC TGGAATATAA GGGGCTGCAG     600

AATGAAAGAG GCGCGCTTAA ACATAATGCC GCGAAGATCG ATAAACTGAC CACTGAAAGC     660

CACAGTATTA AAAACGTGCT GAACGGGCAG AATAGCGTCA AACTCGGTGC TGAAGGCGTC     720

GATTCTCTGA AATCGTTAAA TATGAAGAAA ACCGGTACCG ATGCGACGAA AAATCTTAAT     780

GATGCGACGC TTAAATCTAA TGCCGGAACC AGCGCCACGG AAAGTCTGGG TATTAAAGAC     840

AGTAATAAAC AAATCTCCCC TGAACATCAG GCTATTCTGT CGAAACGTCT TGAGTCTGTC     900

GAATCCGATA TTCGTCTTGA GCAGAATACC ATGGATATGA CCCGAATCGA TGCGCGCAAG     960

ATGCAGATGA CGGGCGATCT GATTATGAAG AACTCGGTCA CGGTCGGTGG TATTGCAGGG    1020

GCGTCCGGGC AGTACGCCGC TACTCAGGAA CGTTCCGAGC AGCAAATTAG CCAGGTGAAT    1080

AACCGGGTTG CCAGCACCGC ATCGGACGAA GCCCGTGAAA GTTCACGTAA ATCGACCAGC    1140

CTGATTCAGG AAATGCTGAA AACAATGGAG AGCATTAACC AGTCGAAAGC ATCCGCACTC    1200

GCTGCTATCG CAGGCAATAT TCGCGCTTAA                                     1230
```

(2) INFORMATION FOR SEQ ID NO:3:

(i) SEQUENCE CHARACTERISTICS:
        (A) LENGTH: 1032 base pairs
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:3:

```
ATGCTTAATA TTCAAAATTA TTCCGCTTCT CCTCATCCGG GGATCGTTGC CGAACGGCCG      60

CAGACTCCCT CGGCGAGCGA GCACGTCGAG ACTGCCGTGG TACCGTCTAC CACAGAACAT     120

CGCGGTACAG ATATCATTTC ATTATCGCAG GCGGCTACTA AAATCCACCA GGCACAGCAG     180

ACGCTGCAGT CAACGCCACC GATCTCTGAA GAGAATAATG ACGAGCGCAC GCTGGCGCGC     240

CAGCAGTTGA CCAGCAGCCT GAATGCGCTG GCGAAGTCCG GCGTGTCATT ATCCGCAGAA     300

CAAAATGAGA ACCTGCGGAG CGCGTTTTCT GCGCCGACGT CGGCCTTATT TAGCGCTTCG     360

CCTATGGCGC AGCCGAGAAC AACCATTTCT GATGCTGAGA TTTGGGATAT GGTTTCCCAA     420

AATATATCGG CGATAGGTGA CAGCTATCTG GGCGTTTATG AAAACGTTGT CGCAGTCTAT     480

ACCGATTTTT ATCAGGCCTT CAGTGATATT CTTTCCAAAA TGGAGGCTG GTTATTACCA      540

GGTAAGGACG GTAATACCGT TAAGCTAGAT GTTACCTCAC TCAAAAATGA TTTAAACAGT     600

TTAGTCAATA AATATAATCA AATAAACAGT AATACCGTTT TATTTCCAGC GCAGTCAGGC     660

AGCGGCGTTA AGTAGCCAC TGAAGCGGAA GCGAGACAGT GGCTCAGTGA ATTGAATTTA      720
```

-continued

```
CCGAATAGCT GCCTGAAATC TTATGGATCC GGTTATGTCG TCACCGTTGA TCTGACGCCA    780

TTACAAAAAA TGGTTCAGGA TATTGATGGT TTAGGCGCGC CGGGAAAAGA CTCAAAACTC    840

GAAATGGATA ACGCCAAATA TCAAGCCTGG CAGTCGGGTT TTAAAGCGCA GGAAGAAAAT    900

ATGAAAACCA CATTACAGAC GCTGACGCAA AAATATAGCA ATGCCAATTC ATTGTACGAC    960

AACCTGGTAA AAGTGCTGAG CAGTACGATA AGTAGCAGCC TGGAAACCGC CAAAAGCTTC   1020

CTGCAAGGAT AA                                                      1032
```

(2) INFORMATION FOR SEQ ID NO:4:

(i) SEQUENCE CHARACTERISTICS:
        (A) LENGTH: 194 base pairs
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:4:

```
ATGGTTACAA GTGTAAGGAC TCAGCCCCCC GTCATAATGC CAGGTATGCA GACCGAGATC     60

AAAACGCAGG CCACGAATCT TGCGGCGAAT CTTTCCGCAG TCAGAGAAAG TGCCACAGCG    120

ACGCTGTCAG GGGAAATTAA AGGCCCGCAA CTGGAAGATT TTCCCGCGCT GATCAAACAG    180

GCGAGTCTGG ATGC                                                     194
```

(2) INFORMATION FOR SEQ ID NO:5:

(i) SEQUENCE CHARACTERISTICS:
        (A) LENGTH: 290 amino acids
        (B) TYPE: amino acid
        (D) TOPOLOGY: linear (ii) MOLECULE TYPE: peptide (xi) SEQUENCE DESCRIPTION: SEQ ID NO:5:

```
Arg Lys Ala Glu Glu Thr Asn Arg Ile Met Gly Cys Ile Gly Lys Val
 1               5                  10                  15

Leu Gly Ala Leu Leu Thr Ile Val Ser Val Val Ala Ala Val Phe Thr
                20                  25                  30

Gly Gly Ala Ser Leu Ala Leu Ala Ala Val Gly Leu Ala Val Met Val
            35                  40                  45

Ala Asp Glu Ile Val Lys Ala Thr Gly Val Ser Phe Ile Gln Gln
        50                  55                  60

Ala Leu Asn Pro Ile Met Glu His Val Leu Lys Pro Leu Met Glu Leu
 65                  70                  75                  80

Ile Gly Lys Ala Ile Thr Lys Ala Leu Glu Gly Leu Gly Val Asp Arg
                85                  90                  95

Lys Arg Gln Arg Trp Pro Ala Ala Leu Leu Val Arg Leu Ser Pro Leu
                100                 105                 110

Cys His Gly Asp Ala Val Ile Val Val Val Ala Val Val Gly Lys Gly
            115                 120                 125

Ala Ala Ala Lys Leu Gly Asn Ala Leu Ser Lys Met Met Gly Glu Thr
    130                 135                 140

Ile Lys Lys Leu Val Pro Asn Val Leu Lys Gln Leu Ala Gln Asn Gly
145                 150                 155                 160

Ser Lys Leu Phe Thr Gln Gly Met Gln Arg Ile Thr Ser Gly Leu Gly
                165                 170                 175
```

-continued

```
Asn Val Gly Ser Lys Met Gly Leu Gln Thr Asn Ala Leu Ser Lys Glu
            180                 185                 190

Leu Val Gly Asn Thr Leu Asn Lys Val Ala Leu Gly Met Glu Val Thr
            195                 200                 205

Asn Thr Ala Ala Gln Ser Ala Gly Gly Val Ala Glu Gly Val Phe Ile
            210                 215                 220

Lys Asn Ala Ser Glu Ala Leu Ala Asp Phe Met Leu Ala Arg Phe Ala
225                 230                 235                 240

Met Asp Gln Ile Gln Gln Trp Leu Lys Gln Ser Val Glu Ile Phe Gly
            245                 250                 255

Glu Asn Gln Lys Val Thr Ala Glu Leu Gln Lys Ala Met Ser Ser Ala
            260                 265                 270

Val Gln Gln Asn Ala Asp Ala Ser Arg Phe Ile Leu Arg Gln Ser Arg
            275                 280                 285

Ala Glx
    290

(2) INFORMATION FOR SEQ ID NO:6:

(i) SEQUENCE CHARACTERISTICS:
        (A) LENGTH: 410 amino acids
        (B) TYPE: amino acid
        (D) TOPOLOGY: linear (ii) MOLECULE TYPE: peptide (xi) SEQUENCE DESCRIPTION: SEQ ID NO:6:

Met Leu Ile Ser Asn Val Gly Ile Asn Pro Ala Ala Tyr Leu Asn Asn
  1               5                  10                  15

His Ser Val Glu Asn Ser Ser Gln Thr Ala Ser Gln Ser Val Ser Ala
             20                  25                  30

Lys Asp Ile Leu Asn Ser Ile Gly Ile Ser Ser Ser Lys Val Ser Asp
             35                  40                  45

Leu Gly Leu Ser Pro Thr Leu Ser Ala Pro Ala Pro Gly Val Leu Thr
     50                  55                  60

Gln Thr Pro Gly Thr Ile Thr Ser Phe Leu Lys Ala Ser Ile Gln Asn
 65                  70                  75                  80

Thr Asp Met Asn Gln Asp Leu Asn Ala Leu Ala Asn Asn Val Thr Thr
                 85                  90                  95

Lys Ala Asn Glu Val Val Gln Thr Gln Leu Arg Glu Gln Gln Ala Glu
            100                 105                 110

Val Gly Lys Phe Phe Asp Ile Ser Gly Met Ser Ser Ser Ala Val Ala
            115                 120                 125

Leu Leu Ala Ala Ala Asn Thr Leu Met Leu Thr Leu Asn Gln Ala Asp
            130                 135                 140

Ser Lys Leu Ser Gly Lys Leu Ser Leu Val Ser Phe Asp Ala Ala Lys
145                 150                 155                 160

Thr Thr Ala Ser Ser Met Met Arg Glu Gly Met Asn Ala Leu Ser Gly
            165                 170                 175

Ser Ile Ser Gln Ser Ala Leu Gln Leu Gly Ile Thr Gly Val Gly Ala
            180                 185                 190

Lys Leu Glu Tyr Lys Gly Leu Gln Asn Glu Arg Gly Ala Leu Lys His
            195                 200                 205

Asn Ala Ala Lys Ile Asp Lys Leu Thr Thr Glu Ser His Ser Ile Lys
            210                 215                 220

Asn Val Leu Asn Gly Gln Asn Ser Val Lys Leu Gly Ala Glu Gly Val
```

-continued

```
225                 230                 235                 240

Asp Ser Leu Lys Ser Leu Asn Met Lys Lys Thr Gly Thr Asp Ala Thr
                245                 250                 255

Lys Asn Leu Asn Asp Ala Thr Leu Lys Ser Asn Ala Gly Thr Ser Ala
                260                 265                 270

Thr Glu Ser Leu Gly Ile Lys Asp Ser Asn Lys Gln Ile Ser Pro Glu
                275                 280                 285

His Gln Ala Ile Leu Ser Lys Arg Leu Glu Ser Val Glu Ser Asp Ile
            290                 295                 300

Arg Leu Glu Gln Asn Thr Met Asp Met Thr Arg Ile Asp Ala Arg Lys
305                 310                 315                 320

Met Gln Met Thr Gly Asp Leu Ile Met Lys Asn Ser Val Thr Val Gly
                325                 330                 335

Gly Ile Ala Gly Ala Ser Gly Gln Tyr Ala Ala Thr Gln Glu Arg Ser
                340                 345                 350

Glu Gln Gln Ile Ser Gln Val Asn Asn Arg Val Ala Ser Thr Ala Ser
            355                 360                 365

Asp Glu Ala Arg Glu Ser Ser Arg Lys Ser Thr Ser Leu Ile Gln Glu
        370                 375                 380

Met Leu Lys Thr Met Glu Ser Ile Asn Gln Ser Lys Ala Ser Ala Leu
385                 390                 395                 400

Ala Ala Ile Ala Gly Asn Ile Arg Ala Glx
                405                 410
```

(2) INFORMATION FOR SEQ ID NO:7:

(i) SEQUENCE CHARACTERISTICS:
        (A) LENGTH: 344 amino acids
        (B) TYPE: amino acid
        (D) TOPOLOGY: linear (ii) MOLECULE TYPE: peptide (xi) SEQUENCE DESCRIPTION: SEQ ID NO:7:

```
Met Leu Asn Ile Gln Asn Tyr Ser Ala Ser Pro His Pro Gly Ile Val
 1                   5                  10                  15

Ala Glu Arg Pro Gln Thr Pro Ser Ala Ser Glu His Val Glu Thr Ala
                20                  25                  30

Val Val Pro Ser Thr Thr Glu His Arg Gly Thr Asp Ile Ile Ser Leu
            35                  40                  45

Ser Gln Ala Ala Thr Lys Ile His Gln Ala Gln Gln Thr Leu Gln Ser
        50                  55                  60

Thr Pro Pro Ile Ser Glu Glu Asn Asn Asp Glu Arg Thr Leu Ala Arg
65                  70                  75                  80

Gln Gln Leu Thr Ser Ser Leu Asn Ala Leu Ala Lys Ser Gly Val Ser
                85                  90                  95

Leu Ser Ala Glu Gln Asn Glu Asn Leu Arg Ser Ala Phe Ser Ala Pro
                100                 105                 110

Thr Ser Ala Leu Phe Ser Ala Ser Pro Met Ala Gln Pro Arg Thr Thr
            115                 120                 125

Ile Ser Asp Ala Glu Ile Trp Asp Met Val Ser Gln Asn Ile Ser Ala
        130                 135                 140

Ile Gly Asp Ser Tyr Leu Gly Val Tyr Glu Asn Val Val Ala Val Tyr
145                 150                 155                 160

Thr Asp Phe Tyr Gln Ala Phe Ser Asp Ile Leu Ser Lys Met Gly Gly
                165                 170                 175
```

```
Trp Leu Leu Pro Gly Lys Asp Gly Asn Thr Val Lys Leu Asp Val Thr
            180                 185                 190

Ser Leu Lys Asn Asp Leu Asn Ser Leu Val Asn Lys Tyr Asn Gln Ile
        195                 200                 205

Asn Ser Asn Thr Val Leu Phe Pro Ala Gln Ser Gly Ser Gly Val Lys
    210                 215                 220

Val Ala Thr Glu Ala Glu Ala Arg Gln Trp Leu Ser Glu Leu Asn Leu
225                 230                 235                 240

Pro Asn Ser Cys Leu Lys Ser Tyr Gly Ser Gly Tyr Val Val Thr Val
                245                 250                 255

Asp Leu Thr Pro Leu Gln Lys Met Val Gln Asp Ile Asp Gly Leu Gly
            260                 265                 270

Ala Pro Gly Lys Asp Ser Lys Leu Glu Met Asp Asn Ala Lys Tyr Gln
        275                 280                 285

Ala Trp Gln Ser Gly Phe Lys Ala Gln Glu Glu Asn Met Lys Thr Thr
    290                 295                 300

Leu Gln Thr Leu Thr Gln Lys Tyr Ser Asn Ala Asn Ser Leu Tyr Asp
305                 310                 315                 320

Asn Leu Val Lys Val Leu Ser Ser Thr Ile Ser Ser Ser Leu Glu Thr
                325                 330                 335

Ala Lys Ser Phe Leu Gln Gly Glx
            340
```

(2) INFORMATION FOR SEQ ID NO:8:

(i) SEQUENCE CHARACTERISTICS:
        (A) LENGTH: 64 amino acids
        (B) TYPE: amino acid
        (D) TOPOLOGY: linear (ii) MOLECULE TYPE: peptide (xi) SEQUENCE DESCRIPTION: SEQ ID NO:8:

```
Met Val Thr Ser Val Arg Thr Gln Pro Pro Val Ile Met Pro Gly Met
1               5                   10                  15

Gln Thr Glu Ile Lys Thr Gln Ala Thr Asn Leu Ala Ala Asn Leu Ser
            20                  25                  30

Ala Val Arg Glu Ser Ala Thr Ala Thr Leu Ser Gly Glu Ile Lys Gly
        35                  40                  45

Pro Gln Leu Glu Asp Phe Pro Ala Leu Ile Lys Gln Ala Ser Leu Asp
    50                  55                  60
```

(2) INFORMATION FOR SEQ ID NO:9:

(i) SEQUENCE CHARACTERISTICS:
        (A) LENGTH: 483 base pairs
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:9:

```
ATGCATTATT TTTTTATCAT CGTAATCTGG TTGCTTAGCA TAAATACGGC ATGGGCTGAT    60

TCTGGCTTCA GGCTGAAAAA ATGTTCAATA TTGAATCCGA ACTACTTTAC GCTATCGCCC    120

AGCAGGAATC GGCGATGAAA CCTGGCGCCA TTGGTCATAA CCGAGATGGT TCAACCGATC    180

TTGGCCTGAT GCAAATTAAC AGCTTCCATA TGAAAGGCT GAAAAAAATG GGGATTAGTG     240
```

-continued

```
AAAAACAGTT GTTACAGGAC CCCTGCATTT CTGTCATTGT GGGCGACCTC CATTTTATCA      300

GATATGATGA AAATCTACGG TTATAGCTGG GAGGCCGTTG GCGCTTATAA TGCCGGGACG      360

TCGCCGAAAC GATCGGATAT AAGGAAACGT TATGCTAAAA AAATTTGGGA GAATTACAGA      420

AAATTAAAAG GAATGTCAGC AGAAGAGAAA AACAAAGAC TTTCTATCGC GGCAAACAAA      480

TAA                                                                    483
```

(2) INFORMATION FOR SEQ ID NO:10:

(i) SEQUENCE CHARACTERISTICS:
       (A) LENGTH: 579 base pairs
       (B) TYPE: nucleic acid
       (C) STRANDEDNESS: double
       (D) TOPOLOGY: linear (ii) MOLECULE TYPE: Genomic DNA (xi) SEQUENCE DESCRIPTION: SEQ ID NO:10:

```
ATCAGCTTGC CGTCGTCATA AGCAACTGGG CTTGCATTGC TTTTAGTTGT ACAAACTGTG       60

CAGGCGTCTT CCAGCATTCT ATTGTTCCGT GAATCCGGAA ATCTGCACGT ACCTGCTCCA      120

GATTACTATG AGGATTATCC TTAAGTACAA GGGCCGCCGC CATCGTTCCG GTTCTTCCCA      180

CTCCGCCCAG ACAATGAATC ATCGGTAAAT GCTTATCTGA TGAACTACGC CCCGGCGCGC      240

CATTTTGGTT ACTATTTTTC ACCCTATCCG CCAGGTATTC TAACTGATCC GTAGACGGTA      300

ACGGCTGGTG ATCTGGCCAA TTTTTCACAT GCAATACCGG GATTGTATAC CGCTTTCCCC      360

GCAGGACAGT TGCATATTGT ATTGGTCTAT CGCTTCTCCC TGACTGGCTG AGCTCTCTTT      420

TTGGCTGTTG GTATGCACCT CGCCAAAGGT GTAGCTCCCT CTGAAATAGG TGGTAATTGT      480

TTTGCCTGCA TCTGATCTTC CGACGTTAAC ACCACCAGGC ACGAGCATTC TTTTTCAAGA      540

AGCATTTTCA TATGCGCTTC CAGCGCATCC CGGCGATTT                            579
```

(2) INFORMATION FOR SEQ ID NO:11:

(i) SEQUENCE CHARACTERISTICS:
       (A) LENGTH: 160 amino acids
       (B) TYPE: amino acid
       (D) TOPOLOGY: linear (ii) MOLECULE TYPE: peptide (xi) SEQUENCE DESCRIPTION: SEQ ID NO:11:

```
Met His Tyr Phe Phe Ile Ile Val Ile Trp Leu Leu Ser Ile Asn Thr
  1               5                  10                  15

Ala Trp Ala Asp Ser Gly Phe Arg Leu Lys Lys Cys Ser Ile Leu Asn
             20                  25                  30

Pro Asn Tyr Phe Thr Leu Ser Pro Ser Arg Asn Arg Glx Asn Leu
         35                  40                  45

Ala Pro Leu Val Ile Thr Glu Met Val Gln Pro Ile Leu Ala Glx Cys
         50                  55                  60

Lys Leu Thr Ala Ser Ile Glx Lys Gly Glx Lys Lys Trp Gly Leu Val
 65                  70                  75                  80

Lys Asn Ser Cys Tyr Arg Thr Pro Ala Phe Leu Ser Leu Trp Ala Thr
             85                  90                  95

Ser Ile Leu Ser Asp Met Met Lys Ile Tyr Gly Tyr Ser Trp Glu Ala
            100                 105                 110

Val Gly Ala Tyr Asn Ala Gly Thr Ser Pro Lys Arg Ser Asp Ile Arg
            115                 120                 125
```

```
Lys Arg Tyr Ala Lys Lys Ile Trp Glu Asn Tyr Arg Lys Leu Lys Gly
130                 135                 140
Met Ser Ala Glu Glu Lys Asn Lys Arg Leu Ser Ile Ala Ala Asn Lys
145                 150                 155                 160
```

(2) INFORMATION FOR SEQ ID NO:12:

(i) SEQUENCE CHARACTERISTICS:
        (A) LENGTH: 239 amino acids
        (B) TYPE: amino acid
        (D) TOPOLOGY: linear (ii) MOLECULE TYPE: peptide (xi) SEQUENCE DESCRIPTION: SEQ ID NO:12:

```
Trp Pro Gly Thr Ile Cys Gly Gln Gln His Ser Ile Asn Gln Gln Thr
1                   5                   10                  15
Gln Val Lys Leu Ser Asp Gly Met Pro Val Pro Val Ile Arg Leu Thr
                20                  25                  30
Phe Asp Gly Lys Pro Val Ala Leu Ala Gly Ile Arg Thr Gln Lys Ile
                35                  40                  45
Arg Pro Asp Arg Leu Glu Ala His Met Lys Met Leu Leu Glu Lys Glu
50                  55                  60
Cys Ser Cys Leu Val Val Leu Thr Ser Glu Arg Ser Asp Ala Gly Lys
65                  70                  75                  80
Thr Ile Thr Thr Tyr Phe Arg Gly Ser Tyr Thr Phe Gly Glu Val His
                85                  90                  95
Thr Asn Ser Gln Lys Val Ser Ser Ala Ser Gln Gly Glu Ala Ile Asp
                100                 105                 110
Gln Tyr Asn Met Gln Leu Ser Cys Gly Glu Lys Arg Tyr Thr Ile Pro
                115                 120                 125
Val Leu His Val Lys Asn Trp Pro Asp His Gln Pro Leu Pro Ser Thr
130                 135                 140
Asp Gln Leu Glu Tyr Leu Ala Asp Arg Val Lys Asn Ser Asn Gln Asn
145                 150                 155                 160
Gly Ala Pro Gly Arg Ser Ser Asp Lys His Leu Pro Met Ile His
                165                 170                 175
Cys Leu Gly Gly Val Gly Arg Thr Gly Thr Met Ala Ala Ala Leu Val
                180                 185                 190
Leu Lys Asp Asn Pro His Ser Asn Leu Glu Gln Val Arg Ala Asp Phe
                195                 200                 205
Arg Ile His Gly Thr Ile Glu Cys Trp Lys Thr Pro Ala Gln Phe Val
210                 215                 220
Gln Leu Lys Ala Met Gln Ala Gln Leu Leu Met Thr Thr Ala Ser
225                 230                 235
```

(2) INFORMATION FOR SEQ ID NO:13:

(i) SEQUENCE CHARACTERISTICS:
        (A) LENGTH: 1538 base pairs
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:13:

```
ATGCGTGATT GCCTGAATAA CGGCAATCCA GTGCTTAACG TGGGAGCGTC AGGTCTTACC      60

ACCTTACCAG ACCGTTTACC ACCGCATATT ACAACACTGG TTATTCCTGA TAATAATCTG     120
```

```
ACCAGCCTGC CGGAGTTGCC GGAAGGACTA CGGGAGCTGG AGGTCTCTGG TAACCTACAA    180

CTGACCAGCC TGCCATCGCT GCCGCAGGGA CTACAGAAGC TGTGGGCCTA TAATAATTGG    240

CTGGCCAGCC TGCCGACGTT GCCGCCAGGA CTAGGGATC  TGGCGGTCTC TAATAACCAG    300

CTGACCAGCC TGCCGGAGAT GCCGCCAGCA CTACGGGAGC TGAGGGTCTC TGGTAACAAC    360

CTGACCAGCT GCGCGCGCTG CCGTCAGGAC TACAGAAGCT GTGGGCCTAT AATAATCGGC    420

TGACCAGCCT GCCGGAGATG TCGCCAGGAC TACAGGAGCT GGATGTCTCT CATAACCAGC    480

TGACCCGCCT GCCGCAAAGC CTCACGGGTC TGTCTTCAGC GGCACGCGTA TATCTGGACG    540

GGAATCCACT GTCTGTACGC ACTCGTGACA GGCTCTGCGG ACATCATTGG CCATTCAGGC    600

ATCAGGATAC ACTTCGATAT GGCGGGGCCT TCCGTCCCCG GAAGCCCGG  GCACTGCACC    660

TGGCGGTCGC TGACTGGCTG ACGTCTGCAC GGGAGGGGGA AGCGGCCCAG GCAGACAGAT    720

GGCAGGCGTT CGGACTGGAA GATAACGCCG CCGCCTTCAG CCTGGTCCTG ACAGACTGC     780

GTGAGACGGA AAACTTCAAA AAGACGCGG  GCTTTAAGGC ACAGATATCA TCCTGGCTGA    840

CACAACTGGC TGAAGATGCT GCGCTGAGAG CAAAAACCTT TGCCATGGCA ACAGAGGCAA    900

CATCAACCTG CGAGGACCGG GTCACACATG CCCTGCACCA GATGAATAAC GTACAACTGG    960

TACATAATGC AGAAAAAGGG GAATACGACA ACAATCTCCA GGGGCTGGTT TCCACGGGGC   1020

GTGAGATGTT CCGCCTGGCA ACACTGGAAC AGATTGCCCG GGAAAAAGCC GGAACACTGG   1080

CTTTAGTCGA TGACGTTGAG GTCTATCTGG CGTTCCAGAA TAAGCTGAAG GAATCACTTG   1140

AGCTGACCAG CGTGACGTCA GAAATGCGTT TCTTTGACGT TTCCGGCGTG ACGGTTTCAG   1200

ACCTTCAGGC TGCGGACGTT CAGGTGAAAA CCGCTGAAAA CAGCGGGTTC AGTAAATGGA   1260

TACTGCAGTG GGGGCCGTTA CACAGCGTGC TGGAACGCAA AGTGCCGGAA CGCTTTAACG   1320

CGCTTCGTGA AAAGCAAATA TCGGATTATG AAGACACGTA CCGGAAGCTG TATGACGAAG   1380

TGCTGAAATC GTCCGGGCTG GTCGACGATA CCGATGCAGA ACGTACTATC GGAGTAAGTG   1440

CGATGGATAG TGCGAAAAAA GAATTTCTGG ATGGCCTGCG CGCTCTTGTG GATGAGGTGC   1500

TGGGTAGCTA TCTGACAGCC CGGTGGCGTC TTAACTGA                           1538
```

(2) INFORMATION FOR SEQ ID NO:14:

(i) SEQUENCE CHARACTERISTICS:
        (A) LENGTH: 513 amino acids
        (B) TYPE: amino acid
        (D) TOPOLOGY: linear (ii) MOLECULE TYPE: peptide (xi) SEQUENCE DESCRIPTION: SEQ ID NO:14:

```
Met Arg Asp Cys Leu Asn Asn Gly Asn Pro Val Leu Asn Val Gly Ala
 1               5                  10                  15

Ser Gly Leu Thr Thr Leu Pro Asp Arg Leu Pro Pro His Ile Thr Thr
                20                  25                  30

Leu Val Ile Pro Asp Asn Asn Leu Thr Ser Leu Pro Glu Leu Pro Glu
            35                  40                  45

Gly Leu Arg Glu Leu Glu Val Ser Gly Asn Leu Gln Leu Thr Ser Leu
        50                  55                  60

Pro Ser Leu Pro Gln Gly Leu Gln Lys Leu Trp Ala Tyr Asn Asn Trp
 65                  70                  75                  80

Leu Ala Ser Leu Pro Thr Leu Pro Pro Gly Leu Gly Asp Leu Ala Val
                85                  90                  95
```

-continued

```
Ser Asn Asn Gln Leu Thr Ser Leu Pro Glu Met Pro Pro Ala Leu Arg
            100                 105                 110

Glu Leu Arg Val Ser Gly Asn Asn Leu Thr Ser Leu Arg Ala Leu Pro
            115                 120                 125

Ser Gly Leu Gln Lys Leu Trp Ala Tyr Asn Asn Arg Leu Thr Ser Leu
    130                 135                 140

Pro Glu Met Ser Pro Gly Leu Gln Glu Leu Asp Val Ser His Asn Gln
145                 150                 155                 160

Leu Thr Arg Leu Pro Gln Ser Leu Thr Gly Leu Ser Ser Ala Ala Arg
                165                 170                 175

Val Tyr Leu Asp Gly Asn Pro Leu Ser Val Arg Thr Arg Asp Arg Leu
            180                 185                 190

Cys Gly His His Trp Pro Phe Arg His Gln Asp Thr Leu Arg Tyr Gly
            195                 200                 205

Gly Ala Phe Arg Pro Arg Glu Ala Arg Ala Leu His Leu Ala Val Ala
    210                 215                 220

Asp Trp Leu Thr Ser Ala Arg Glu Gly Glu Ala Ala Gln Ala Asp Arg
225                 230                 235                 240

Trp Gln Ala Phe Gly Leu Glu Asp Asn Ala Ala Ala Phe Ser Leu Val
                245                 250                 255

Leu Asp Arg Leu Arg Glu Thr Glu Asn Phe Lys Lys Asp Ala Gly Phe
            260                 265                 270

Lys Ala Gln Ile Ser Ser Trp Leu Thr Gln Leu Ala Glu Asp Ala Ala
            275                 280                 285

Leu Arg Ala Lys Thr Phe Ala Met Ala Thr Glu Ala Thr Ser Thr Cys
    290                 295                 300

Glu Asp Arg Val Thr His Ala Leu His Gln Met Asn Asn Val Gln Leu
305                 310                 315                 320

Val His Asn Ala Glu Lys Gly Glu Tyr Asp Asn Asn Leu Gln Gly Leu
                325                 330                 335

Val Ser Thr Gly Arg Glu Met Phe Arg Leu Ala Thr Leu Glu Gln Ile
            340                 345                 350

Ala Arg Glu Lys Ala Gly Thr Leu Ala Leu Val Asp Asp Val Glu Val
            355                 360                 365

Tyr Leu Ala Phe Gln Asn Lys Leu Lys Glu Ser Leu Glu Leu Thr Ser
    370                 375                 380

Val Thr Ser Glu Met Arg Phe Phe Asp Val Ser Gly Val Thr Val Ser
385                 390                 395                 400

Asp Leu Gln Ala Ala Asp Val Gln Val Lys Thr Ala Glu Asn Ser Gly
                405                 410                 415

Phe Ser Lys Trp Ile Leu Gln Trp Gly Pro Leu His Ser Val Leu Glu
            420                 425                 430

Arg Lys Val Pro Glu Arg Phe Asn Ala Leu Arg Glu Lys Gln Ile Ser
            435                 440                 445

Asp Tyr Glu Asp Thr Tyr Arg Lys Leu Tyr Asp Glu Val Leu Lys Ser
    450                 455                 460

Ser Gly Leu Val Asp Asp Thr Asp Ala Glu Arg Thr Ile Gly Val Ser
465                 470                 475                 480

Ala Met Asp Ser Ala Lys Lys Glu Phe Leu Asp Gly Leu Arg Ala Leu
                485                 490                 495

Val Asp Glu Val Leu Gly Ser Tyr Leu Thr Ala Arg Trp Arg Leu Asn
            500                 505                 510

Glx
```

(2) INFORMATION FOR SEQ ID NO:15:

(i) SEQUENCE CHARACTERISTICS:
        (A) LENGTH: 3441 base pairs
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:15:

```
CGCAAAGCCG AGGAAACGAA CCGCATTATG GGATGTATCG GGAAAGTCCT CGGCGCGCTG      60

CTAACCATTG TCAGCGTTGT GGCCGCTGTT TTTACCGGTG GGGCGAGTCT GGCGCTGGCT     120

GCGGTGGGAC TTGCGGTAAT GGTGGCCGAT GAAATTGTGA AGGCGGCGAC GGGAGTGTCG     180

TTTATTCAGC AGGCGCTAAA CCCGATTATG GAGCATGTGC TGAAGCCGTT AATGGAGCTG     240

ATTGGCAAGG CGATTACCAA AGCGCTGGAA GGATTAGGCG TCGATAAGAA AACGGCAGAG     300

ATGGCCGGCA GCATTGTTGG TGCGATTGTC GCCGCTATTG CCATGGTGGC GGTCATTGTG     360

GTGGTCGCAG TTGTCGGGAA AGGCGCGGCG GCGAAACTGG GTAACGCGCT GAGCAAAATG     420

ATGGGCGAAA CGATTAAGAA GTTGGTGCCT AACGTGCTGA AACAGTTGGC GCAAAACGGC     480

AGCAAACTCT TTACCCAGGG GATGCAACGT ATTACTAGCG GTCTGGGTAA TGTGGGTAGC     540

AAGATGGGCC TGCAAACGAA TGCCTTAAGT AAAGAGCTGG TAGGTAATAC CCTAAATAAA     600

GTGGCGTTGG GCATGGAAGT CACGAATACC GCAGCCCAGT CAGCCGGTGG TGTTGCCGAG     660

GGCGTATTTA TTAAAAATGC CAGCGAGGCG CTTGCTGATT TTATGCTCGC CCGTTTTGCC     720

ATGGATCAGA TTCAGCAGTG GCTTAAACAA TCCGTAGAAA TATTTGGTGA AAACCAGAAG     780

GTAACGGCGG AACTGCAAAA AGCCATGTCT TCTGCGGTAC AGCAAAATGC GGATGCTTCG     840

CGTTTTATTC TGCGCCAGAG TCGCGCATAA AAACTGCCAA AATAAAGGGA GAAAATATG      900

TTAATTAGTA ATGTGGGAAT AAATCCCGCC GCTTATTTAA ATAATCATTC TGTTGAGAAT     960

AGTTCACAGA CAGCTTCGCA ATCCGTTAGC GCTAAAGATA TTCTGAATAG TATTGGTATT    1020

AGCAGCAGTA AAGTCAGTGA CCTGGGGTTG AGTCCTACAC TGAGCGCGCC TGCGCCAGGG    1080

GTATTAACGC AAACCCCCGG AACGATCACG TCCTTTTTAA AAGCCAGTAT TCAAAATACC    1140

GACATGAATC AGGATTTGAA TGCTCTGGCA AATAATGTCA CGACTAAAGC GAATGAGGTT    1200

GTGCAAACCC AGTTACGCGA GCAGCAGGCA GAAGTCGGAA AGTTTTTTGA TATTAGCGGA    1260

ATGTCTTCCA GTGCCGTTGC GCTGTTGGCT GCCGCGAATA CGTTAATGCT GACGTTGAAC    1320

CAGGCTGATA GCAAACTGTC TGGTAAGTTG TCATTAGTCA GTTTTGATGC AGCTAAAACG    1380

ACGGCAAGCT CCATGATGCG CGAAGGGATG AATGCGTTGT CCGGTAGTAT TTCCCAGAGC    1440

GCGCTTCAGT TGGGGATCAC TGGCGTGGGC GCCAAACTGG AATATAAGGG CTGCAGAAT     1500

GAAAGAGGCG CGCTTAAACA TAATGCCGCG AAGATCGATA AACTGACCAC TGAAAGCCAC    1560

AGTATTAAAA ACGTGCTGAA CGGGCAGAAT AGCGTCAAAC TCGGTGCTGA AGGCGTCGAT    1620

TCTCTGAAAT CGTTAAATAT GAAGAAAACC GGTACCGATG CGACGAAAAA TCTTAATGAT    1680

GCGACGCTTA AATCTAATGC CGGAACCAGC GCCACGGAAA GTCTGGGTAT TAAAGACAGT    1740

AATAAACAAA TCTCCCCTGA ACATCAGGCT ATTCTGTCGA AACGTCTTGA GTCTGTCGAA    1800

TCCGATATTC GTCTTGAGCA GAATACCATG GATATGACCC GAATCGATGC GCGCAAGATG    1860

CAGATGACGG GCGATCTGAT TATGAAGAAC TCGGTCACGG TCGGTGGTAT TGCAGGGGCG    1920

TCCGGGCAGT ACGCCGCTAC TCAGGAACGT TCCGAGCAGC AAATTAGCCA GGTGAATAAC    1980
```

-continued

```
CGGGTTGCCA GCACCGCATC GGACGAAGCC CGTGAAAGTT CACGTAAATC GACCAGCCTG      2040

ATTCAGGAAA TGCTGAAAAC AATGGAGAGC ATTAACCAGT CGAAAGCATC CGCACTCGCT      2100

GCTATCGCAG GCAATATTCG CGCTTAATCT GAAAGGTCAT CTATACGCCA TCATGGGTGT      2160

GATTTAATCG CGCTCCTGAT GGCGAACTGG GGATATTATG CTTAATATTC AAAATTATTC      2220

CGCTTCTCCT CATCCGGGGA TCGTTGCCGA ACGGCCGCAG ACTCCCTCGG CGAGCGAGCA      2280

CGTCGAGACT GCCGTGGTAC CGTCTACCAC AGAACATCGC GGTACAGATA TCATTTCATT      2340

ATCGCAGGCG GCTACTAAAA TCCACCAGGC ACAGCAGACG CTGCAGTCAA CGCCACCGAT      2400

CTCTGAAGAG AATAATGACG AGCGCACGCT GGCGCGCCAG CAGTTGACCA GCAGCCTGAA      2460

TGCGCTGGCG AAGTCCGGCG TGTCATTATC CGCAGAACAA AATGAGAACC TGCGGAGCGC      2520

GTTTTCTGCG CCGACGTCGG CCTTATTTAG CGCTTCGCCT ATGGCGCAGC CGAGAACAAC      2580

CATTTCTGAT GCTGAGATTT GGGATATGGT TTCCCAAAAT ATATCGGCGA TAGGTGACAG      2640

CTATCTGGGC GTTTATGAAA ACGTTGTCGC AGTCTATACC GATTTTTATC AGGCCTTCAG      2700

TGATATTCTT TCCAAAATGG GAGGCTGGTT ATTACCAGGT AAGGACGGTA ATACCGTTAA      2760

GCTAGATGTT ACCTCACTCA AAAATGATTT AAACAGTTTA GTCAATAAAT ATAATCAAAT      2820

AAACAGTAAT ACCGTTTTAT TTCCAGCGCA GTCAGGCAGC GGCGTTAAAG TAGCCACTGA      2880

AGCGGAAGCG AGACAGTGGC TCAGTGAATT GAATTTACCG AATAGCTGCC TGAAATCTTA      2940

TGGATCCGGT TATGTCGTCA CCGTTGATCT GACGCCATTA CAAAAAATGG TTCAGGATAT      3000

TGATGGTTTA GGCGCGCCGG GAAAAGACTC AAAACTCGAA ATGGATAACG CCAAATATCA      3060

AGCCTGGCAG TCGGGTTTTA AAGCGCAGGA AGAAAATATG AAAACCACAT TACAGACGCT      3120

GACGCAAAAA TATAGCAATG CCAATTCATT GTACGACAAC CTGGTAAAAG TGCTGAGCAG      3180

TACGATAAGT AGCAGCCTGG AAACCGCCAA AAGCTTCCTG CAAGGATAAC AGAAGAGGAT      3240

ATTAATAATG GTTACAAGTG TAAGGACTCA GCCCCCCGTC ATAATGCCAG GTATGCAGAC      3300

CGAGATCAAA ACGCAGGCCA CGAATCTTGC GGCGAATCTT TCCGCAGTCA GAGAAAGTGC      3360

CACAGCGACG CTGTCAGGGG AAATTAAAGG CCCGCAACTG GAAGATTTTC CCGCGCTGAT      3420

CAAACAGGCG AGTCTGGATG C                                              3441
```

(2) INFORMATION FOR SEQ ID NO:16:

(i) SEQUENCE CHARACTERISTICS:
        (A) LENGTH: 3851 base pairs
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:16:

```
GAGCTCAGCA ACGTGTCGAA AGCCTGTAAA ATCATGGGCG TCTCGCGCGA TACGTTTTAC        60

CGTTATCGTG AACTGGCCGA TGAAGGCGGC GTTGATGCGC TGATAAATCG TAGTCGCCGC       120

GTACCTAACC TTAAGAACCG TACCGATGAG GCAACTGAGC AAGCTGTTGT TGATTATGCC       180

GTTGCGTTCC CGGCCCATGG TCAGCACCGA ACTGCGCAAA CAGGACGTTT TTATCTCCGG       240

TAGTGATGTC CATTCCGTCT GGCTGCGCAC AACCTTGAGA ACTTCAAAAA ACGCCTGAAA       300

GCGCTGGAAG AAAAAGTGGC CCGCGATGGC ATTGAACTGA CTGCCAGATC GCCGCGCTGG       360

AGCGTAAAGC CAGTGATGAT GAAGCCTGTG GTGAGATTGA AACCGTTCAT CCGGGATATC       420

TGGGGTCACA GGACACGTTC TACGTGGGCA ACCTGAAAGG CGTTGGGCGA ATCTATCAGC       480
```

```
AGACGTTCGT TGATACATAC TCGAAGGTGG CTCACTGCAA GCGCTATATC ACCAAAACGC    540

CGATTACAGC GGCTGATTTG CTGAATGATC GTGTACTGCC GTTTATGAGT CTCAGGGCCT    600

GCCGATGCTA AGGATACTGA CAGACAGGGG TACAGAATAT TGCGGCAAAG TGGAACATCA    660

TGATTATCAG CTTTATCTGG AGATAAATGA CATCGAACAC ACGAAAACGA AGGCGATGTC    720

CCCGCAGACC AATGGCATCT GCGAGCGGTT CCATAAAACG ATACTGAACG AATTTTATCA    780

GGTGACGTTC CGCAAAAAGT TATATGGCGA TTTTGATACA TTACAATCGG ATCTTGATGA    840

ATGGCTGGTT CACTATAATA ATGAGCGAAC CCATCAGGGA AAAATGTGCT GTGGCCGGAC    900

GCCGATGGAA ACGTTACTTG ATGGAAAACG CATCTGGTCT GAGAAGAATT TAAGCCAGAT    960

GTAATCTGAC AGATACCTGT ATAAATAACC GGTAACTGTC AGATCAGGTC TGAGCTAATA   1020

CAACTAATTG TATGTTATTT GTCGTTTATT GCTAAATATA TATCGTTAAT TGAAGGCTTG   1080

ATGCGTGTGT CTGCGTTAAT CTCTTTTCAT TGTGCTGTAA ATTAGGCAGT GGAATATGTT   1140

TAATATCCGC AATACACAAC CTTCTGTAAG TATGCAGGCT ATTGCTGGTG CAGCGGCACC   1200

AGAGGCATCT CCGGAAGAAA TTGTATGGGA AAAATTCAGG TTTTTTTCCC GCAGGAAAAT   1260

TACGAAGAAG CGCAACAGTG TCTCGCTGAA CTTTGCCATC CGGCCCGGGG AATGTTGCCT   1320

GATCATATCA GCAGCCAGTT TGCGCGTTTA AAAGCGCTTA CCTTCCCCGC GTGGGAGGAG   1380

AATATTCAGT GTAACAGGGA TGGTATAAAT CAGTTTTGTA TTCTGGATGC AGGCAGCAAG   1440

GAGATATTGT CAATCACTCT TGATGATGCC GGGAACTATA CCGTGAATTG TCAGGGGTAC   1500

AGTGAAGCAC ATGACTTCAT CATGGACACA GAACCGGGAG AGGAATGCAC AGAATTCGCG   1560

GAGGGGGCAT CCGGGACATC CCTCCGCCCT GCCACAACGG TTTCACAGAA GGCAGCAGAG   1620

TATGATGCTG TCTGGTCAAA TGGGAAAGGG ATGCACCAGC AGGAGAGTCA CCCGGCCGCG   1680

CAGCAGTGGT ACAGGAAATG CGTGATTGCC TGAATAACGG CAATCCAGTG CTTAACGTGG   1740

GAGCGTCAGG TCTTACCACC TTACCAGACC GTTTACCACC GCATATTACA ACACTGGTTA   1800

TTCCTGATAA TAATCTGACC AGCCTGCCGG AGTTGCCGGA AGGACTACGG AGCTGGAGG   1860

TCTCTGGTAA CCTACAACTG ACCAGCCTGC CATCGCTGCC GCAGGGACTA CAGAAGCTGT   1920

GGGCCTATAA TAATTGGCTG CCAGCCTGC CGACGTTGCC GCCAGGACTA GGGGATCTGG   1980

CGGTCTCTAA TAACCAGCTG ACCAGCCTGC CGGAGATGCC GCCAGCACTA CGGGAGCTGA   2040

GGGTCTCTGG TAACAACCTG ACCAGCTGCG CGCGCTGCCG TCAGGACTAC AGAAGCTGTG   2100

GGCCTATAAT AATCGGCTGA CCAGCCTGCC GGAGATGTCG CCAGGACTAC AGGAGCTGGA   2160

TGCGTGATTG CCTGAATAAC GGCAATCCAG TGCTTAACGT GGGAGCGTCA GGTCTTACCA   2220

CCTTACCAGA CCGTTTACCA CCGCATATTA CAACACTGGT TATTCCTGAT AATAATCTGA   2280

CCAGCCTGCC GGAGTTGCCG AAGGACTACG GGAGCTGGA GGTCTCTGGT AACCTACAAC   2340

TGACCAGCCT GCCATCGCTG CCGCAGGGAC TACAGAAGCT GTGGGCCTAT AATAATTGGC   2400

TGGCCAGCCT GCCGACGTTG CCGCCAGGAC TAGGGGATCT GGCGGTCTCT AATAACCAGC   2460

TGACCAGCCT GCCGGAGATG CCGCCAGCAC TACGGGAGCT GAGGGTCTCT GGTAACAACC   2520

TGACCAGCTG CGCGCGCTGC CGTCAGGACT ACAGAAGCTG TGGGCCTATA ATAATCGGCT   2580

GACCAGCCTG CCGGAGATGT CGCCAGGACT ACAGGAGCTG GATGTCTCTC ATAACCAGCT   2640

GACCCGCCTG CCGCAAAGCC TCACGGGTCT GTCTTCAGCG GCACGCGTAT ATCTGGACGG   2700

GAATCCACTG TCTGTACGCA CTCGTGACAG GCTCTGCGGA CATCATTGGC CATTCAGGCA   2760

TCAGGATACA CTTCGATATG GCGGGGCCTT CCGTCCCCGG GAAGCCCGGG CACTGCACCT   2820
```

```
GGCGGTCGCT GACTGGCTGA CGTCTGCACG GGAGGGGGAA GCGGCCCAGG CAGACAGATG      2880

GCAGGCGTTC GGACTGGAAG ATAACGCCGC CGCCTTCAGC CTGGTCCTGG ACAGACTGCG      2940

TGAGACGGAA AACTTCAAAA AAGACGCGGG CTTTAAGGCA CAGATATCAT CCTGGCTGAC      3000

ACAACTGGCT GAAGATGCTG CGCTGAGAGC AAAAACCTTT GCCATGGCAA CAGAGGCAAC      3060

ATCAACCTGC GAGGACCGGG TCACACATGC CCTGCACCAG ATGAATAACG TACAACTGGT      3120

ACATAATGCA GAAAAGGGG AATACGACAA CAATCTCCAG GGGCTGGTTT CCACGGGGCG       3180

TGAGATGTTC CGCCTGGCAA CACTGGAACA GATTGCCCGG GAAAAAGCCG AACACTGGC       3240

TTTAGTCGAT GACGTTGAGG TCTATCTGGC GTTCCAGAAT AAGCTGAAGG AATCACTTGA      3300

GCTGACCAGC GTGACGTCAG AAATGCGTTT CTTTGACGTT TCCGGCGTGA CGGTTTCAGA      3360

CCTTCAGGCT GCGGACGTTC AGGTGAAAAC CGCTGAAAAC AGCGGGTTCA GTAAATGGAT      3420

ACTGCAGTGG GGGCCGTTAC ACAGCGTGCT GGAACGCAAA GTGCCGGAAC GCTTTAACGC      3480

GCTTCGTGAA AAGCAAATAT CGGATTATGA AGACACGTAC CGGAAGCTGT ATGACGAAGT      3540

GCTGAAATCG TCCGGGCTGG TCGACGATAC CGATGCAGAA CGTACTATCG GAGTAAGTGC      3600

GATGGATAGT GCGAAAAAAG AATTTCTGGA TGGCCTGCGC GCTCTTGTGG ATGAGGTGCT      3660

GGGTAGCTAT CTGACAGCCC GGTGGCGTCT TAACTGAGCA CGATATTCTC CGCACCAGGC      3720

GAATGTGGTG CGGTGAACAA AGATATTCCT TGGACAAACA ACATGAGACA GCACTGATGA      3780

TGCACAGGTG AAACAGGGGA GACTTCTTCA GTCAGGGCGT ACGCAACTCA ACCTTTTCGA      3840

CGATACGCGC C                                                          3851

(2) INFORMATION FOR SEQ ID NO:17:

(i) SEQUENCE CHARACTERISTICS:
        (A) LENGTH: 15 base pairs
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:17:

CCAGGTGGAT ACGGA                                                        15

(2) INFORMATION FOR SEQ ID NO:18:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:18:

TAGCGTCCTC CCCATGTGCG                                                   20

(2) INFORMATION FOR SEQ ID NO:19:

(i) SEQUENCE CHARACTERISTICS:
        (A) LENGTH: 18 base pairs
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:19:
```

-continued

```
CCGGCGCTAC TGGCGGCG                                              18

(2) INFORMATION FOR SEQ ID NO:20:

(i) SEQUENCE CHARACTERISTICS:
        (A) LENGTH: 18 base pairs
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:20:

AGCGTTTCAA CAGCCCCG                                              18

(2) INFORMATION FOR SEQ ID NO:21:

(i) SEQUENCE CHARACTERISTICS:
        (A) LENGTH: 17 base pairs
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:21:

CGGGGCTGTT GAAACGC                                               17

(2) INFORMATION FOR SEQ ID NO:22:

(i) SEQUENCE CHARACTERISTICS:
        (A) LENGTH: 16 base pairs
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:22:

AACCTGGCCT TTTCAG                                                16

(2) INFORMATION FOR SEQ ID NO:23:

(i) SEQUENCE CHARACTERISTICS:
        (A) LENGTH: 19 base pairs
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:23:

GGCAGGGAGC CTTGCTTGG                                             19

(2) INFORMATION FOR SEQ ID NO:24:

(i) SEQUENCE CHARACTERISTICS:
        (A) LENGTH: 19 base pairs
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:24:

GTGCCTGGCC AGTTCTCCA                                             19

(2) INFORMATION FOR SEQ ID NO:25:
```

(i) SEQUENCE CHARACTERISTICS:
            (A) LENGTH: 26 base pairs
            (B) TYPE: nucleic acid
            (C) STRANDEDNESS: double
            (D) TOPOLOGY: linear (ii) MOLECULE TYPE: Genomic DNA (xi) SEQUENCE DESCRIPTION: SEQ ID NO:25:

CGCGGATCCA TTATGGGATG TATCGG                                              26

(2) INFORMATION FOR SEQ ID NO:26:

(i) SEQUENCE CHARACTERISTICS:
            (A) LENGTH: 20 base pairs
            (B) TYPE: nucleic acid
            (C) STRANDEDNESS: double
            (D) TOPOLOGY: linear (ii) MOLECULE TYPE: Genomic DNA (xi) SEQUENCE DESCRIPTION: SEQ ID NO:26:

CCGGCAGCAA AATGTTGCAG                                                     20

(2) INFORMATION FOR SEQ ID NO:27:

(i) SEQUENCE CHARACTERISTICS:
            (A) LENGTH: 12 amino acids
            (B) TYPE: amino acid
            (D) TOPOLOGY: linear (ii) MOLECULE TYPE: peptide (xi) SEQUENCE DESCRIPTION: SEQ ID NO:27:

Val Thr Ser Val Arg Thr Gln Pro Pro Val Ile Met
 1               5                  10

(2) INFORMATION FOR SEQ ID NO:28:

(i) SEQUENCE CHARACTERISTICS:
            (A) LENGTH: 15 amino acids
            (B) TYPE: amino acid
            (D) TOPOLOGY: linear (ii) MOLECULE TYPE: peptide (xi) SEQUENCE DESCRIPTION: SEQ ID NO:28:

Met Leu Ile Ser Asn Val Gly Ile Asn Pro Ala Ala Tyr Leu Asn
 1               5                  10                  15

(2) INFORMATION FOR SEQ ID NO:29:

(i) SEQUENCE CHARACTERISTICS:
            (A) LENGTH: 13 amino acids
            (B) TYPE: amino acid
            (D) TOPOLOGY: linear (ii) MOLECULE TYPE: peptide (xi) SEQUENCE DESCRIPTION: SEQ ID NO:29:

Met Asn Asn Leu Thr Leu Ser Xaa Phe Xaa Lys Val Gly
 1               5                  10

(2) INFORMATION FOR SEQ ID NO:30:

(i) SEQUENCE CHARACTERISTICS:
            (A) LENGTH: 15 amino acids
            (B) TYPE: amino acid

```
           (D) TOPOLOGY: linear (ii) MOLECULE TYPE: peptide (xi) SEQUENCE DESCRIPTION: SEQ ID NO:30:

Met Leu Ile Ser Asn Val Gly Ile Asn Pro Ala Ala Tyr Leu Asn
 1               5                  10                  15

(2) INFORMATION FOR SEQ ID NO:31:

(i) SEQUENCE CHARACTERISTICS:
           (A) LENGTH: 12 amino acids
           (B) TYPE: amino acid
           (D) TOPOLOGY: linear (ii) MOLECULE TYPE: peptide (xi) SEQUENCE DESCRIPTION: SEQ ID NO:31:

Thr Lys Ile Thr Leu Ser Pro Gln Asn Phe Phe Ile
 1               5                  10

(2) INFORMATION FOR SEQ ID NO:32:

(i) SEQUENCE CHARACTERISTICS:
           (A) LENGTH: 80 amino acids
           (B) TYPE: amino acid
           (D) TOPOLOGY: linear (ii) MOLECULE TYPE: peptide (xi) SEQUENCE DESCRIPTION: SEQ ID NO:32:

Met Ala Thr Pro Trp Ser Gly Tyr Leu Asp Val Ser Ala Lys Phe
 1               5                  10                  15

Asp Thr Gly Val Asp Asn Leu Gln Thr Gln Val Thr Glu Ala Leu Asp
                20                  25                  30

Lys Leu Ala Ala Lys Pro Ser Asp Pro Ala Leu Leu Ala Ala Tyr Gln
         35                  40                  45

Ser Lys Leu Ser Glu Tyr Asn Leu Tyr Arg Asn Ala Gln Ser Asn Thr
     50                  55                  60

Val Lys Val Phe Lys Asp Ile Asp Ala Ala Ile Ile Gln Asn Phe Arg
 65                  70                  75                  80

(2) INFORMATION FOR SEQ ID NO:33:

(i) SEQUENCE CHARACTERISTICS:
           (A) LENGTH: 83 amino acids
           (B) TYPE: amino acid
           (D) TOPOLOGY: linear (ii) MOLECULE TYPE: peptide (xi) SEQUENCE DESCRIPTION: SEQ ID NO:33:

Met Ser Val Thr Val Pro Asn Asp Asp Trp Thr Leu Ser Ser Leu Ser
 1               5                  10                  15

Glu Thr Phe Asp Asp Gly Thr Gln Thr Leu Gln Gly Glu Leu Thr Leu
                20                  25                  30

Ala Leu Asp Lys Leu Ala Lys Asn Pro Ser Asn Pro Gln Leu Leu Ala
         35                  40                  45

Glu Tyr Gln Ser Lys Leu Ser Glu Tyr Thr Leu Tyr Arg Asn Ala Gln
     50                  55                  60

Ser Asn Thr Val Lys Val Ile Lys Asp Val Asp Ala Ala Ile Ile Gln
 65                  70                  75                  80

Asn Phe Arg
```

(2) INFORMATION FOR SEQ ID NO:34:

(i) SEQUENCE CHARACTERISTICS:
        (A) LENGTH: 87 amino acids
        (B) TYPE: amino acid
        (D) TOPOLOGY: linear (ii) MOLECULE TYPE: peptide (xi) SEQUENCE DESCRIPTION: SEQ ID NO:34:

```
Met Ser Asn Phe Ser Gly Phe Thr Lys Gly Asn Asp Ile Ala Asp Leu
 1               5                  10                  15

Asp Ala Val Ala Gln Thr Leu Lys Lys Pro Ala Asp Asp Ala Asn Lys
            20                  25                  30

Ala Val Asn Asp Ser Ile Ala Ala Leu Lys Asp Thr Pro Asp Asn Pro
        35                  40                  45

Ala Leu Leu Ala Asp Leu Gln His Ser Ile Asn Lys Trp Ser Val Ile
    50                  55                  60

Tyr Asn Ile Ser Ser Thr Ile Val Arg Ser Met Lys Asp Leu Met Gln
65                  70                  75                  80

Gly Ile Leu Gln Lys Phe Pro
                85
```

(2) INFORMATION FOR SEQ ID NO:35:

(i) SEQUENCE CHARACTERISTICS:
        (A) LENGTH: 101 amino acids
        (B) TYPE: amino acid
        (D) TOPOLOGY: linear (ii) MOLECULE TYPE: peptide (xi) SEQUENCE DESCRIPTION: SEQ ID NO:35:

```
Met Ser Ile Ala Thr Ile Val Pro Glu Asn Ala Val Ile Gly Gln Ala
 1               5                  10                  15

Val Asn Ile Arg Ser Met Glu Thr Asp Ile Val Ser Leu Asp Asp Arg
            20                  25                  30

Leu Leu Gln Ala Phe Ser Gly Ser Ala Ile Ala Thr Ala Val Asp Lys
        35                  40                  45

Gln Thr Ile Thr Asn Arg Ile Glu Asp Pro Asn Leu Val Thr Asp Pro
    50                  55                  60

Lys Glu Leu Ala Ile Ser Gln Glu Met Ile Ser Asp Tyr Asn Leu Tyr
65                  70                  75                  80

Val Ser Met Val Ser Thr Leu Thr Arg Lys Gly Val Gly Ala Val Glu
                85                  90                  95

Thr Leu Leu Arg Ser
            100
```

(2) INFORMATION FOR SEQ ID NO:36:

(i) SEQUENCE CHARACTERISTICS:
        (A) LENGTH: 97 amino acids
        (B) TYPE: amino acid
        (D) TOPOLOGY: linear (ii) MOLECULE TYPE: peptide (xi) SEQUENCE DESCRIPTION: SEQ ID NO:36:

```
Met Asn Tyr Ile Tyr Pro Val Asn Gln Val Asp Ile Ile Lys Ala Ser
 1               5                  10                  15
```

```
Asp Phe Gln Ser Gln Glu Ile Ser Ser Leu Glu Asp Val Val Ser Ala
                20                  25                  30

Lys Tyr Ser Asp Ile Lys Met Asp Thr Asp Ile Gln Val Ser Gln Ile
            35                  40                  45

Met Glu Met Val Ser Asn Pro Glu Ser Leu Asn Pro Glu Ser Leu Ala
     50                  55                  60

Lys Leu Gln Thr Thr Leu Ser Asn Tyr Ser Ile Gly Val Ser Leu Ala
 65                  70                  75                  80

Gly Thr Leu Ala Arg Lys Thr Val Ser Ala Val Glu Thr Leu Leu Lys
                85                  90                  95

Ser
```

(2) INFORMATION FOR SEQ ID NO:37:

(i) SEQUENCE CHARACTERISTICS:
        (A) LENGTH: 241 amino acids
        (B) TYPE: amino acid
        (D) TOPOLOGY: linear (ii) MOLECULE TYPE: peptide (xi) SEQUENCE DESCRIPTION: SEQ ID NO:37:

```
Met Ile Arg Tyr Lys Gly Phe Ile Leu Phe Leu Leu Met Leu Ile
 1               5                  10                  15

Gly Cys Glu Gln Arg Glu Leu Ile Ser Asn Leu Ser Gln Arg Gln
                20                  25                  30

Ala Asn Glu Ile Ile Ser Val Leu Glu Arg His Asn Ile Thr Ala Arg
            35                  40                  45

Lys Val Asp Gly Gly Lys Gln Gly Ile Ser Val Gln Val Glu Lys Gly
     50                  55                  60

Thr Phe Ala Ser Ala Val Asp Leu Met Arg Met Tyr Asp Leu Pro Asn
 65                  70                  75                  80

Pro Glu Arg Val Asp Ile Ser Gln Met Phe Pro Thr Asp Ser Leu Val
                85                  90                  95

Ser Ser Pro Arg Ala Glu Lys Ala Arg Leu Tyr Ser Ala Ile Glu Gln
                100                 105                 110

Arg Leu Glu Gln Ser Leu Val Ser Ile Gly Gly Val Ile Ser Ala Lys
            115                 120                 125

Ile His Val Ser Tyr Asp Leu Glu Glu Lys Asn Ile Ser Ser Lys Pro
 130                 135                 140

Met His Ile Ser Val Ile Ala Ile Tyr Asp Ser Pro Lys Glu Ser Glu
 145                 150                 155                 160

Leu Leu Val Ser Asn Ile Lys Arg Phe Leu Lys Asn Thr Phe Ser Asp
                165                 170                 175

Val Lys Tyr Glu Asn Ile Ser Val Ile Leu Thr Pro Lys Glu Glu Tyr
            180                 185                 190

Val Tyr Thr Asn Val Gln Pro Val Lys Glu Val Lys Ser Glu Phe Leu
     195                 200                 205

Thr Asn Glu Val Ile Tyr Leu Phe Leu Gly Met Ala Val Leu Val Val
     210                 215                 220

Ile Leu Leu Val Trp Ala Phe Lys Thr Gly Trp Phe Lys Arg Asn Lys
 225                 230                 235                 240

Ile
```

(2) INFORMATION FOR SEQ ID NO:38:

```
    (i) SEQUENCE CHARACTERISTICS:
        (A) LENGTH: 244 amino acids
        (B) TYPE: amino acid
        (D) TOPOLOGY: linear (ii) MOLECULE TYPE: peptide (xi) SEQUENCE DESCRIPTION: SEQ ID NO:38:

Met Lys Val Lys Thr Ser Leu Ser Thr Leu Ile Leu Ile Leu Phe Leu
  1               5                  10                  15

Thr Gly Cys Lys Val Asp Leu Tyr Thr Gly Ile Ser Gln Lys Glu Gly
                 20                  25                  30

Asn Glu Met Leu Ala Leu Leu Arg Gln Glu Gly Leu Ser Ala Asp Lys
             35                  40                  45

Glu Pro Asp Lys Asp Gly Lys Ile Lys Leu Leu Val Glu Gly Ser Asp
 50                  55                  60

Val Ala Gln Ala Ile Asp Ile Leu Lys Arg Lys Gly Tyr Pro His Glu
 65                  70                  75                  80

Ser Phe Ser Thr Leu Gln Asp Val Phe Pro Lys Asp Gly Leu Ile Ser
                 85                  90                  95

Ser Pro Ile Glu Glu Leu Ala Arg Leu Asn Tyr Ala Lys Ala Gln Glu
                100                 105                 110

Ile Ser Arg Thr Leu Ser Glu Ile Asp Gly Val Leu Val Ala Arg Val
            115                 120                 125

His Val Val Leu Pro Glu Glu Gln Asn Asn Lys Gly Lys Lys Gly Val
130                 135                 140

Ala Ala Ser Ala Ser Val Phe Ile Lys His Ala Ala Asp Ile Gln Phe
145                 150                 155                 160

Asp Thr Tyr Ile Pro Gln Ile Lys Gln Leu Val Asn Asn Ser Ile Glu
                165                 170                 175

Gly Leu Ala Tyr Asp Arg Ile Ser Val Ile Leu Val Pro Ser Val Asp
            180                 185                 190

Val Arg Gln Ser Ser His Leu Pro Arg Asn Thr Ser Ile Leu Ser Ile
            195                 200                 205

Gln Val Ser Glu Glu Ser Lys Gly Arg Leu Ile Gly Leu Leu Ser Leu
    210                 215                 220

Leu Ile Leu Leu Leu Pro Val Thr Asn Leu Ala Gln Tyr Phe Trp Leu
225                 230                 235                 240

Gln Arg Lys Lys (2) INFORMATION FOR SEQ ID NO:39:

(i) SEQUENCE CHARACTERISTICS:
        (A) LENGTH: 252 amino acids
        (B) TYPE: amino acid
        (D) TOPOLOGY: linear (ii) MOLECULE TYPE: peptide (xi) SEQUENCE DESCRIPTION: SEQ ID NO:39:

Met Ile Arg Arg Tyr Leu Tyr Thr Phe Leu Leu Val Met Thr Leu Ala
  1               5                  10                  15

Gly Cys Lys Asp Lys Asp Leu Leu Lys Gly Leu Asp Gln Glu Gln Ala
                 20                  25                  30

Asn Glu Val Ile Ala Val Leu Gln Met His Asn Ile Glu Ala Asn Lys
             35                  40                  45

Ile Asp Ser Gly Lys Leu Gly Tyr Ser Ile Thr Val Ala Glu Pro Asp
 50                  55                  60
```

```
Phe Thr Ala Ala Val Tyr Trp Ile Lys Thr Tyr Gln Leu Pro Pro Arg
 65                  70                  75                  80

Pro Arg Val Glu Ile Ala Gln Met Phe Pro Ala Asp Ser Leu Val Ser
                 85                  90                  95

Ser Pro Arg Ala Glu Lys Ala Arg Leu Tyr Ser Ala Ile Glu Gln Arg
            100                 105                 110

Leu Glu Gln Ser Leu Gln Thr Met Gly Val Leu Ser Ala Arg Val
        115                 120                 125

His Ile Ser Tyr Asp Ile Asp Ala Gly Glu Asn Gly Arg Pro Pro Lys
        130                 135                 140

Pro Val His Leu Ser Ala Leu Ala Val Tyr Glu Arg Gly Ser Pro Leu
145                 150                 155                 160

Ala His Gln Ile Ser Asp Ile Lys Arg Phe Leu Lys Asn Ser Phe Ala
                165                 170                 175

Asp Val Asp Tyr Asp Asn Ile Ser Val Val Leu Ser Glu Arg Ser Asp
            180                 185                 190

Ala Gln Leu Gln Ala Pro Gly Thr Pro Val Lys Arg Asn Ser Phe Ala
        195                 200                 205

Thr Ser Trp Ile Val Leu Ile Ile Leu Leu Ser Val Met Ser Ala Gly
210                 215                 220

Phe Gly Val Trp Tyr Tyr Lys Asn His Tyr Ala Arg Asn Lys Lys Gly
225                 230                 235                 240

Ile Thr Ala Asp Asp Lys Ala Lys Ser Ser Asn Glu
                245                 250
```

(2) INFORMATION FOR SEQ ID NO:40:

(i) SEQUENCE CHARACTERISTICS:
        (A) LENGTH: 289 amino acids
        (B) TYPE: amino acid
        (D) TOPOLOGY: linear (ii) MOLECULE TYPE: peptide (xi) SEQUENCE DESCRIPTION: SEQ ID NO:40:

```
Arg Lys Ala Glu Glu Thr Asn Arg Ile Met Gly Cys Ile Gly Lys Val
 1               5                  10                  15

Leu Gly Ala Leu Leu Thr Ile Val Ser Val Val Ala Ala Val Phe Thr
                 20                  25                  30

Gly Gly Ala Ser Leu Ala Leu Ala Ala Val Gly Leu Ala Val Met Val
            35                  40                  45

Ala Asp Glu Ile Val Lys Ala Ala Thr Gly Val Ser Phe Ile Gln Gln
 50                  55                  60

Ala Leu Asn Pro Ile Met Glu His Val Leu Lys Pro Leu Met Glu Leu
 65                  70                  75                  80

Ile Gly Lys Ala Ile Thr Lys Ala Leu Glu Gly Leu Gly Val Asp Lys
                 85                  90                  95

Lys Thr Ala Glu Met Ala Gly Ser Ile Val Gly Ala Ile Val Ala Ala
            100                 105                 110

Ile Ala Met Val Ala Val Ile Val Val Ala Val Val Gly Lys Gly
        115                 120                 125

Ala Ala Ala Lys Leu Gly Asn Ala Leu Ser Lys Met Met Gly Glu Thr
        130                 135                 140

Ile Lys Lys Leu Val Pro Asn Val Leu Lys Gln Leu Ala Gln Asn Gly
145                 150                 155                 160
```

```
Ser Lys Leu Phe Thr Gln Gly Met Gln Arg Ile Thr Ser Gly Leu Gly
                165                 170                 175

Asn Val Gly Ser Lys Met Gly Leu Gln Thr Asn Ala Leu Ser Lys Glu
            180                 185                 190

Leu Val Gly Asn Thr Leu Asn Lys Val Ala Leu Gly Met Glu Val Thr
        195                 200                 205

Asn Thr Ala Ala Gln Ser Ala Gly Gly Val Ala Glu Gly Val Phe Ile
    210                 215                 220

Lys Asn Ala Ser Glu Ala Leu Ala Asp Phe Met Leu Ala Arg Phe Ala
225                 230                 235                 240

Met Asp Gln Ile Gln Gln Trp Leu Lys Gln Ser Val Glu Ile Phe Gly
                245                 250                 255

Glu Asn Gln Lys Val Thr Ala Glu Leu Gln Lys Ala Met Ser Ser Ala
            260                 265                 270

Val Gln Gln Asn Ala Asp Ala Ser Arg Phe Ile Leu Arg Gln Ser Arg
        275                 280                 285

Ala
```

(2) INFORMATION FOR SEQ ID NO:41:

(i) SEQUENCE CHARACTERISTICS:
        (A) LENGTH: 283 amino acids
        (B) TYPE: amino acid
        (D) TOPOLOGY: linear (ii) MOLECULE TYPE: peptide (xi) SEQUENCE DESCRIPTION: SEQ ID NO:41:

```
Arg Lys Ala Glu Glu Leu Asn Arg Val Met Gly Cys Val Gly Lys Ile
1               5                   10                  15

Leu Gly Ala Leu Leu Thr Ile Val Ser Val Ala Ala Ala Phe Ser
            20                  25                  30

Gly Gly Ala Ser Leu Ala Leu Ala Ala Val Gly Leu Ala Leu Met Val
        35                  40                  45

Thr Asp Ala Ile Val Gln Ala Ala Thr Gly Asn Ser Phe Met Glu Gln
    50                  55                  60

Ala Leu Asn Pro Ile Met Lys Ala Val Ile Glu Pro Leu Ile Lys Leu
65                  70                  75                  80

Leu Ser Asp Ala Phe Thr Lys Met Leu Glu Gly Leu Gly Val Asp Ser
                85                  90                  95

Lys Lys Ala Lys Met Ile Gly Ser Ile Leu Gly Ala Ile Ala Gly Ala
            100                 105                 110

Leu Val Leu Val Ala Ala Val Val Leu Val Ala Thr Val Gly Lys Gln
        115                 120                 125

Ala Ala Ala Lys Leu Ala Glu Asn Ile Gly Lys Ile Ile Gly Lys Thr
    130                 135                 140

Leu Thr Asp Leu Ile Pro Lys Phe Leu Lys Asn Phe Ser Ser Gln Leu
145                 150                 155                 160

Asp Asp Leu Ile Thr Asn Ala Val Ala Arg Leu Asn Lys Phe Leu Gly
                165                 170                 175

Ala Ala Gly Asp Glu Val Ile Ser Lys Gln Ile Ile Ser Thr His Leu
            180                 185                 190

Asn Gln Ala Val Leu Leu Gly Glu Ser Val Asn Ser Ala Thr Gln Ala
        195                 200                 205

Gly Gly Ser Val Ala Ser Ala Val Phe Gln Asn Ser Ala Ser Thr Asn
    210                 215                 220
```

```
Leu Ala Asp Leu Thr Leu Ser Lys Tyr Gln Val Glu Gln Leu Ser Lys
225                 230                 235                 240

Tyr Ile Ser Glu Ala Ile Glu Lys Phe Gly Gln Leu Gln Glu Val Ile
                245                 250                 255

Ala Asp Leu Leu Ala Ser Met Ser Asn Ser Gln Ala Asn Arg Thr Asp
                260                 265                 270

Val Ala Lys Ala Ile Leu Gln Gln Thr Thr Ala
                275                 280

(2) INFORMATION FOR SEQ ID NO:42:

(i) SEQUENCE CHARACTERISTICS:
        (A) LENGTH: 409 amino acids
        (B) TYPE: amino acid
        (D) TOPOLOGY: linear (ii) MOLECULE TYPE: peptide (xi) SEQUENCE DESCRIPTION: SEQ ID NO:42:

Met Leu Ile Ser Asn Val Gly Ile Asn Pro Ala Ala Tyr Leu Asn Asn
1               5                   10                  15

His Ser Val Glu Asn Ser Ser Gln Thr Ala Ser Gln Ser Val Ser Ala
                20                  25                  30

Lys Asp Ile Leu Asn Ser Ile Gly Ile Ser Ser Lys Val Ser Asp
                35                  40                  45

Leu Gly Leu Ser Pro Thr Leu Ser Ala Pro Ala Pro Gly Val Leu Thr
            50                  55                  60

Gln Thr Pro Gly Thr Ile Thr Ser Phe Leu Lys Ala Ser Ile Gln Asn
65                      70                  75                  80

Thr Asp Met Asn Gln Asp Leu Asn Ala Leu Ala Asn Asn Val Thr Thr
                85                  90                  95

Lys Ala Asn Glu Val Val Gln Thr Gln Leu Arg Glu Gln Gln Ala Glu
                100                 105                 110

Val Gly Lys Phe Phe Asp Ile Ser Gly Met Ser Ser Ser Ala Val Ala
                115                 120                 125

Leu Leu Ala Ala Ala Asn Thr Leu Met Leu Thr Leu Asn Gln Ala Asp
                130                 135                 140

Ser Lys Leu Ser Gly Lys Leu Ser Leu Val Ser Phe Asp Ala Ala Lys
145                 150                 155                 160

Thr Thr Ala Ser Ser Met Met Arg Glu Gly Met Asn Ala Leu Ser Gly
                165                 170                 175

Ser Ile Ser Gln Ser Ala Leu Gln Leu Gly Ile Thr Gly Val Gly Ala
                180                 185                 190

Lys Leu Glu Tyr Lys Gly Leu Gln Asn Glu Arg Gly Ala Leu Lys His
                195                 200                 205

Asn Ala Ala Lys Ile Asp Lys Leu Thr Thr Glu Ser His Ser Ile Lys
                210                 215                 220

Asn Val Leu Asn Gly Gln Asn Ser Val Lys Leu Gly Ala Glu Gly Val
225                 230                 235                 240

Asp Ser Leu Lys Ser Leu Asn Met Lys Lys Thr Gly Thr Asp Ala Thr
                245                 250                 255

Lys Asn Leu Asn Asp Ala Thr Leu Lys Ser Asn Ala Gly Thr Ser Ala
                260                 265                 270

Thr Glu Ser Leu Gly Ile Lys Asp Ser Asn Lys Gln Ile Ser Pro Glu
                275                 280                 285
```

```
His Gln Ala Ile Leu Ser Lys Arg Leu Glu Ser Val Glu Ser Asp Ile
    290                 295                 300

Arg Leu Glu Gln Asn Thr Met Asp Met Thr Arg Ile Asp Ala Arg Lys
305                 310                 315                 320

Met Gln Met Thr Gly Asp Leu Ile Met Lys Asn Ser Val Thr Val Gly
                325                 330                 335

Gly Ile Ala Gly Ala Ser Gly Gln Tyr Ala Ala Thr Gln Glu Arg Ser
                340                 345                 350

Glu Gln Gln Ile Ser Gln Val Asn Asn Arg Val Ala Ser Thr Ala Ser
                355                 360                 365

Asp Glu Ala Arg Glu Ser Ser Arg Lys Ser Thr Ser Leu Ile Gln Glu
    370                 375                 380

Met Leu Lys Thr Met Glu Ser Ile Asn Gln Ser Lys Ala Ser Ala Leu
385                 390                 395                 400

Ala Ala Ile Ala Gly Asn Ile Arg Ala
                405
```

(2) INFORMATION FOR SEQ ID NO:43:

(i) SEQUENCE CHARACTERISTICS:
  (A) LENGTH: 382 amino acids
  (B) TYPE: amino acid
  (D) TOPOLOGY: linear (ii) MOLECULE TYPE: peptide (xi) SEQUENCE DESCRIPTION: SEQ ID NO:43:

```
Met Leu Gln Lys Gln Phe Cys Asn Lys Leu Leu Asp Thr Asn Lys
1               5                   10                  15

Glu Asn Val Met Glu Ile Gln Asn Thr Lys Pro Thr Gln Thr Leu Tyr
                20                  25                  30

Thr Asp Ile Ser Thr Lys Gln Thr Gln Ser Ser Ser Glu Thr Gln Lys
            35                  40                  45

Ser Gln Asn Tyr Gln Gln Ile Ala Ala His Ile Pro Leu Asn Val Gly
        50                  55                  60

Lys Asn Pro Val Leu Thr Thr Thr Leu Asn Asp Asp Gln Leu Leu Lys
65                  70                  75                  80

Leu Ser Glu Gln Val Gln His Asp Ser Glu Ile Ile Ala Arg Leu Thr
                85                  90                  95

Asp Lys Lys Met Lys Asp Leu Ser Glu Met Ser His Thr Leu Thr Pro
                100                 105                 110

Glu Asn Thr Leu Asp Ile Ser Ser Leu Ser Ser Asn Ala Val Ser Leu
            115                 120                 125

Ile Ile Ser Val Ala Val Leu Leu Ser Ala Leu Arg Thr Ala Glu Thr
        130                 135                 140

Lys Leu Gly Ser Gln Leu Ser Leu Ile Ala Phe Asp Ala Thr Lys Ser
145                 150                 155                 160

Ala Ala Glu Asn Ile Val Arg Gln Gly Leu Ala Ala Leu Ser Ser Ser
                165                 170                 175

Ile Thr Gly Ala Val Thr Gln Val Gly Ile Thr Gly Ile Gly Ala Lys
                180                 185                 190

Lys Thr His Ser Gly Ile Ser Asp Gln Lys Gly Ala Leu Arg Lys Asn
            195                 200                 205

Leu Ala Thr Ala Gln Ser Leu Glu Lys Glu Leu Ala Gly Ser Lys Leu
        210                 215                 220

Gly Leu Asn Lys Gln Ile Asp Thr Asn Ile Thr Ser Pro Gln Thr Asn
```

-continued

```
                225                 230                 235                 240
Ser Ser Thr Lys Phe Leu Gly Lys Asn Lys Leu Ala Pro Asp Asn Ile
                245                 250                 255

Ser Leu Ser Thr Glu His Lys Thr Ser Leu Ser Ser Pro Asp Ile Ser
                260                 265                 270

Leu Gln Asp Lys Ile Asp Thr Gln Arg Arg Thr Tyr Glu Leu Asn Thr
                275                 280                 285

Leu Ser Ala Gln Gln Lys Gln Asn Ile Gly Arg Ala Thr Met Glu Thr
                290                 295                 300

Ser Ala Val Ala Gly Asn Ile Ser Thr Ser Gly Gly Arg Tyr Ala Ser
305                 310                 315                 320

Ala Leu Glu Glu Glu Glu Gln Leu Ile Ser Gln Ala Ser Ser Lys Gln
                325                 330                 335

Ala Glu Glu Ala Ser Gln Val Ser Lys Glu Ala Ser Gln Ala Thr Asn
                340                 345                 350

Gln Leu Ile Gln Lys Leu Leu Asn Ile Ile Asp Ser Ile Asn Gln Ser
                355                 360                 365

Lys Asn Ser Ala Ala Ser Gln Ile Ala Gly Asn Ile Arg Ala
370                 375                 380

(2) INFORMATION FOR SEQ ID NO:44:

(i) SEQUENCE CHARACTERISTICS:
        (A) LENGTH: 343 amino acids
        (B) TYPE: amino acid
        (D) TOPOLOGY: linear (ii) MOLECULE TYPE: peptide (xi) SEQUENCE DESCRIPTION: SEQ ID NO:44:

Met Leu Asn Ile Gln Asn Tyr Ser Ala Ser Pro His Pro Gly Ile Val
1               5                   10                  15

Ala Glu Arg Pro Gln Thr Pro Ser Ala Ser Glu His Val Glu Thr Ala
                20                  25                  30

Val Val Pro Ser Thr Thr Glu His Arg Gly Thr Asp Ile Ile Ser Leu
                35                  40                  45

Ser Gln Ala Ala Thr Lys Ile His Gln Ala Gln Gln Thr Leu Gln Ser
            50                  55                  60

Thr Pro Pro Ile Ser Glu Glu Asn Asn Asp Glu Arg Thr Leu Ala Arg
65                  70                  75                  80

Gln Gln Leu Thr Ser Ser Leu Asn Ala Leu Ala Lys Ser Gly Val Ser
                85                  90                  95

Leu Ser Ala Glu Gln Asn Glu Asn Leu Arg Ser Ala Phe Ser Ala Pro
                100                 105                 110

Thr Ser Ala Leu Phe Ser Ala Ser Pro Met Ala Gln Pro Arg Thr Thr
                115                 120                 125

Ile Ser Asp Ala Glu Ile Trp Asp Met Val Ser Gln Asn Ile Ser Ala
                130                 135                 140

Ile Gly Asp Ser Tyr Leu Gly Val Tyr Glu Asn Val Ala Val Tyr
145                 150                 155                 160

Thr Asp Phe Tyr Gln Ala Phe Ser Asp Ile Leu Ser Lys Met Gly Gly
                165                 170                 175

Trp Leu Leu Pro Gly Lys Asp Gly Asn Thr Val Lys Leu Asp Val Thr
                180                 185                 190

Ser Leu Lys Asn Asp Leu Asn Ser Leu Val Asn Lys Tyr Asn Gln Ile
                195                 200                 205
```

```
Asn Ser Asn Thr Val Leu Phe Pro Ala Gln Ser Gly Ser Gly Val Lys
    210                 215                 220

Val Ala Thr Glu Ala Glu Ala Arg Gln Trp Leu Ser Glu Leu Asn Leu
225                 230                 235                 240

Pro Asn Ser Cys Leu Lys Ser Tyr Gly Ser Gly Tyr Val Val Thr Val
                245                 250                 255

Asp Leu Thr Pro Leu Gln Lys Met Val Gln Asp Ile Asp Gly Leu Gly
                260                 265                 270

Ala Pro Gly Lys Asp Ser Lys Leu Glu Met Asp Asn Ala Lys Tyr Gln
            275                 280                 285

Ala Trp Gln Ser Gly Phe Lys Ala Gln Glu Glu Asn Met Lys Thr Thr
290                 295                 300

Leu Gln Thr Leu Thr Gln Lys Tyr Ser Asn Ala Asn Ser Leu Tyr Asp
305                 310                 315                 320

Asn Leu Val Lys Val Leu Ser Ser Thr Ile Ser Ser Ser Leu Glu Thr
                325                 330                 335

Ala Lys Ser Phe Leu Gln Gly
            340

(2) INFORMATION FOR SEQ ID NO:45:

(i) SEQUENCE CHARACTERISTICS:
        (A) LENGTH: 332 amino acids
        (B) TYPE: amino acid
        (D) TOPOLOGY: linear (ii) MOLECULE TYPE: peptide (xi) SEQUENCE DESCRIPTION: SEQ ID NO:45:

Met Asn Ile Thr Thr Leu Thr Asn Ser Ile Ser Thr Ser Ser Phe Ser
1               5                   10                  15

Pro Asn Asn Thr Asn Gly Ser Ser Thr Glu Thr Val Asn Ser Asp Ile
                20                  25                  30

Lys Thr Thr Thr Ser Ser His Pro Val Ser Ser Leu Thr Met Leu Asn
            35                  40                  45

Asp Thr Leu His Asn Ile Arg Thr Thr Asn Gln Ala Leu Lys Lys Glu
    50                  55                  60

Leu Ser Gln Lys Thr Leu Thr Lys Thr Ser Leu Glu Glu Ile Ala Leu
65                  70                  75                  80

His Ser Ser Gln Ile Ser Met Asp Val Asn Lys Ser Ala Gln Leu Leu
                85                  90                  95

Asp Ile Leu Ser Arg Asn Glu Tyr Pro Ile Asn Lys Asp Ala Arg Glu
                100                 105                 110

Leu Leu His Ser Ala Pro Lys Glu Ala Glu Leu Asp Gly Asp Gln Met
            115                 120                 125

Ile Ser His Arg Glu Leu Trp Ala Lys Ile Ala Asn Ser Ile Asn Asp
    130                 135                 140

Ile Asn Glu Gln Tyr Leu Lys Val Tyr Glu His Ala Val Ser Ser Tyr
145                 150                 155                 160

Thr Gln Met Tyr Gln Asp Phe Ser Ala Val Leu Ser Ser Leu Ala Gly
                165                 170                 175

Trp Ile Ser Pro Gly Gly Asn Asp Gly Asn Ser Val Lys Leu Gln Val
                180                 185                 190

Asn Ser Leu Lys Lys Ala Leu Glu Glu Leu Lys Glu Lys Tyr Lys Asp
            195                 200                 205
```

-continued

```
Lys Pro Leu Tyr Pro Ala Asn Asn Thr Val Ser Gln Glu Gln Ala Asn
    210                 215                 220

Lys Trp Leu Thr Glu Leu Gly Gly Thr Ile Gly Lys Val Ser Gln Lys
225                 230                 235                 240

Asn Gly Gly Tyr Val Val Ser Ile Asn Met Thr Pro Ile Asp Asn Met
                245                 250                 255

Leu Lys Ser Leu Asp Asn Leu Gly Gly Asn Gly Glu Val Val Leu Asp
                260                 265                 270

Asn Ala Lys Tyr Gln Ala Trp Asn Ala Gly Phe Ser Ala Glu Asp Glu
            275                 280                 285

Thr Met Lys Asn Asn Leu Gln Thr Leu Val Gln Lys Tyr Ser Asn Ala
    290                 295                 300

Asn Ser Ile Phe Asp Asn Leu Val Lys Val Leu Ser Ser Thr Ile Ser
305                 310                 315                 320

Ser Cys Thr Asp Thr Asp Lys Leu Phe Leu His Phe
                325                 330

(2) INFORMATION FOR SEQ ID NO:46:

(i) SEQUENCE CHARACTERISTICS:
        (A) LENGTH: 64 amino acids
        (B) TYPE: amino acid
        (D) TOPOLOGY: linear (ii) MOLECULE TYPE: peptide (xi) SEQUENCE DESCRIPTION: SEQ ID NO:46:

Met Val Thr Ser Val Arg Thr Gln Pro Pro Val Ile Met Pro Gly Met
1               5                   10                  15

Gln Thr Glu Ile Lys Thr Gln Ala Thr Asn Leu Ala Ala Asn Leu Ser
                20                  25                  30

Ala Val Arg Glu Ser Ala Thr Ala Thr Leu Ser Gly Glu Ile Lys Gly
            35                  40                  45

Pro Gln Leu Glu Asp Phe Pro Ala Leu Ile Lys Gln Ala Ser Leu Asp
    50                  55                  60

(2) INFORMATION FOR SEQ ID NO:47:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:47:

TAGACGACTA TAGCTCTTGC T                                        21
```

SALMONELLA SECRETED PROTEINS AND USES THEREOF

This is a continuation of International Patent Application No. PCT/US96/18504, with an international filing date of Nov. 14, 1996, and claims the benefit of prior U.S. provisional application No. 60/006,733, filed Nov. 14, 1995. +gi

STATEMENT AS TO FEDERALLY SPONSORED RESEARCH

This invention was made with Government support under AI34504 and AI30479 awarded by the National Institutes of Health. The Government has certain rights in the invention.

BACKGROUND OF THE INVENTION

The invention relates to virulence factors of *Salmonella typhimurium*.

*Salmonella typhimurium* (*S. typhimurium*) enter epithelial cells by a process termed bacterial-mediated endocytosis. *S. typhimurium* stimulates these normally nonphagocytic cells to undergo significant cytoskeletal rearrangements that are visualized as localized membrane ruffling adjacent to the bacteria. Bacteria are then internalized via membrane-bound vacuoles formed from the membrane ruffles.

Several *S. typhimurium* loci have been identified that are required for the induction of bacterial-mediated endocytosis (BME) by epithelial cells. Many of these epithelial-cell signaling loci have a similar chromosomal location, clustered within a 40 kb "virulence island" located between 59 and 60 minutes on the *S. typhimurium* chromosome (Mills et al., *Mol. Microbiol.* 15:749–759, 1995). InvJ is a *S. tymphimurium* gene which is thought to encode a secreted protein necessary for BME (Collazo et al., *Mol. Microbiol.* 15:25–38, 1995).

SUMMARY OF THE INVENTION

The invention features proteins involved in *Salmonella typhimurium* virulence and/or bacterial-mediated endocytosis. The genes encoding these proteins have now been cloned and their corresponding gene products characterized. Accordingly, the invention features a substantially pure DNA encoding a Salmonella secreted protein (Ssp). By the term "Salmonella secreted protein" is meant a Salmonella-derived protein, the secretion of which is dependent on the expression of PrgH. In preferred embodiments the invention features substantially pure DNA encoding a *Salmonella typhimurium* secreted protein. By *Salmonella typhimurium* secreted protein is meant as *Salmonella typhimurium* derived protein, the secretion of which is dependent on the expression of PrgH.

One aspect of the invention features a substantially pure DNA molecule which includes the SspB gene; preferably, the DNA includes the DNA sequence of SEQ ID NO: 1, or degenerate variants thereof encoding the amino acid sequence of SEQ ID NO: 5. In another aspect the invention features a substantially pure DNA molecule which includes the SspC gene; preferably, the DNA includes the DNA sequence of SEQ ID NO: 2, or degenerate variants thereof encoding the amino acid sequence of SEQ ID NO: 6. In another aspect the invention features a substantially pure DNA molecule which includes the SspD gene; preferably, the DNA includes the DNA sequence of SEQ ID NO: 3, or degenerate variants thereof encoding the amino acid sequence of SEQ ID NO: 7. In another aspect the invention features a substantially pure DNA molecule which included the SspA gene; preferably, the DNA includes the DNA sequence of SEQ ID NO: 4, or degenerate variants thereof encoding the amino acid sequence of SEQ ID NO: 8. The invention also features a substantially pure DNA molecule which includes the SspB, SspC, SspD, and SspA genes; preferably, the DNA includes the DNA sequence of SEQ ID NO: 15. The invention also features a substantially pure DNA molecule which includes the SspH gene; preferably, the DNA includes the DNA sequence of SEQ ID NO: 13, or degenerate variants thereof encoding the amino acid sequence of SEQ ID NO: 14. The invention also features a substantially pure DNA molecule which includes the Salmonella tyrosine phosphatase A (stpA) gene; preferably, the DNA includes the DNA sequence of SEQ ID NO: 10, or degenerate variants thereof encoding the amino acid sequence of SEQ ID NO:12.

The invention also features a cell into which has been introduced substantially pure DNA encoding an Ssp (or a mutant variant thereof). The substantially pure DNA can be introduced as a portion of a plasmid or other autonomously replicating molecule. In addition the substantially pure DNA can be introduced by homologous recombination. Preferably, the bacterial cell is a Salmonella cell; more preferably the bacterial cell is a *Salmonella typhimurium* cell. Cells into which have been introduced substantially pure DNA encoding an Ssp (or mutant variant thereof) can be used as a source of purified Ssp.

The invention includes a substantially pure SspC polypeptide, e.g., a polypeptide which includes an amino acid sequence substantially identical to the amino acid sequence of SEQ ID NO: 6 or an active fragment thereof and a substantially pure SspD polypeptide, e.g., a polypeptide which includes an amino acid sequence substantially identical to the amino acid sequence of SEQ ID NO: 7 or an active fragment thereof. The invention includes a substantially pure SspB polypeptide, e.g., a polypeptide which includes an amino acid sequence substantially identical to the amino acid sequence of SEQ ID NO: 5 (incomplete protein sequence) or an active fragment thereof and a substantially pure SspA polypeptide, e.g., a polypeptide which includes an amino acid sequence substantially identical to the amino acid sequence of SEQ ID NO: 8 (incomplete protein sequence) or an active fragment thereof. The invention includes a substantially pure full-length SspB polypeptide, e.g., a polypeptide which includes an amino acid sequence substantially identical to the aminoacid sequence of SEQ ID NO: 5 (incomplete protein sequence) and the remainder of the SspB sequence. Full-length SspA and SspB genes can be isolated by those skilled in the art using the partial DNA sequences disclosed herein. The invention also includes a substantially pure full-length SspA polypeptide, e.g., a polypeptide which includes an amino acid sequence substantially identical to the amino acid sequence of SEQ ID NO: 8 (incomplete protein sequence) and the remainder of the SspA sequence. The invention also features An active fragment of an Ssp B polypeptide or an SspC polypeptide or an SspD polypeptide is defined as an SspB, SspC, or an SspD polypeptide, respectively, at least 50 amino acids, preferably at least 25 amino acids, more preferably at least 10 amino acids in length having the ability to induce BME in the absence of the full-length version of the corresponding protein. In other preferred embodiments the SspB, SspC, SspD or SspA polypeptide is able to translocate into an epithelial cell, preferably a human epithelial cell. Translocation can be assayed using any suitable assay, e.g., the assay of Sogy et al. (*Molecular Microbiol.* 14:583:94, 1994).

The invention also includes a substantially pure SspH polypeptide, e.g., a polypeptide which includes an amino acid sequence substantially identical to the amino acid sequence of SEQ ID NO:14, or a biologically active fragment thereof.

The invention also includes a substantially pure IagB polypeptide, e.g., a polypeptide which includes an amino acid sequence substantially identical to the amino acid sequence of SEQ ID NO:11, or a biologically active fragment thereof.

Also within the invention is an antibody which binds to a Ssp, e.g., a polyclonal or monoclonal antibody which specifically binds to an epitope of Ssp. Polyclonal and monoclonal antibodies produced against the polypeptides of the invention can be used as diagnostic or therapeutic agents. The invention encompasses not only an intact monoclonal antibody, but also an immunologically-active antibody fragment, e.g., a Fab or (Fab)$_2$ fragment; an engineered single chain Fv molecule. In preferred embodiments, the antibody may be linked to a detectable label, e.g. a radioactive label, fluorescent label, paramagnetic label, or colorimetric label.

The invention also includes a method of detecting a Salmonella infection in a mammal which includes the steps of contacting a biological sample derived from the mammal, e.g., a human patient, with a Ssp-specific antibody and detecting the binding of the antibody to a Ssp in the sample. Antibody binding indicates that the mammal is infected with Salmonella. The presence of Salmonella in a biological sample may also be detected using a method which includes the steps of contacting the sample with a Ssp-encoding DNA, or the complement thereof, under high stringency conditions and detecting the hybridization of the DNA to nucleic acid in the sample. Hybridization indicates the presence of Salmonella in the biological sample. By "high stringency" is meant DNA hybridization and wash conditions characterized by high temperature and low salt concentration, e.g., wash conditions of 65° C. at a salt concentration of approximately 0.1×SSC. For example, high stringency conditions may include hybridization at about 42° C. in the presence of about 50% formamide; a first wash at about 65° C. with about 2×SSC containing 1% SDS; followed by a second wash at about 65° C. with about 0.1×SSC.

The invention also features a method for detecting the presence of antibodies to an Ssp using all or part of an Ssp protein. The method includes contacting a biological sample with the Ssp protein and measuring the binding of the Ssp protein to an antibody present in the sample.

The invention also features a method of targeting an antigen to an epithelial cell in a mammal which includes the steps of linking the antigen to an Ssp, e.g., SspC or SspD, or active fragment thereof, to produce a Ssp chimeric antigen and administering the chimeric antigen to the mammal.

A method of inducing a cytotoxic T cell immune response in a mammal is also within the invention. This method includes the steps of linking the antigen to an Ssp or active fragment thereof to produce a sap chimeric antigen and contacting an antigen-presenting cell, e.g., a Class I major histocompatibility complex (MHC) antigen-expressing cell, with the chimeric antigen.

The invention also features a vaccine which includes a bacterial cell, the virulence of which is attenuated by decreased secretion of a Ssp, and a method of vaccinating an mammal, e.g., a human patient, against a Salmonella infection by administering such a vaccine. Preferably, the bacterial cell is a *Salmonella typhimurium* cell, e.g., a Salmonella enteriditis cell, or a *Salmonella typhi* cell. A live Salmonella cell in which a gene encoding a heterologous antigen is inserted into a Ssp-encoding gene is also included in the invention.

Also within the invention is a substantially pure StpA polypeptide and a method of dephosphorylating a protein which includes the steps of contacting the protein, e.g., a protein at least one tyrosine of which is phosphorylated, with a StpA polypeptide or an active fragment thereof. An active fragment of StpA is defined as a Salmonella-derived polypeptide at least 10 amino acids in length which is capable of removing a phosphate group from a tyrosine residue.

The invention feature live Salmonella (particularly *Salmonella typhimurium*) vaccines in which one or more gene required for BME is mutated so as reduce their activity. Among the genes which can be mutated are SspB, SspC, and SspD. Although SspA appears not to be required for BME, it may be useful to mutate this gene as well (preferably in combination with mutation of one or more of the other Ssp genes). Any mutation of these genes which decreases function, including complete or partial deletion and one or more point mutations may be useful. In addition, function of Ssp gene may be impaired by altering its control region. The invention provides a Salmonella vaccine which does not cause transient bacteremia. In general, the invention features a bacterial cell, preferably a Salmonella cell, e.g., a *S. typhi, S. enteritidis typhimurium*, or *S. cholorao-suis* cell, the virulence of which is attenuated by a first mutation in an Ssp gene. The preferred mutations are loss of function mutations. However, functions causing partial loss of function may be useful if virulence is adequately reduced. Such a bacterial cell can be used as a vaccine to immunize a mammal against salmonellosis.

The Salmonella cell may be of any serotype, e.g., *S. typhimurium, S. psratyphi* A, *S. paratyphi* B, *S. paratyphi* C, *S. pylorum, S. dublin, S. heidelberg, S. newport, S. minnesota, S. infantis, S. virchow,* or *S. panama.*

The first mutation may be a non-revertible null mutation in one or more of the following genes: SspB, SspC, or SspD. Preferably, the mutation is a deletion of at least 100 nucleotides; more preferably, the mutation is a deletion of at least 500 nucleotides; even more preferably, the mutation is a deletion of at least 750 nucleotides. Mutations in the prgH gene or the prgH operon can be used for the same purpose.

In preferred embodiments loss or function (partial or complete) is due to decreased expression as a result of a change or mutation, e.g., a deletion, (preferably a non-revertible mutation) at the promoter or other regulatory element of SspB, SspC, or SspD (or some combination thereof).

In another aspect, the invention features a vaccine including a bacterial cell which is attenuated by decrease of expression of a Ssp virulence gene.

The invention also features a live Salmonella cell, or a substantially purified preparation thereof, e.g., a *S. typhi, S. enteriditis typhimurium,* or *S. cholerae-suis* cell, in which there is inserted into a virulence gene, e.g., an Ssp gene, a gene encoding a heterologous protein, or a regulatory element thereof.

In another aspect the invention includes a method of vaccinating an animal, e.g., a mammal, e.g., a human, against a disease caused by a bacterium, e.g., Salmonella, including administering a vaccine of the invention.

By "vaccine" is meant a preparation including materials that evoke a desired biological response, e.g., an immune response, in combination with a suitable carrier. The vaccine may include live organism, in which case it is usually administered orally, or killed organisms or components thereof, in which case it is usually administered parenterally. The cells used for the vaccine of the invention are preferably alive and thus capable of colonizing the intestines of the inoculated animal.

By "mutation" is meant any change (in comparison with the apropriate parental strain) in the DNA sequence of an organism. These changes can arise e.g., spontaneously, by chemical, energy e.g., X-ray, or other forms of mutagenesis, by genetic engineering, or as a result of mating or other forms of exchange of genetic information. Mutations include e.g., base changes, deletions, insertions, inversions, translocations or duplications.

A mutation attenuates virulence if, as a result of the mutation, the level of virulence of the mutant cell is decreased in comparison with the level in a cell of the parental strain, as measured by (a) a significant (e.g., at least 50%) decrease in virulence in the mutant strain compared to the parental strain, or (b) a significant (e.g., at least 50%) decrease in the amount of the polypeptide identified as the virulence factor in the mutant strain compared to the parental strain.

A non-revertible mutation, as used herein, is a mutation which cannot revert by a single base pair change, e.g., deletion or insertion mutations and mutations that include more than one lesion, e.g., a mutation composed of two separate point mutations.

Heterologous protein, as used herein, is a protein that in wild type, is not expressed or is expressed from a different chromosomal site, e.g., a heterologous protein is one encoded by a gene that has been inserted into a second gene.

A substantially purified preparation of a bacterial cell is a preparation of cells wherein contaminating cells without the desired mutant genotype constitute less than 10%, preferably less than 1%, and more preferably less than 0.1% of the total number of cells in the preparation.

A substantially pure DNA, as used herein, refers to a nucleic acid sequence, segment, or fragment, which has been purified from the sequences which flank it in a naturally occurring state, e.g., a DNA which has been removed from the sequences which are normally adjacent to the fragment, e.g., the sequences adjacent to the fragment in the genome in which it naturally occurs. The term also applies to DNA which has been substantially purified from other components which naturally accompany the DNA, e.g., DNA which has been purified from proteins which naturally accompany it in a cell.

Other features and advantages of the invention will be apparent from the following description of the preferred embodiments and from the claims.

By "polypeptide" is meant any chain of amino acids, regardless of length or post-translational modification (e.g., glycosylation or phosphorylation).

By "substantially identical" is meant a polypeptide or nucleic acid exhibiting at least 50%, preferably 85%, more preferably 90%, and most preferably 95% sequence identity to a reference amino acid or nucleic acid sequence. For polypeptides, the length of comparison sequences will generally be at least 10 amino acids, preferably at least 20 amino acids, more preferably at least 25 amino acids, and most preferably amino acids. For nucleic acids, the length of comparison sequences will generally be at least 50 nucleotides, preferably at least 60 nucleotides, more preferably at least 75 nucleotides, and most preferably 100 nucleotides.

Sequence identity is typically measured using sequence analysis software (e.g., Sequence analysis software package of the genetics computer group, university of Wisconsin biotechnology center, 1710 university avenue, Madison, Wis. 53705). Such software matches similar sequences by assigning degrees of homology to various substitutions, deletions, substitutions, and other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

By a "substantially pure polypeptide" is meant a Ssp polypeptide which has been separated from components which naturally accompany it. Typically, the polypeptide is substantially pure when it is at least 60% Ssp by weight. Preferably, the preparation is at least 75%, more preferably at least 90%, and most preferably at least 99%, by weight, Ssp polypeptide. A substantially pure Ssp polypeptide may be obtained, for example, by extraction from a natural source (e.g., Salmonella bacterium); by expression of a recombinant nucleic acid encoding a Ssp polypeptide; or by chemically synthesizing the protein. Purity can be measured by any appropriate method, e.g., using column chromatography, polyacrylamide gel electrophoresis, or by HPLC analysis.

A protein is substantially free of naturally associated components when it is separated from those contaminants which accompany it in its natural state. Thus, a protein which is chemically synthesized or produced in a cellular system different from the cell from which it naturally originates will be substantially free from its naturally associated components. Accordingly, substantially pure polypeptides include those derived from one type of prokaryotic organism, e.g., *S. typhimurium*, but synthesized in *E. coli* or another prokaryotic organism.

By "substantially pure DNA" is meant DNA that is free of the genes which, in the naturally-occurring genome of the organism from which the DNA of the invention is derived, flank the gene. The term therefore includes, for example, a recombinant DNA which is incorporated into a vector; into an autonomously replicating plasmid or virus; or into the genomic DNA of a prokaryote or eukaryote; or which exists as a separate molecule (e.g., a cDNA or a genomic or cDNA fragment produced by PCR or restriction endonuclease digestion) independent of other sequences. It also includes a recombinant DNA which is part of a hybrid gene encoding additional polypeptide sequence, e.g, a hybrid gene encoding a chimeric antigen.

Other features and advantages of the invention will be apparent from the following description of the preferred embodiments thereof, and from the claims.

DETAILED DESCRIPTION

FIG. 1 is a diagram of the a genetic map of the 59–60 min region of the *S. typhimurium* chromosome and partial physical map of the restriction endonuclease sites of the prgH chromosomal region within the hil locus and related plasmids. The horizontal arrows indicate the direction of transcription of the orfl, prgHIJK, and org genes and of the neomycin promoter of the Tn5B50 insertions within the hil locus. The vertical arrows indicate and the location of the predicted start of transcription of the prgHIJK operon (small arrow) and the location of the two Tn5B50 insertions that define the hil locus (large arrows). The open triangle indicates the location of the prgH1::TnphoA insertion. Restriction endonuclease sites are as follows: B, BamHI; E, EcoRI; H, HindIII; S, SacI; Ss, SspI; V, EcoRV; X, XhoI.

FIG. 2 is a photograph of a Northern blot assay in which the prgHIJK and org transcripts are identified. Blot hybridization of a prgH (A), prgI-J (B) prgK (C), org (D), and pagC (E) DNA probe to RNA purified from wild-type (Wt) and phoP constitutive ($P^c$) S. typhimurium strains were grown aerobically to 0.5 optical density units. The bars indicate the RNA markers and are 9488, 6255, 3911, 2800, 1898, and 872 nucleotides (NT) in size from top to bottom.

FIG. 3 is a photograph of a primer extension analysis of RNA isolated from wild-type and $PhoP^c$ S. typhimurium strains by using an oligonucleotide primer IB08 corresponding to nucleotides 1217 to 1199 of the prgH sequence. Lanes labeled "AGCT" represent dideoxy DNA sequencing reactions. The lane labeled "wt" represents the products of a primer extension reaction initiated with primer IB08 and wild-type RNA as a template, and the lane labeled "$P^c$" Represents the products of a primer extension reaction initiated with the same primer and $phoP^c$ RNA as a template. Reverse transcription of wild-type RNA with primer IB08 resulted in an approximately 270-nucleotide product corresponding to a predicted transcriptional start at nucleotide 949 of the prgH sequence. Abbreviations: wt, wild type strain 14028s; $P^c$, $PhoP^c$ strain CS022.

FIG. 4A is a diagram showing the similarity and alignment of prgI, mxiH, and yscF predicted gene products.

FIG. 4B is a diagram showing the similarity and alignment of prgJ and mxiI predicted gene products.

FIG. 4C is a diagram showing the similarity and alignment of prgK, mxiJ, and yscJ predicted gene products. For FIGS. 4A–4C, residues conserved among each of the predicted gene products are indicated with a plus (+); residues conserved among the prgI and either the mxiH or yscF predicted gene products and between the prgK and either the mxiJ or yscJ predicted gene products are indicated with an asterisk (*). The location of the lipoprotein processing sites (Leu-Xaa-Gly-Cys) of the prgK, mxiJ, and yscJ predicted gene products are indicated by underlining. Predicted protein sequences were compared using the GCG BLAST network service and ALIGN program (Feng et al., *J. Mol. Evol.* 35:351–360, 1987; Higgins et al., *CABIOS* 5:151–153, 1989).

Figure 5:
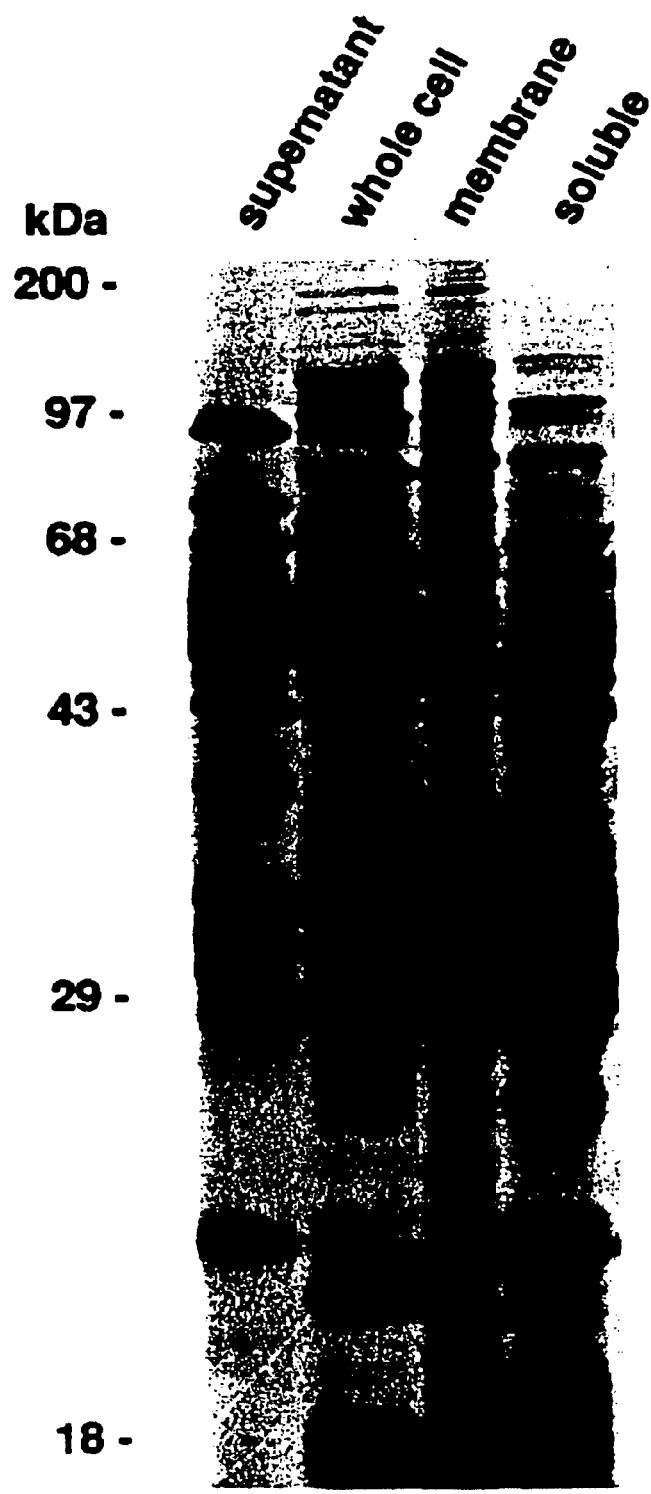

FIG. 5 is a photograph of a SDS-PAGE gel. Salmonella proteins found in the culture supernatant of stationary-phase S. typhimurium 140289 were compared to proteins isolated from lysed whole cells or cellular fractions (membranes or intracellular soluble proteins). TCA precipitable material from 2 ml of supernatant from cultures of $OD_{600}$=2.2 was used. The whole cell, membrane, and soluble lanes contained material from 0.10 ml, 0.35 ml, and 0.15 ml of cells, respectively. Proteins were fractionated in a 12% polyacrylamide gel by SDS-PAGE and stained with Coomassie Brilliant Blue R-250. The molecular masses of protein standards are indicated on the side of the gel as kDa.

Figure 6:
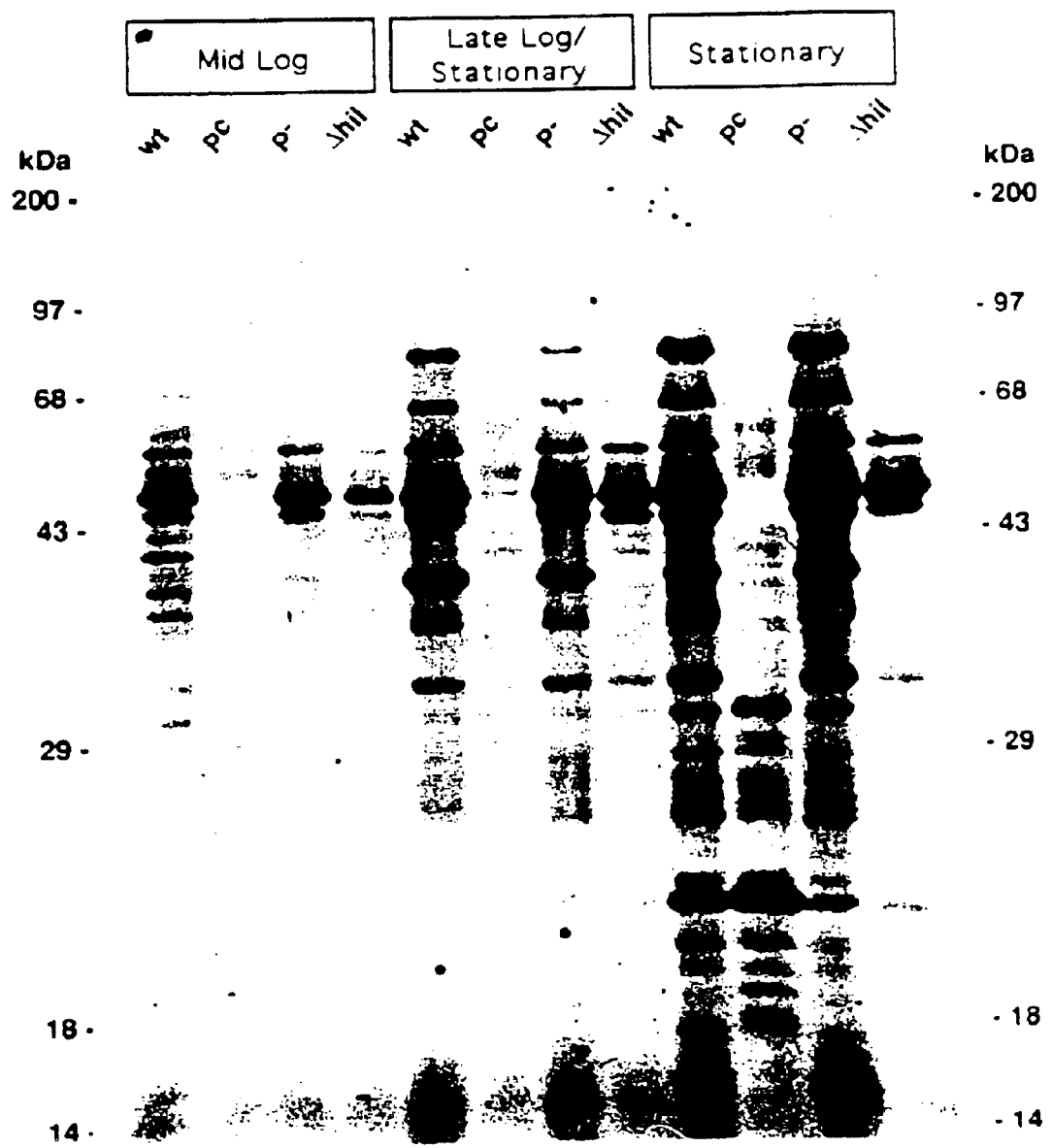

FIG. 6 is a photograph of a SDS-PAGE gel showing a comparison of culture supernatant proteins from S. typhimurium 14028s and culture supernatants from mutants which are defective in eucaryotic signaling. TCA precipitable material from 2 ml of bacterial culture supernatant was isolated at different times following inoculation: mid-log, $OD_{600}$=0.6; late-log/early-stationary, $OD_{600}$=1.1; stationary, $OD_{600}$=2.2. Proteins were fractionated in a 12% polyacrylamide gel by SDS-PAGE and stained with Coomassie Brilliant Blue R-250. The molecular masses of protein standards are indicated on the side of the gel as kDa. wt, wild type (14028s); $P^c$, $PhoP^c$ (CS022); $P^-$, $PhoP^-$ (CS015); Δhil (CS451), deleted for the hil locus.

Figure 7:
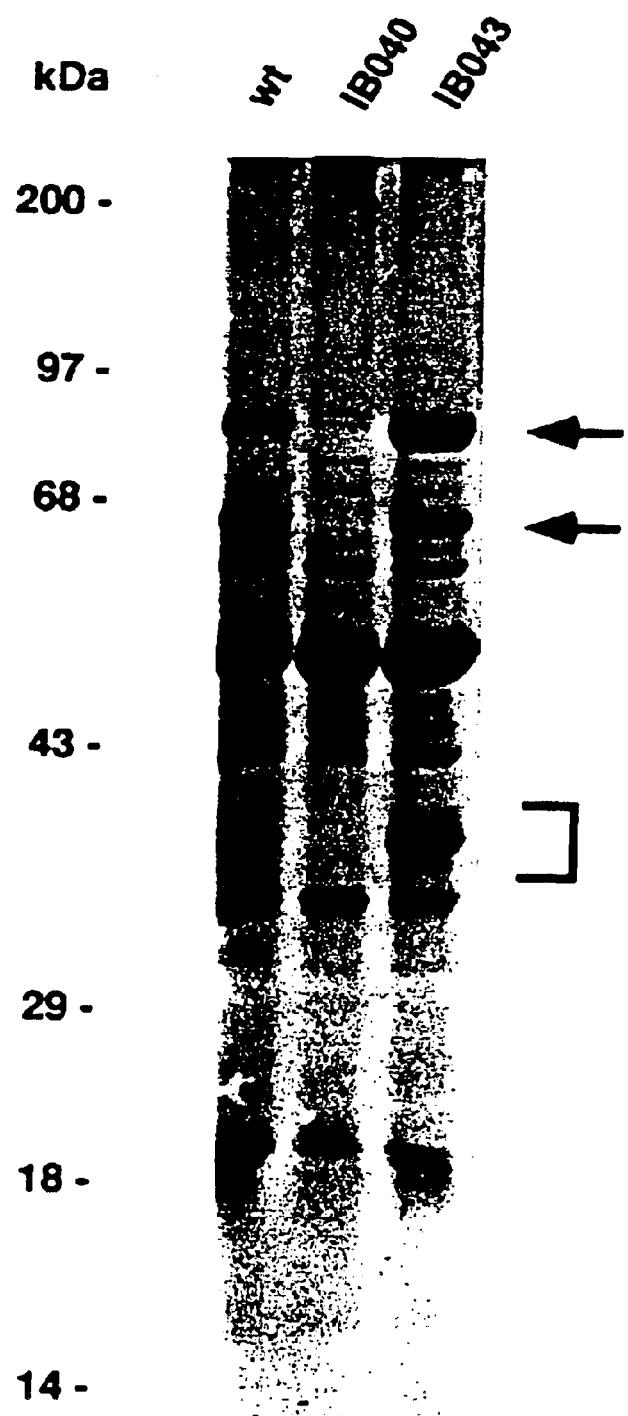

FIG. 7 is a photograph of a SDS-PAGE gel showing an analysis of prgH::TnphoA and complementation of the insertion mutation by pWKSH5. TCA precipitable material from 2 ml of supernatant from stationary phase cultures was fractionated in a 10% polyacrylamide gel by SDS-PAGE. Protein was stained with Coomassie Brilliant Blue R-250. The molecular masses of protein standards are indicated on the side of the gel as kDa. wt, wild-type (14028s); IB040, prgH1::TnphoA; IB043, prgH1::TnphoA with plasmid pWKSH5 containing a 5.1 kb insert of S. typhimurium DNA including prgHIJK. Supernatant protein bands complemented by pWKSH5 are indicated by arrows (87 kDa and 65 kDa) and a bracket (three bands in the 35–40 kDa range).

Figure 8:
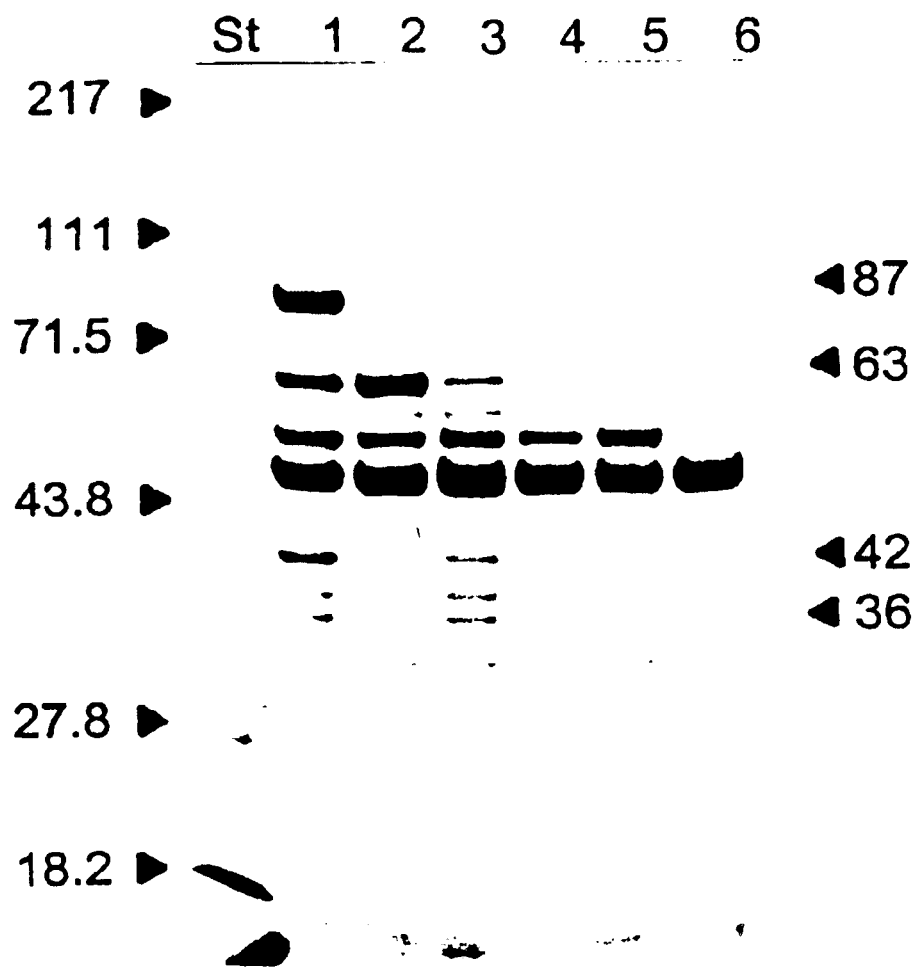

FIG. 8 is a photograph of a SDS-PAGE gel showing Salmonella secreted proteins (Ssp) concentrated from supernatants of different strains. Each lane contains Ssp collected from 2 ml of culture supernatant. Lanes 1: wild-type S. typhimurium SL1344; 2: EE638 (lacZY11-6); 3: EE633 (lacZY4); 4: VB122 (hilA::kan-112); 5: EE637 (invF::lacSY11-5); 6: IB040 (prgH1::TnphoA) St: molecular weight standard. Sizes of protein bands are given in kDa. * marks a protein band which was variably present in different preparations of Ssp from the same strains.

Figures 9, 10:
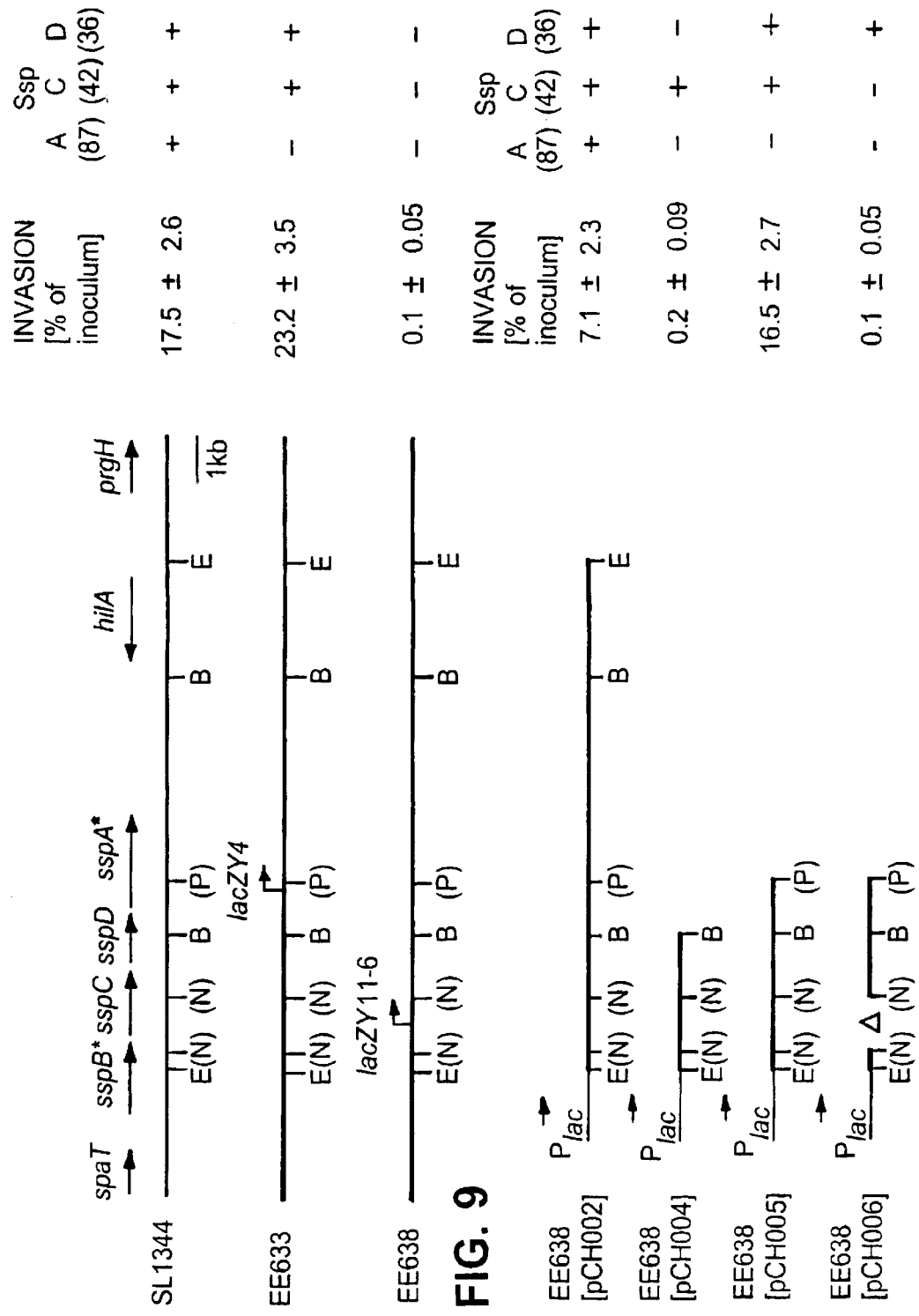

FIG. 9 is a diagram showing the chromosomal organization of the sspBCDA genes and phenotypes of mutants sspC::lacZY4 (EE633) and sspA::lacZY11-6 (EE638). The chromosomal location of ssp with respect to spaT and prgH is shown. An asterisk (*) indicates partially sequenced genes. Restriction sites in parentheses have only been mapped in the left region of the 11 kb EcoRI fragment. Abbreviations of restriction sites are: E: EcoRI, B: BamHI, P: PvuII, N: NcoI. Invasion of epithelial cells by different S. typhimurium strains is given as the percentage of the bacterial inoculum surviving gentamicin treatment. Values represent means and standard errors of the means of three independent experiments, each performed in triplicate. Presence or absence of Salmonella secreted proteins SspA, SspC and SspD in culture supernatants of different strains is indicated by + or –, respectively. The molecular weights in kDa of these Ssp are shown in parentheses.

FIG. 10 is a diagram showing a complementation analysis of EE638. Complementing fragments of chromosomal DNA in a low-copy plasmid are shown according to the chromosomal map. Designations of the plasmids are given in brackets on the left. The positions of the lac promoter ($P_{lac}$) are indicated. A indicates a deletion.

Figure 11:
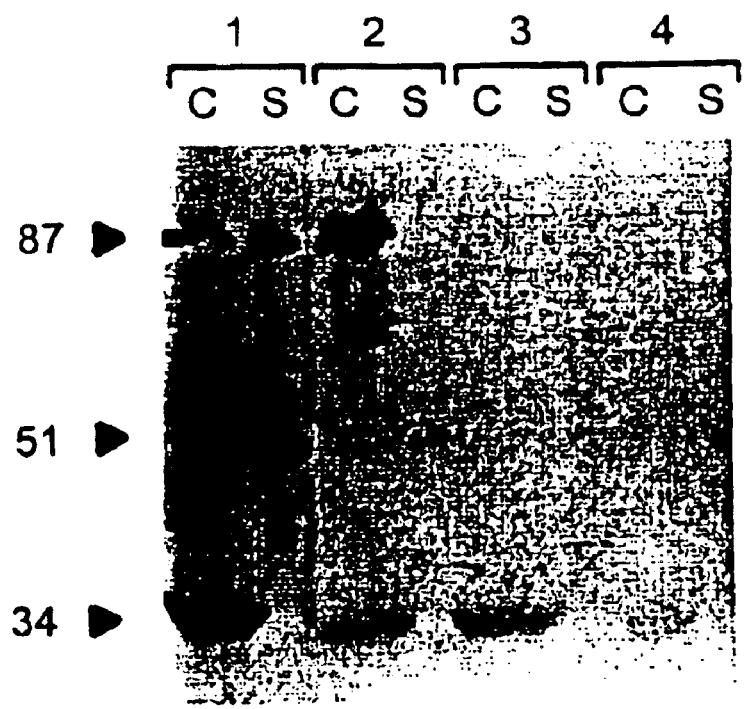

FIG. 11 is a photograph of an immunoblot analysis of various strains for expression and secretion of Ssp87. Total cellular proteins from bacteria collected from 0.2 ml of cultures were loaded in lanes designated "C", supernatant proteins from 0.2 ml bacterial culture supernatants were loaded in lanes designated "S". 1: wild type S. typhimurium; 2: CS022 ($PhoP^c$); 3: IB040 (prgH1::TnphoA); 4: CS451 (Δhil::Tn5-428); 5: EE638 (sspC::lacZY11-6); 6: EE633 (sspA::lacZY4).

FIG. 12 is a diagram showing a comparison of the deduced partial amino acid sequence of SspB with the S. flexneri homologue IpaB. Bars indicate identical residues, dots indicate gaps introduced in order to maximize similarity according to the GAP program of the GCG package.

FIG. 13 is a diagram showing a comparison of the deduced amino acid sequences of SspC with the S. flexneri homologues IpaC. Bars indicate identical residues, dots indicate gaps introduced in order to maximize similarity according to the GAP program of the GCG package.

FIG. 14 is a diagram showing a comparison of the deduced amino acid sequences of SspD with the S. flexneri homologues IpaD. Bars indicate identical residues, dots indicate gaps introduced in order to maximize similarity according to the GAP program of the GCG package.

FIG. 15 is a diagram of the amino-terminal sequence derived from the 5'-region of sspA. Amino acids determined by amino-terminal sequencing of SspC and SspA are underlined.

Figure 16:
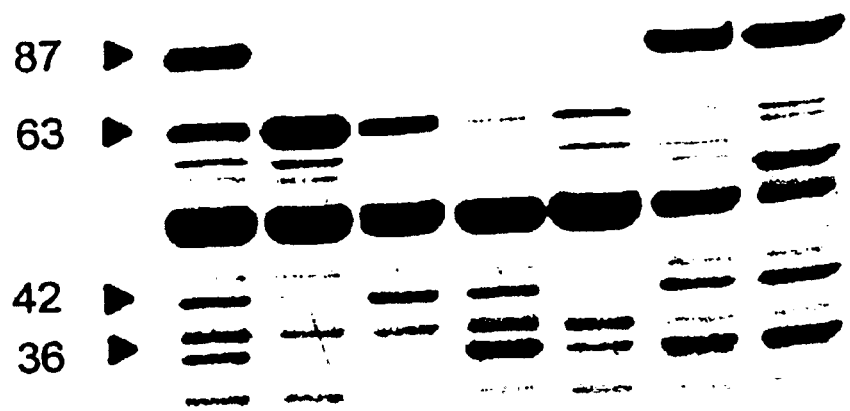

FIG. 16 is a photograph of a SDS-PAGE gel showing total soluble Ssp collected from 2 ml of culture supernatants of wild type S. typhimurium SL1344 and EE638 (sspC::lacZY11-6) transformed with various plasmids. Lanes 1: SL1344 [pWSK29]; 2: EE638 [pWSK29]; 3: EE638 [pCH004 (sspC)]; 4: EE638 [pCH005 (sspCD)]; 5: EE638 [pCH006 (SspD)]; 6: EE638 [pCH002 (sspCDA)]; 7: SL1344 [pCH002 (sspCDA)]. Lanes 8 and 9 contain soluble Ssp from SL1344 [pWSK29] and EE638 [pWSK29], respectively. The sizes of the protein bands are given in kDa. An asterisk (*) indicates a protein band which was variably present in different preparations of Ssp from the same strains.

Figure 17:

FIG. 17 is a photograph of an SDS-PAGE gel showing insoluble Ssp precipitates collected from 2 ml of culture supernatants of wild type S. typhimurium SL1344 and EE638 (sspC::lacZY11-6) transformed with various plasmids. Lanes 1: SL1344 [pWSK29]; 2: EE638 [pWSK29]; 3: EE638 [pCH004 (sspC)]; 4: EE638 [pCH005 (5spCD)]; 5: EE638 [pCH006 (SspD)]; 6: EE638 [pCH002 (sspCDA)]; 7: SL1344 [pCH002 (sspCDA)]. Lanes 8 and 9 contain soluble Ssp from SL1344 [pWSK29] and EE638 [pWSK29], respectively. The sizes of the protein bands are given in kDa. An asterisk (*) indicates a protein band which was variably present in different preparations of Ssp from the same strains.

Figure 18:
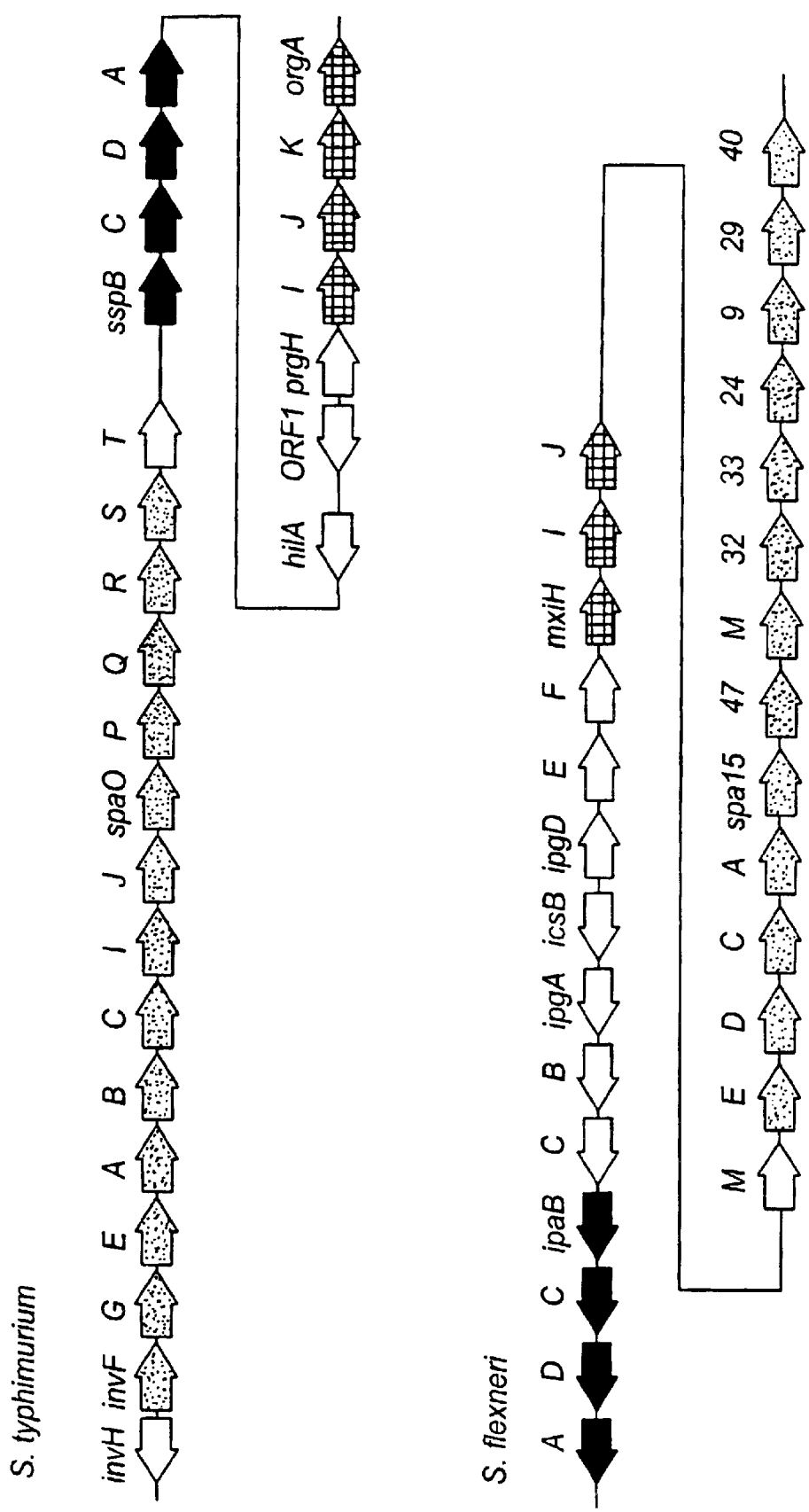

FIG. 18 is a diagram showing the genetic organization of the invasion gene clusters from S. typhimurium and S. flexneri. The relative positions of each gene are indication and the directions of gene transcription are indicated by arrows. Arrows are not drawn to scale. Gene clusters conserved in sequence and gene order are indicated by stippling (inv-spa/lxi-spa), crosshatching (prglJK/mxiHI), and dark arrows (ssp/ipa). Genes with no homologues within the respective regions are shown as open arrows.

FIG. 19 is a depiction of the nucleic acid sequence of SspB (missing part of the 5' end) (SEQ ID NO: 1).

FIG. 20 is a depiction of the nucleic acid sequence of SspC (SEQ ID NO: 2).

FIG. 21 is a depiction of the nucleic acid sequence of SspD (SEQ ID NO: 3).

FIG. 22 is a depiction of the nucleic acid sequence of SspB (missing part of the 3' end) (SEQ ID NO: 4) and the predicted amino acid sequence SspB (partial c-terminal) (SEQ ID NO: 5).

FIG. 23 is a depiction of the predicted amino acid sequences of SspC (SEQ ID NO: 6), SspD (SEQ ID NO: 7), and SspA (partial amino terminal) (SEQ ID NO: 8).

FIG. 24 is a depiction of the nucleic acid sequences of iagB (SEQ ID NO: 9) and stpA (SEQ ID NO: 10).

FIG. 25 is a depiction of the predicted amino acid sequences of iagB (SEQ ID NO: 11) and stpA (SEQ ID NO: 12).

FIG. 26 is a depiction of the nucleic acid sequence of prgH (SEQ ID NO: 13).

FIG. 27 is a depiction of the predicted amino acid sequences of prgB (SEQ ID NO: 14).

FIG. 28 is a depiction of the nucleic acid sequence of SspBCDA (truncated at 3' and 5' ends) (SEQ ID NO: 15).

FIG. 29 is a depiction of the nucleic acid sequence of prgH and 5' and 3' flanking sequences (SEQ ID NO: 16).

Ssp PROTEINS AND GENES

The Salmonella secreted proteins (Ssp) of the invention have a variety of uses. For example, they can be used as diagnostic reagents, therapeutic agents, and research products. The genes encoding Ssp also have a variety of uses. For example, they can be used as diagnostic reagents. They can also be used to create vaccines including live attenuated vaccines.

Because Salmonella infection is a significant health problem and because Ssp proteins are soluble proteins that are found on the surface of Salmonella, various Ssp, DNA encoding various Ssp, and antibodies directed against various Ssp are useful in diagnostic assays. Because Ssp are required for optimal virulence, DNA encoding a mutant Ssp having decreased function can be used to create strains of Salmonella with reduced virulence. Such strains are useful as live vaccines.

An Ssp (or a portion thereof which can gain entry into the cytoplasm) can be used to translocate a second molecule, e.g., a polypeptide, into the cytoplasm of a cell. This approach can be useful for the induction or priming of cytotoxic lymphocytes (CTL) directed against the second molecule. An Ssp (or a portion thereof capable of translocating an attached second molecule) can be used to introduce a second molecule into the cell cytoplasm for the purpose of drug delivery. Often the second molecule is a polypeptide which is covalently linked to an Ssp (or a portion thereof), e.g., by a peptide bond. Such molecules can be readily produced first preparing a chimeric gene encoding the Ssp (or portion thereof) and the second molecule as a single polypeptide chain. This gene can be used to prepare the fusion protein for administration to a patient. Alternatively, the chimeric gene can be introduced into a strain of Salmonella which can then be used as either a live vaccine or drug delivery system.

Ssp as Diagnostic Reagents

An Ssp can be used as a diagnostic tool for the detection of Salmonella infection in a patient or to evaluate status of an immune response to Salmonella. For example, one or more Ssp can be used an antigen in an ELISA assay to detect the presence of Salmonella-specific antibodies in a bodily fluid, e.g., blood or plasma, obtained from an infected patient or an individual suspected of being infected with Salmonella. Ssp can also be used to test immune cell activation, e.g., T or B cell proliferation or cytokine production, in a sample of patient-derived cells, e.g., peripheral blood mononuclear cells, to detect the presence of a cellular immune response to Salmonella.

Polynucleic acids (e.g., primers and probes) encoding all or part of an Ssp can be used in hybridization assays to detect the presence Salmonella infection, e.g., using a PCR assay or other probe or primer based assay designed to detect particular DNA sequences.

Antibodies capable of selectively binding a particular Ssp can be used to detect the presence of Salmonella in a biological sample. Such antibodies can be produced using standard methods.

Therapeutic Applications of Ssp Fusion Proteins

Fusion proteins comprising all or part of an Ssp and a second protein or polypeptide are useful for a variety of therapeutic applications such as vaccines (e.g., recombinant Salmonella vaccines or vaccines against heterologous pathogens), cell targeting agents for delivery of drugs (e.g., cytotoxic agents), and adjuvants, (e.g., to boost an immune response to a co-administered antigen).

To produce a recombinant Salmonella vaccine, a gene encoding an Ssp fusion protein can be introduced into a Salmonella vaccine. Because Ssp are involved in bacterial mediated endocytosis, the Ssp fusion protein will cause the second polypeptide or protein to be internalized by epithelial cells (or other cells to which the Ssp binds) of the individual to which the vaccine is administered. This internalization can trigger a Type I MHC-mediated response to the second protein or polypeptide. The induction of this response will lead to the induction of CTL (or the priming of CTL) specific for the second protein or polypeptide. The induction or priming of antigen-specific CTL can provide therapeutic or prophylactic benefits.

Purified fusion proteins can be used as recombinant vaccines. Proteins fused to Ssp are specifically targeted to epithelial cells or other cell types to which the Ssp bind; the fusion proteins are then internalized by the targeted cells. Thus, Ssp fusion proteins are useful to generate an immune response to the antigen to which the Ssp is linked or to deliver a therapeutic compound, e.g., a toxin for the treatment of cancer or autoimmune diseases in which the killing of specific cells, i.e., the cells to which a Ssp binds, is desired. Delivery of a toxin linked to a SspC or SspD polypeptide is especially useful in cancer therapy because man types of cancers are of epithelial cell origin.

Ssp fusion proteins which contain all or part of a Ssp linked to a heterologous protein can be made using methods known in the art. Two or more polypeptides may be linked together via a covalent or non-covalent bond, or both. Non-covalent interactions can be ionic, hydrophobic, or hydrophilic.

A covalent linkage may take the form of a disulfide bond. For example, the DNA encoding one of the polypeptides can be engineered to contain a unique cysteine codon. The second polypeptide can be derivatized with a sulfhydryl group reactive with the cysteine of the first component. Alternatively, a sulfhydryl group, either by itself or as part of a cysteine residue, can be introduced using solid phase polypeptide techniques.

A number of other covalent crosslinking agents, e.g., photoreactive crosslinkers, water-soluble crosslinkers, which are commercially available may be used to join a heterologous polypeptide to a Ssp to create a fusion protein. If the fusion protein is produced by expression of fused genes, a peptide bond serves as the link between the components of the fusion protein. Such fusion proteins are produced by expression of a chimeric gene in which sequences encoding all or part of an Ssp are in frame with sequences encoding the second protein or polypeptide. In some circumstances it may be useful to include a linker polypeptide between the Ssp and second protein of polypeptide.

Internalization of the fusion protein may not require the presence of a complete Ssp protein. A internalization-competent portion of an Ssp will be adequate in many circumstances. Whether a particular portion of a selected Ssp is sufficient for internalization can be tested as follows. The selected portion of an Ssp is fused to a calmodulin-dependent adenylate cyclase. If this test fusion protein ii internalized, it will be exposed to calmodulin and the cylcase will be activated. The presence of adenylate cyclase activity can then be used as a measure of internalization. This general approach is described by Sorg et al. (*Molecular Mcrobiol.* 14:583–94, 1994).

Ssp are virulence factors that alter the ability of bacteria to be internalized by specific populations of host cells and to induce an immune response. Salmonella with mutations in genes encoding Ssp are useful in the manufacture of live Salmonella vaccines with altered cell tropism.

Deletion or overexpression of Ssp in Salmonella can be used to target strains or fusion proteins to various mammalian cell types. Invasion of epithelial cells or macrophages can be selected depending on the Ssp mutated. For example, use of Salmonella as an antigen or drug delivery vehicle can be optimized by deleting part or all of a gene encoding a Ssp involved in bacterial mediated endocytosis (or mutating such a gene to impair Ssp function), thereby minimizing the ability of Salmonella to invade epithelial cells (and therefor maximizing antigen delivery to antigen presenting cells such as macrophages). In this manner, strains with mutated Ssp genes can be used to modulate the host immune system. Deletion of Ssp genes in Salmonella can also be used to alter the ability of Salmonella to stimulate IL-8 secretion by epithelial cells.

Fusions of antigens to Ssp genes can be used to facilitate an immune response to the linked antigens for the purpose of generating an antigen-specific cytotoxic T cell response in a patient. For example, Ssp fusions to viral antigens are useful as therapeutic vaccines for diseases such as AIDS and Herpes genitalis in which the generation of a cytotoxic T cell (CTL) response is desired. Delivery of antigens in this manner favors the generation of an antigen-specific CTL response because the Ssp portion of Ssp fusion protein mediates translocation of the fusion protein across eucaryotic cell membranes into the intracellular compartments in the cytoplasm of cells which participate class I MHC-mediated antigen processing and presentation, i.e., the generation of class I MHC-restricted antigen-specific CTLS.

Fusion proteins which include all or part of a Ssp linked to a cytotoxic molecule can be used to target a cytotoxic molecule to a specific cell type, e.g., an epithelial cell-derived cancer cell, which would then by killed by the cytotoxic agent. Cytotoxic fusion proteins can be synthetically or recombinantly produced and administered directly to a patient. Alternatively, live Salmonella expressing a cytotoxic Ssp fusion protein can be administered and allowed to produce and secrete the fusion protein in vivo.

Ssp are also useful as adjuvants to boost the immunogenicity of antigens with which they are delivered or to which they are chemically or recombinantly linked. Ssp that have enzymatic effects, e.g., phosphatase activity, on certain types of eucaryotic cells can be used to promote specific types of immune responses such as TH2 or TH1 T cell responses. Since these proteins are secreted and are likely taken up in the cytoplasm of eucaryotic cells, gene fusions to these proteins are likely to be more immunogenic and more efficient in inducing the development of an immune response, particularly a class I MHC-restricted CTL response.

Various oral and parenteral delivery systems are known in the art and can be used to deliver the Ssp polypeptides and/or chimeric antigens of the invention, such as encapsulation in liposomes, or controlled release devices. The compositions of the invention can be formulated in a pharmaceutical excipient in the range of approximately 10 $\mu$g/kg and 10 mg/kg body weight.

The compositions and methods of the invention provide the tools with which to construct better vaccines against Salmonella infection and for the prevention and treatment of other diseases, e.g., cancer and AIDS, by using Salmonella secreted proteins as carriers of heterologous antigens, e.g., tumor antigens or viral antigens, either as purified components or as hybrid proteins produced in live Salmonella vaccine strains.

Ssp and Attenuated Bacterial Strains

Deletion or mutation of one or more Ssp genes can be used to attenuate vaccine strains. For instance deletion of Ssp genes leads to lack of neutrophil transmigration across epithelial cell monolayers (a model system that correlates well with the ability of certain strains to cause gastroenteritis).

Vaccine strains are usually administered at doses of $1 \times 10^5$ to $1 \times 10^{10}$ cfu/single oral dose. Those skilled in the art can determine the correct dosage using standard techniques.

Research Products

Ssp with enzymatic activity, e.g., Salmonella tyrosine phosphatase (stpA), can be used as reagents for protein modification. StpA catalyzes the release of phosphate groups from tyrosine residues in proteins, and thus, is especially useful in the field of signal transduction. Since a number of eucaryotic and procaryotic signal transduction proteins are regulated by the phosphorylation and dephosphorylation of tyrosine residues, stp can be used to deactivate or activate these proteins, thereby altering intracellular signal transduction. Thus, Stp can be used as a research tool to study and evaluate phosphorylation-regulated signal transduction pathways.

Modification of Ssp and Ssp Variants

When an Ssp is being used to translocate a second molecule into a eukaryotic cell, it may be useful increase expression of the Ssp (or Ssp fusion protein) so that BME is increased. Increased expression of sspC, SspD and other ssp genes may be accomplished using methods known in the art, e.g., by introducing multiple copies of the gene(s) into the bacterial cell or cloning the Ssp-encoding DNA under the control of a strong promoter.

Under other circumstances it may be desirable to increase uptake of a bacterial strain, e.g., a Salmonella strain, by a macrophage in a mammal by impairing the normal invasion mechanism of the strain. This can be accomplished by decreasing expression of the DNA encoding the SspC and/or SspD (and thereby decreasing secretion of Ssp and/or SspD polypeptides) and administering the cell to the mammal. Ssp expression may be reduced using methods known in the art, e.g., insertion of a transposon (Tn) into the gene, deletion of some or all of the gene, mutating a gene upon which SspC and/or SspD expression depends, egg., prgH, e.g., a deletion or Tn insertion in the prgHIJK operon. Instead of decreasing the expression of sspC and/or SspD, the method may include the step of impairing the function of one or both of the gene products, e.g., by Tn insertion, deletion mutagenesis, or by impairing the secretory pathway by which the gene products are secreted such that the gene products are produced but not effectively transported to the extracellular environment.

EXAMPLE 1

PhoP/PhoQ Transcriptional Repression of S. typhimurium Invasion Genes

Evidence for a Role in Protein Secretion

The PhoP-repressed prgH locus of S. typhimurium may be important for signaling epithelial cells to endocytose S. typhimurium. The following series of experiments demonstrate that the prgH locus is an operon of four genes encoding polypeptides of 392 amino acids (prgH), 80 amino acids (prgI), 101 amino acids (prgJ), and 252 amino acids (prgK). These experiments also demonstrate that expression of the 2.6-kb prgHIJK transcript is reduced when PhoP/PhoQ is activated, suggesting that PhoP/PhoQ regulates prgHIJK by transcriptional repression. Further, analysis of the culture supernatants from wild-type S. typhimurium revealed the presence of at least 25 polypeptides larger than 14 kDa. Additional experiments demonstrated that prgH1::TnphoA, phoP constitutive (PhoP$^c$), and hil deletion mutants have significantly defective supernatant protein profiles. A further set of experiments described below demonstrate that both the invasion and supernatant protein profile defects of the prgH1::TnphoA mutant can be complemented by a 5.1 kb plasmid that included prgHIJK. Taken together these results suggest that PhoP/PhoQ regulates extracellular transport of proteins by transcriptional repression of secretion determinants and that secreted proteins are likely involved in signaling epithelial cells to endocytose bacteria.

The following reagents and procedures were used to evaluate the prgH locus.

Bacterial Strains Growth and Conditions

S. typhimurium strain ATCC 14028s (American Type Culture Collection, Bethesda, Md.) is a virulent wild-type parent strain from which all other Salmonella strains described in Example 1 were derived. Bacterial strains and plasmids are described in Table 1. Luria-Bertani broth (LB) was used as rich bacterial growth medium. Antibiotics were added to LB broth or agar in the following concentrations: ampicillin, 25 µg/ml; chloramphenicol, 50 µg/ml; kanamycin, 45 µg/ml.

DNA Sequencing and Analysis

Double-strand templates were sequenced by the dideoxy-chain termination method known in the art as modified for use with Sequenase™ (US Biochemicals, Corp.) and [α-$^{35}$S] DATP. Computer analysis of the DNA sequence was accomplished with the GENEPRO (Riverside Scientific, Riverside, Calif.) and Wisconsin package (GCG, version 7) programs. The nucleotide sequence of the prgHIJK locus has been deposited in GeneBank under accession number U21676.

RNA Extraction, RNA Blot Analyses, and Primer Extension Analyses

RNA was isolated from mid-log phase cultures ($OD_{600}$= 0.5) of aerobically-grown (with shaking) and microaerophically-grown (without shaking) Salmonella strains using a standard hot phenol procedure (Pulkkinen et al., J. Bacteriol. 173:86–93, 1993). For RNA blots, 20 µg of RNA was diluted in $H_2O$ and incubated for 15 minutes at 55° C. in 50% formamide, 17.5% formaldehyde in 1×Northern buffer (0.36 M $Na_2HPO_4$-$7H_2O$, 0.04 M $NaH_2PO_4$-$H_2O$). Samples were run on 1% agarose gels containing 6% formaldehyde and 1×Northern buffer and were transferred to Gene Screen Plus membranes (NEN/Dupont). RNA was crosslinked to the membrane using a Stratalinker™ UV crosslinker (Stratagene, La Jolla, Calif.). Membranes were hybridized and washed according to the manufacturer's protocol.

The DNA probes for RNA-DNA and DNA-DNA blot hybridization were obtained from recombinant plasmid DNA by restriction endonuclease digestion or by polymerase chain reaction (PCR) using the GeneAmp™ PCR kit (Perkin-Elmer/Cetus). The following DNA probes were synthesized: a 841-bp prgH probe from the oligonucleotide primers IB07 (5'-CCAGGTGGATACGGA-3'; SEQ ID NO: 17; nucleotides 1198 to 1212) and IB19 (5'-TAGCGTCCTCCCCATGTGCG-3'; SEQ ID NO: 18; nucleotides 2039 to 2021); a 433-bp prgI-prgJ probe from the primers IB26 (51-CCGGCGCTACTGGCGGCG-3'; SEQ ID NO: 19), nucleotides 2304 to 2321) and DP04

(5'AGCGTTTCAACAGCCCCG-31; SEQ ID NO: 20), nucleotides 2737 to 2719); a 341-bp prgK probe from primers DP03 (5'-CGGGGCTGTTGAAACGC-3'; SEQ ID NO: 21), nucleotides 2720 to 2736) and DP08 (5'-AACCTGGCCTTTTCAG-3'; SEQ ID NO: 22), nucleotides 3060 to 3045); a 724-bp org probe from primers DP15 (5'-GGCAGGGAGCCTTGCTTGG-3'; SEQ ID NO: 23), nucleotides 3774 to 3792) and DP17 (51-GTGCCTGGCCAGTTCTCCA-3'; SEQ ID NO: 24); and a 608-bp pagC probe from a Psi and StuI restriction-endonuclease digest of pWPL4 that contains the wild-type pagC gene. DNA probes were radiolabelled using a standard method of random priming with [α-$^{32}$P]dCTP.

For primer extension analyses, oligonucleotide primers (0.2 picomoles) were end-labelled with (γ-$^{32}$P]dATP (NEN/Dupont), annealed to *S. typhimurium* RNA (20 µg) and extended with reverse transcriptase (Gibco BRL, St. Louis, Mo.). Reactions were electrophoresed in 6% polyacrylamide, 8 N urea gels adjacent to sequencing reactions initiated with primers used for cDNA synthesis.

DNA Blot Hybridization Analysis

Chromosomal DNA was isolated, restriction endonuclease digested, size fractionated in agarose gels, and transferred to GeneScreen Plus membranes (NEN/Dupont). For dot blot hybridization experiments, high stringency hybridization was performed according to standard methods at 65° C. using radiolabelled probes.

Protein Isolation and Analysis

Bacteria were grown in LB, with shaking at 37° C. Bacterial cultures were chilled to 4° C. and centrifuged at 154,000×g for 1.7 hours. The supernatant was carefully removed and trichloroacetic acid (TCA) was added to a final concentration of 10%. The precipitates were collected by centrifugation at 69,000×g for 1 hour, rinsed with cold acetone, dried and stored at 4° C. The bacterial cell pellet was fractionated to obtain periplasmic, cytoplasmic, and membrane fractions. Samples were analyzed by sodium dodecyl sulfate-polyacrylamide gel electrophoresis (SDS-PAGE) on a 10–12% polyacrylamide (0.1 M Tris pH 8.45, 0.1% SDS) gel using a standard Tris-glycine buffer systemor standard Tris-tricine buffer system. TCA precipitates were mixed with sample buffer (250 mM Tris pH 6.8, 2% SDS, 0.0025% bromophenol blue, 5.0% β-mercaptoethanol, 10% glycerol) and heated to 100° C. for 5 minutes. Proteins were visualized by staining with Coomassie Brilliant Blue R-250.

Enzyme Assays

Presence of the marker enzymes, alkaline phosphatase (periplasm) and β-galactosidase (cytoplasm) were used to assess fraction purity. A plasmid, pPOS3, containing an arabinose-inducible phoA gene, was inserted into wild-type strain 14028s by transformation and moved into other strains using P22 bacteriophage-mediated transduction. Addition of arabinose (0.02%) to the culture medium induced transcription of the phoA gene. Determination of alkaline phosphatase activity of strains containing pPOS3 was performed using the substrate p-Nitrophenyl phosphate according to standard methods. The results were expressed in standard units for β-galactosidase (Miller, J. H., 1972, Experiments in Molecular Genetics, Cold Spring Harbor Laboratory, Cold Spring Harbor, N.Y., pp. 352–355). β-galactosidase was produced from a strain with a mudJ-generated gene fusion of msg and lacZ. The gene, msg, is constitutively expressed and not PhoP regulated. β-galactosidase activity of strains carrying msg::MudJ was measured using routine methods (Miller et al., supra).

TABLE 1

Bacterial strains, plasmids and relevant properties

Relevant genotype

*S. typhimurium*

| | |
|---|---|
| ATCC 14028s | Wild Type |
| CS002 | pho-24 |
| CS019 | phoN2zxx::6251Tn10d-Cm |
| IB040 | CS019 with prgH1::TnphoA |
| IB043 | IB040 with pwKSH5 |
| CS015 | phoP-102::Tn10d-Cm |
| CS451 | 14028s derivative of EE451 with Δhil |

*Eschericnia coli*

| | |
|---|---|
| DH5α | F⁻Φ8ΦdlacZΔM15Δ(lacZYA-argF)U169endA1 recA1hsdR17deoRthi-1supE44λgyrA96relA1 |

Plasmids

| | |
|---|---|
| pIB01: | pUC19 (amp$^R$) containing a 10.7-kb EcoRV fragment with prgH1::TnphoA (kan$^R$) |
| pVB3 | pUC19 containing a 5.9-kb HindIII-EcoRI fragment of the prgH locus |
| pWKSH5 | pWKS30 (amp$^R$) containing a 5.1-kb HindIII fragment of prgH locus |
| pWPL4 | pUC19 containing a 5.0-kb EcoRV fragment of the pagC locus |
| pPOS5 | pBR322 containing arabinose-inducible PhoA |

Cloning and Sequencing of prgH

Figure 1:
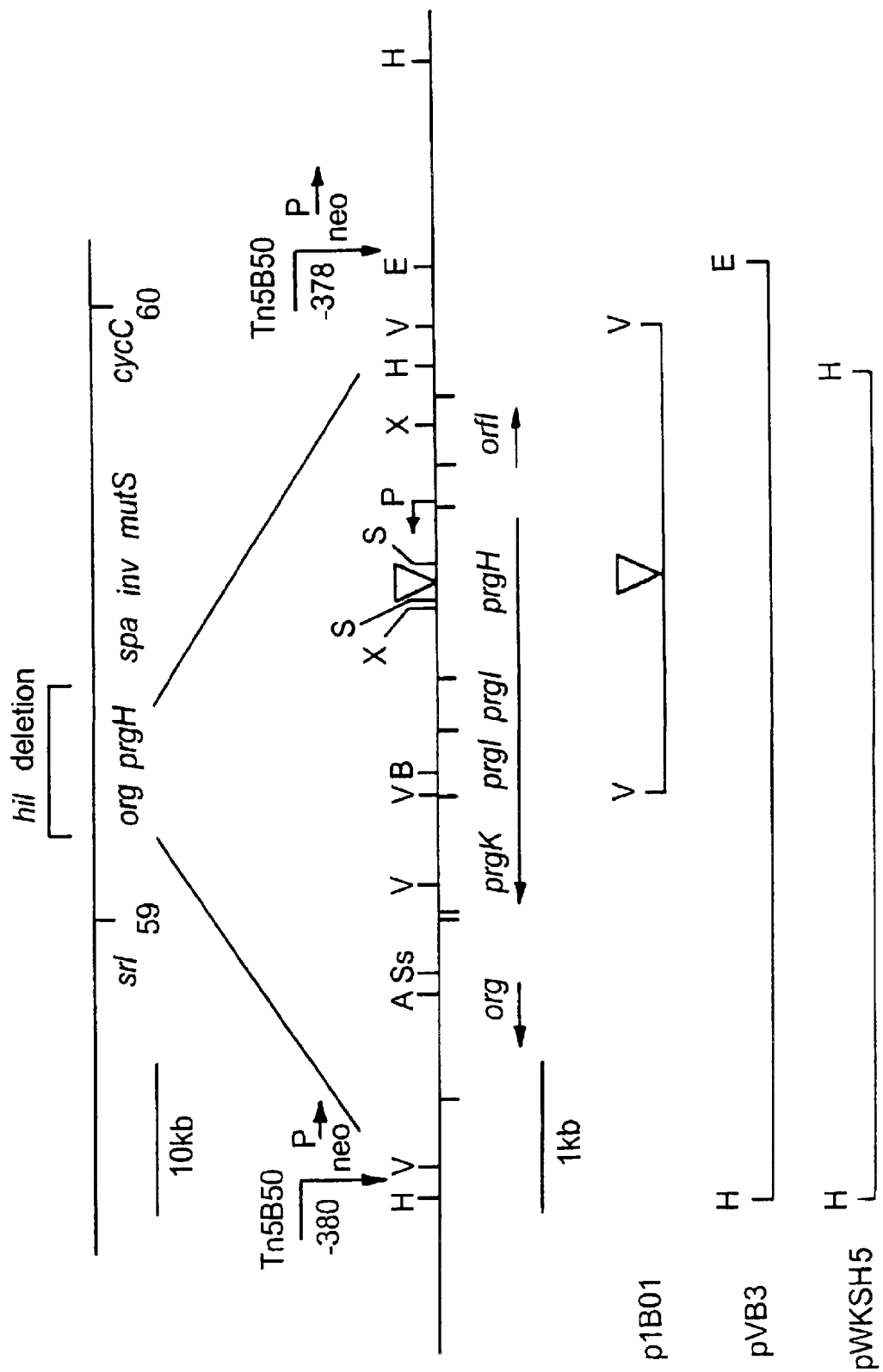

The DNA containing the prgH1::TnphoA gene fusion was cloned based upon information derived from the physical map of restriction endonuclease sites surrounding the transposon insertion (FIG. 1) (Behlau et al., *J. Bacteriol.* 175:4475–4484, 1993, hereby incorporated by reference). Chromosomal DNA from strain IB040 containing the prgH1::TnphoA insertion was digested with the restriction endonuclease EcoRV and ligated into SmaI digested pUC19 to generate a library of recombinant plasmids. These recombinant plasmids were transformed into *Eschericnia coli* (*E. coli*) DH5α. A recombinant plasmid containing a 10.7 kb EcoRV fragment was identified by selecting for kanamycin resistance (TnphoA encoded) and was designated pIB01 (FIG. 1). DNA hybridization analysis of strain IB040 with a radiolabelled 1.5-kb HindIII-SacI-generated DNA fragment of pIB01 resulted in hybridization to an approximately 10.7-kb EcoRV DNA fragment. This was approximately 7.7 kb (the size of TnphoA) larger than the 3-kb fragment present in the wild-type strain ATCC 140288. This probe also hybridized strongly to plasmid pVB3 that contained the 5.9 kb HindIII-EcoRI fragment of the hil locus (FIG. 1), confirming the location of the prgH locus within this region. This data indicated DNA containing the prgH1::TnphoA insertion had been cloned.

The DNA sequence of the 4,034-bp HindIII-SspI fragment (within which the TnphoA insertion in prgH was localized) was determined by sequencing plasmid pIB01 containing the cloned prgH1::TnphoA allele. This sequence was confirmed by DNA sequencing of pWXSH5 containing the wild-type prgH allele (FIG. 1). Information from DNA sequence of the prgH1::phoA fusion junction was used to determine the direction of transcription and correct reading frame of prgH. TnphoA was inserted after nucleotide 1548 within an open reading frame that extended from nucleotides 981 to 2156. prgH was predicted to encode a 392 amino acid polypeptide with a calculated $M_r$ of 44,459 daltons and pI of 5.86. The N-terminal portion of prgH was found to have a stretch of nonpolar residues followed by the motif Leu-Xaa-Gly-Cys at residues 24 to 27 (corresponding to nucleotides 1050 to 1061) characteristic of the processing site of bacterial lipoproteins. There was a strong hydrophobic domain (amino-acid residue 144 to 154, corresponding to nucleotides 1410 to 1433) upstream of the TnphoA insertion.

Analysis of the nucleotide sequence located upstream of prgH revealed an additional open reading frame from nucleotides 665 to 222, termed orfl, likely to be oppositely transcribed from prgH. The intergenic region between orfl and prgH was 216 nucleotides. orfl was predicted to encode a gene product of 148-amino-acid residues with a calculated $M_r$ of 17,186. The start codon of orfl was preceded by a potential ribosome binding site at 7 to 11 nucleotides 5' to the predicted start of translation (5'-AAAGG-3', nucleotides 676 to 672) suggesting that this open reading frame was translated. The orfl predicted gene product had no signal sequence nor any strong hydrophobic domains.

Identification of prgI, prgJ, and prgK

Analysis of the nucleotide sequence located downstream from prgH revealed four additional open reading frames that were predicted to be transcribed in the same direction and form an operon: (a) nucleotides 2184 to 2423; (b) nucleotides 2445 to 2747; (c) nucleotides 2747 to 3502; and (d) nucleotide 3476 to beyond the 3' SspI site. The first three of these four open reading frames identified were designated prgI, prgJ, and prgK respectively. prgI, prgJ, and prgK were predicted to encode gene products of 80 amino acids ($M_r$, 8865 daltons), 101 amino acids ($M_r$, 10,929 daltons), and 252 amino acids ($M_r$, 28,210 daltons). The predicted gene products encoded by prgI and prgJ did not contain a signal sequence or strong hydrophobic domains. The predicted gene product encoded by prgK contained a N-terminal hydrophobic region followed by a potential lipoprotein processing site from amino-acid residue 15 to 18 (corresponding to nucleotides 2788 to 2800). The fourth open reading frame corresponded in DNA sequence to the *S. typhimurium* oxygen-regulated gene (org).

prgH-K Transcription is Negatively Regulated by PhoP/PhoQ

Figures 2A, 2B, 2C, 2D, 2E:
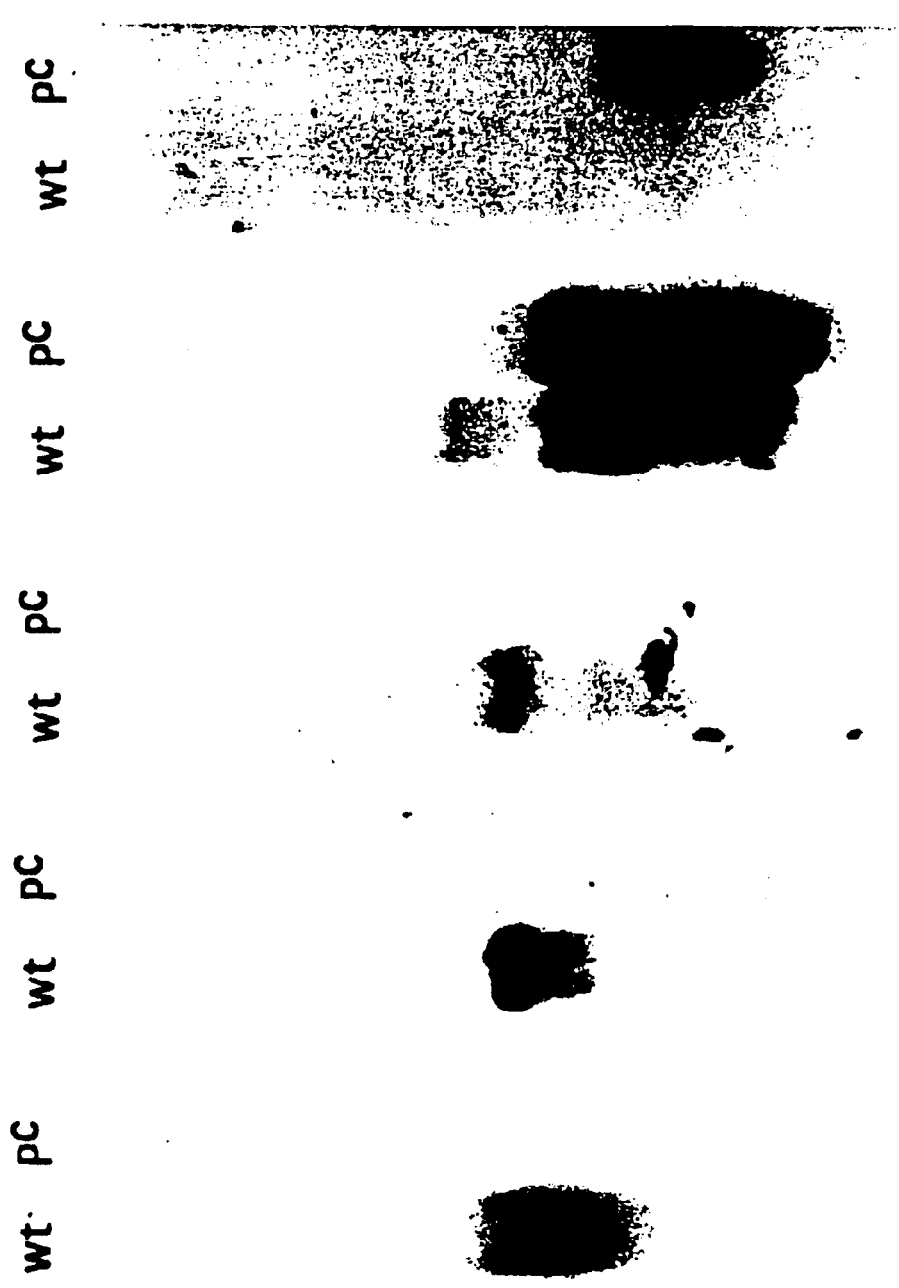
Figure 3:
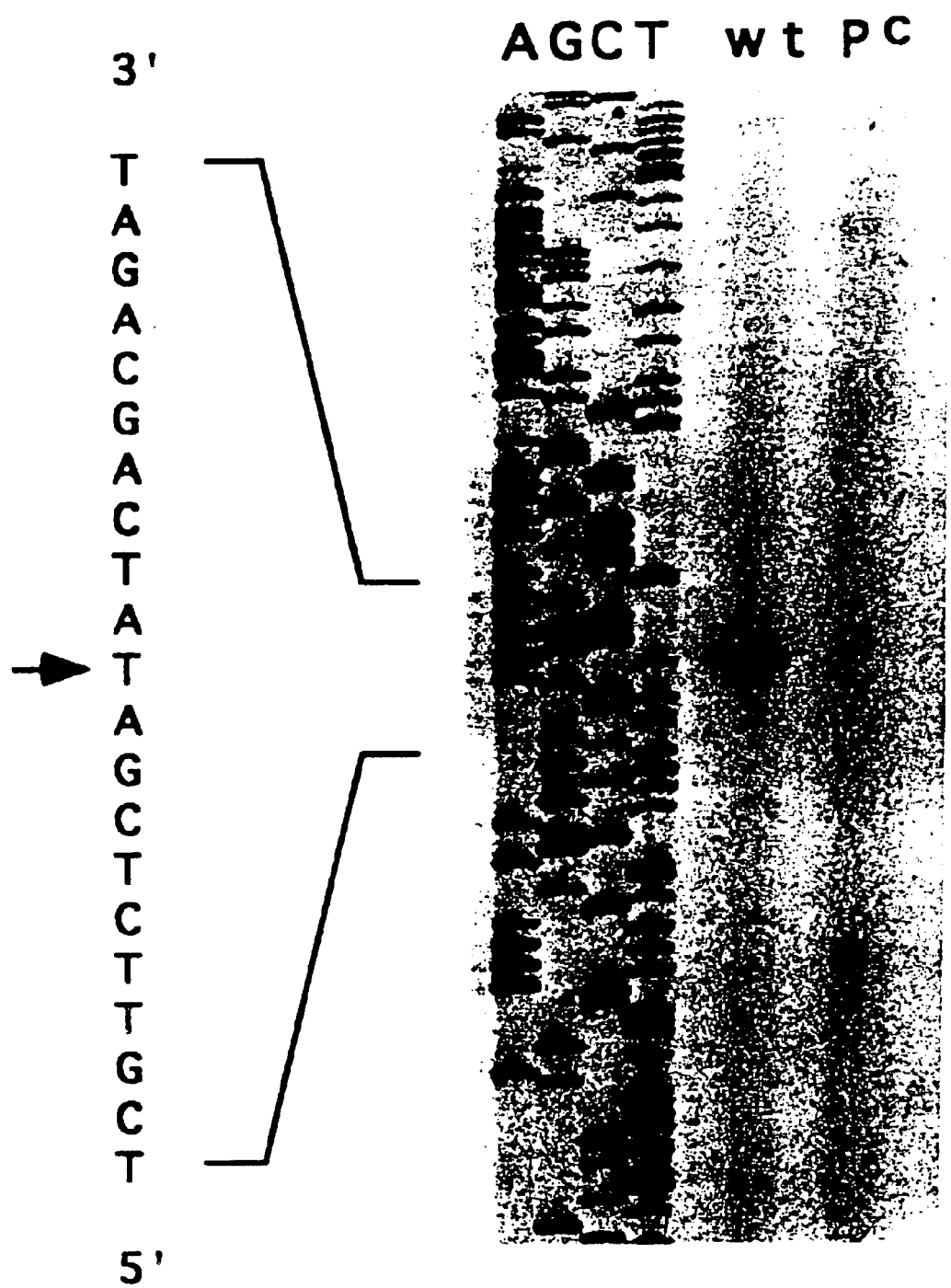

To determine whether prgH was negatively regulated by PhoP/PhoQ, RNA isolated from wild-type (ATCC 14028s) and phoP$^C$ (CS022) strains of *S. typhimurium* were analyzed. In numerous RNA blot analyses, the prgH-specific DNA probe hybridized with an approximately a 2600-nucleotide RNA from the wild-type strain (FIG. 2). The size of the RNA that hybridized to the prgH probe was similar to that of the prgH-K open reading frame predicted from the DNA sequence (i.e., 2600 vs. 2522 nucleotides). In contrast, no transcript was seen when equal amounts and similar quality of RNA (as assessed by methylene blue staining) isolated from the PhoP$^C$ strain was probed with prgH-specific DNA (FIG. 3). In comparison, when the same RNA preparations were hybridized with a pagC-specific probe, an approximately 1100-nucleotide pagC transcript was highly expressed in the phoP$^C$ strain (FIG. 2), consistent with the constitutive phenotype of pag gene expression in the phoP$^C$ mutant (Pulkkinen et al., *J. Bacteriol.* 173:86–93, 1991, hereby incorporated by reference). These results indicate that regulation of prgH occurs at the level of transcription.

Primer extension analysis was performed to obtain information on the possible initiation site of prgH transcription. Based on this analysis, the start of prgH transcription was predicted to begin approximately 32 nucleotides upstream from the prgH translational start (FIG. 3). Several different primers were used that resulted in primer extension products of differing lengths, but all predicted that transcription initiated at this site. The predicted −10 (5'-TAATCT-3') and −35 (5'-TTCATC-31) regions are similar to the consensus sequences for typical α70 *E. coli* promoters. Similar to the results of RNA blot hybridization analysis, a primer extension product was detected only with RNA isolated from wild-type *S. typhimurium* and not with RNA isolated from the PhoP$^C$ strain (FIG. 3).

The size of the RNA that hybridized to the prgH-specific probe suggested that prgH-K could form a transcriptional unit. Therefore, to determine whether prgI-K formed an operon that was regulated by PhoP/PhoQ, RNA blot hybridization and primer extension analysis were performed using DNA probes and primers specific to the prgI, prgJ, and prgK open reading frames. Similar to the results with prgH, the prgI-J and prgK-specific DNA probes hybridized with an approximately 2600-nucleotide RNA isolated from wild-type *S. typhimurium* and not with RNA from the phoP$^C$ strain (FIG. 2). No primer extension products less than 350 nucleotides were detected using RNA isolated from either the wild-type or phoP$^C$ strains using prgI, prgJ, and prgK primers. These primers were from 1662 to 2332 nucleotides downstream from the predicted start of prgH transcription. These findings indicated that prgH-K were transcribed as an operon, heretofore referred to as prgHIJK. Furthermore, this operon was likely to be transcribed from the prgH promoter and was negatively regulated by PhoP at the level of transcription.

org is not Regulated by PhoP/PhoQ

Although the above results suggested that the prgHIJK transcriptional unit did not include org, experiments were performed to test this possibility. Blot hybridization analysis was performed with RNA isolated from wild-type *S. typhimurium* and an org-specific DNA probe. As shown in FIG. 2, two distinct transcripts hybridized to the org probe: an approximately 1400-nucleotide abundant RNA and a minor RNA of approximately 3800 nucleotides. The size of the smaller RNA was similar to that of the org open reading frame (1400 vs. 1236 nucleotides). In comparison, only the major 1400-nucleotide RNA was seen when RNA from the phoP$^C$ strain was hybridized with the org-specific DNA probe, suggesting that the 3800-nucleotide RNA was PhoP repressed.

A minor RNA of approximately 3800 nucleotides also was detected in long exposure of wild-type RNA blots that were hybridized with either the prgH, prgI-J, or prgK probes, suggesting possible cotranscription of prgHIJK and org. However, both the major (1400 nucleotide) and minor (3800 nucleotide) transcripts were detected when RNA isolated from the prgH1::TnphoA strain was hybridized with the org probe, indicating that the prgH1::TnphoA insertion was not polar on either of the org transcripts. Because expression of an org::lacZY fusion was shown to be increased approximately fourteen fold in low-oxygen compared with high-oxygen tension, RNA from wild-type and phoP$^C$ strains that were grown aerobically or microaerophically to an optical density at 260 nm of 0.5 were compared by blot hybridization with the org-specific DNA probe. No substantial difference was seen in the relative amounts of RNA transcripts detected in wild-type or phoP$^C$ strains grown under these conditions. These data indicate that org did not form part of the prgHIJK operon and that it was not regulated by PhoP/PhoQ.

The prgI, prgJ, and prgK Predicted Polypeptides are Similar to *S. flexneri* Mxi and *Y. enterocolitica* Ysc Proteins The sequences of the five predicted polypeptides (PrgH, PrgI, PrgJ, PrgK, and Orfl were compared with the protein sequences translated from the GeneBank library using BLAST network software. This comparison revealed similarity between the predicted products of prgI, prgJ, and prgK and the MxiH, MxiI, and mxiJ proteins of *S. flexneri*. Each of the these polypeptide sequences were similar over their entire length, with 65% (PrgI vs. MxiH), 38% (PrgJ vs. MxiI), and 46% (PrgK vs. mxiJ) of positions occupied by identical residues (FIGS. 4A–4C). The prgI and prgK predicted gene products were also similar to the YscF and YscJ proteins, respectively, of *Y. enterocolitica*, with 28% and 30% of positions occupied by identical residues. The Poisson probabilities were highly significant for each of these comparisons. No protein similar to the prgH or orfl predicted polypeptides was detected in the protein sequence library.

Isolation of Proteins from *S. typhimurium* Culture Supernatants

The role of prgHIJK in *S. typhimurium* protein secretion was analyzed by examination of the proteins present in cell culture supernatant. Culture media of wild-type bacteria was collected for protein analysis by centrifuging stationary phase cultures at 154,000×g for 1.7 hours. From 6–8 µg/ml of protein was precipitated by addition of trichloroacetic acid (TCA) to overnight culture supernatants. The TCA-precipitable material in 2 ml of supernatant then was fractionated by sodium dodecyl sulfate-polyacrylamide gel electrophoresis (SDS-PACE) (FIG. 5). Approximately 25 protein bands, ranging in molecular mass from 18–87 kDa, were detected by Coomassie brilliant blue staining.

To rule out the possibility that the supernatant protein bands represented proteins released from lysed cells, soluble and membrane fractions of whole cells and whole cell lysates were compared with proteins from the supernatant by SDS-PAGE (FIG. 5). Many of the major polypeptides in the supernatant (e.g., the polypeptide with molecular mass of 87 kDa) were not the major proteins in the other cellular fractions. Conversely, major intracellular soluble proteins and membrane proteins (e.g., the 36 kDa OmpC porin) were not detected in the supernatant in this analysis. In addition, following centrifugation, the overnight culture media from bacteria expressing alkaline phosphatase (a periplasmic protein) and β-galactosidase (a cytoplasmic protein) always contained less than 9% and 1%, respectively, of the whole-cell activity of these enzymes. Although some of the supernatant protein bands may represent degradation products of larger protein species, these data indicate that *S. typhimurium* was capable of significant protein secretion.

To determine the timing of release of polypeptides in to the supernatant and to test for an effect of PhoP regulon mutations on secretion, supernatants from CS015, with a null mutation in PhoP (PhoP−), CS022 (PhoP$^c$), and wild-type bacteria (ATCC 14208s) were compared. As shown in FIG. 6, the quantity of protein increased for each strain when supernatant samples taken from mid-log-phase ($OD_{600}$= 0.6), late-log/early-stationary-phase ($OD_{600}$=1.1), and stationary-phase ($OD_{600}$=2.2) were compared. However, the pattern of major protein bands detected for each strain was unchanged from mid-log to stationary phase (FIG. 6).

Altered Supernatant Protein Profiles of Mutants Defective in Signaling Epithelial Cells At each phase of growth examined, a similar pattern and quantity of protein was detected in the culture supernatants of PhoP− strain CS015 and wild-type bacteria (FIG. 6). In contrast, the protein level of 2 ml of phoP$^C$ strain CS022 supernatant was 24% of wild type levels. At least 10 major protein bands seen in the wild-type supernatant were greatly reduced or undetectable by Coomassie blue staining of the CS022 supernatant, especially those of higher molecular weight (FIG. 6). In addition, four major protein bands appeared to be increased in amount in CS022 compared with wild-type supernatant (31.5 kDa, 30 kDa, 23 kDa, and 20 kDa) (FIG. 6). Although this result could be due to degradation of higher molecular weight polypeptides, these data suggest that the phoP$^c$ mutant likely was defective in synthesis or secretion of Ssp.

The defect observed with the PhoP$^c$ mutant was consistent with prg gene products having a role in protein secretion. Therefore, the Ssp of strains having transposon insertion or deletion of prgHIJK were compared to wild-type bacteria (ATCC 14028s) by SDS-PAGE. As observed for the PhoP$^c$ mutant, IB040 (prgH1::TnphoA) and CS451, containing a 10-kb deletion of hil locus (Δhil) DNA, each had a pronounced defect in their Ssp profile compared with the wild-type strain (FIG. 6 and 7). IB043 and CS451 culture supernatants contained 100% and 62%, respectively, of wild-type protein levels. At least 5 and 11 major protein bands seen in the wild-type supernatant were greatly reduced or undetectable by Coomassie blue staining of the IB040 and CS451, respectively. Five protein bands [87 kDa, 65 kDa, and three in the 35–40 kDa range (FIG. 7), two of which run as a doublet under different electrophoretic conditions (FIG. 6)] were undetectable in the supernatants of CS022, IB040, and CS451. These findings indicated that the presence of at least some of the products of the prgHIJK operon were necessary for synthesis or secretion of Ssp.

The defect in bacterial mediated endocytosis associated with prgH1::TnphoA was complemented by a low-copy number plasmid, pWKSH5, containing a 5.1-kb fragment including prgHIJK, org, and orfl . Consistent with this observation, the prgH1::TnphoA mutant carrying pWKSH5 (strain IB043) had a supernatant protein profile similar to that of wild type (FIG. 7). Of the five protein bands undetectable or greatly reduced in culture supernatants of prgH1::TnphoA, each was detected in IB043 and three of them were increased in amount (87 kDa, 65 kDa, and 35 kDa) compared with wild-type supernatants. This finding demonstrates a correlation between the ability to secrete proteins and induction of epithelial cell bacterial mediated endocytosis.

The prgH Locus is Important for *S. typhimurium* to Induce Endocytosis by Epithelial Cells The defect in BME of the prgH1::TnphoA mutant is complemented by a plasmid containing 5.1 kb of DNA from this region, indicating that the gene or genes disrupted by the prgH1::TnpboA insertion are important for BME. Analysis of the DNA sequence of this region identified six potential open reading frames that could be affected by this transposon insertion. As depicted in FIG. 1, five of these open reading frames, namely those designated prgH-K are either disrupted (i.e., prgH) or are 3' to the prgH1::TnphoA insertion. The orfl translational start is 884 nucleotides upstream from the TnphoA insertion and that orfl is predicted to be oppositely transcribed from the prgHIJK operon.

An approximately 2600 nucleotide PhoP-repressed transcript was detected when RNA was hybridized with prgH-, prgI-J-, or prgK-specific DNA probes. In contrast, the predominant transcripts detected with org was smaller (approximately 1400 nucleotides), was not altered in the prgH1::TnphoA mutant, and was not repressed by PhoP. Primer extension analysis of the potential start site of transcription, the size of the prgHIJK transcript, and the presence of a potential transcriptional terminator immediately downstream of prgK also were consistent with transcription terminating before org.

In addition to the major transcripts of prgHIJK and org, a minor PhoP-repressed transcript of approximately 3800 nucleotides also was detected in multiple RNA blots hybridized with the org and prgH, prgI-J, or prgK DNA probes.

This minor RNA was similar in size to the combined prgHIJK and org open reading frames (i.e., 3731 nucleotides) and, thus, could represent cotranscription of prgHIJK and org. However, both the 3800- and 1400-nucleotide transcripts were detected in RNA from the prgH1::TnphoA mutant suggesting that the 3800-nucleotide RNA did not represent cotranscription of prgHIJK and org. These data indicate that one or more genes in the prgHIJK operon are important to BME of epithelial cells.

A PhoP constitutive mutation repressed the synthesis of approximately 20 prg-encoded cell-associated protein species (Miller et al., *J. Bacteriol.* 172:2485–2490, 1990, herein incorporated by reference). Although PhoP/PhoQ has been shown to transcriptionally activate pag (Miller et al., *Proc. Natl. Acad. Sci. USA* 86:5054–5058, 1989, herein incorporated by reference; Pulkkinen et al., supra, herein incorporated by reference), the mechanism of protein repression by PhoP/PhoQ had not been characterized prior to the present studies. No transcript was detected when RNA from the PhoP constitutive mutant was probed with prgH-, prgI-J-, or prgK-specific DNA, indicating that the prgHIJK operon was negatively regulated by PhoP/PhoQ at the level of transcription. Thus, PhoP/PhoQ can both activate and repress transcription of virulence genes.

Consistent with the role of one or more of the products of prgHIJK in bacterial mediated endocytosis and possibly in protein secretion, a low-copy plasmid containing 5.1 kb of DNA (IB043), including prgHIJK, org, and orfl , complemented both the bacterial mediated endocytosis defect and the supernatant protein profile defect of the prgH1::TnphoA mutant. Based upon its similarity to mxiJ and YsCJ, which are membrane-associated lipoproteins that are necessary for export and secretion of Ipa and Yops protein respectively, the prgK gene product is most likely to have such a role in bacterial mediated endocytosis and protein secretion. Similar to PrgK, PrgH was predicted to be a membrane lipoprotein. However, in contrast to prgI-K, which are similar to plasmid-encoded genes of Shigella and Yersinia spp., a prgH DNA probe hybridized to chromosomal DNA but not virulence-plasmid DNA from Shigella spp.

Neither they nor the prgI or prgJ predicted gene products have signal sequences or long hydrophobic domains that suggest their cellular localization. However, the location of these genes within operons that encode secretion determinants suggests that they may have a role in this process.

The predicted gene products of the prgHIJK operon were found to be similar to gene products required for protein secretion in other bacterial species. An analysis of proteins present in culture supernatants of *S. typhimurium* was performed. These experiments revealed that the supernatants of wild-type cultures contained a large number of protein bands, whereas strains with mutations affecting the prgH locus, including prgH1::TnphoA, Δhil and PhoP$^c$ were each defective in protein secretion as assessed by Ssp profiles. This analysis suggested that PhoP/PhoQ could control protein secretion, at least in part, by repressing prgHIJK whose products could form part of a secretion machinery. Furthermore, the finding that PhoP$^c$ and Δhil mutants were associated with greater defects in their Ssp profile compared with the prgH1::TnphoA mutant suggested that more than one mechanism may be involved in protein secretion and that gene products encoded by the 10 kb region that is deleted in the hil mutant also contribute to secretion of Ssp.

Since the strains with altered Ssp profiles were each impaired in signaling epithelial cells, these data suggest that Ssp are involved in signaling such cells to initiate BME. The finding that five Ssp were missing from culture supernatants of the prgH mutant suggested that one or more of these proteins were specifically involved in BME, e.g., Ssp and/or prgHIJK gene products may form a structure on the surface of *S. typhimurium* which induces bacterial mediated endocytosis.

*S. typhimurium* strains with transposons inserted between prgH and spa that result in reduced bacterial mediated endocytosis were also missing a subset of the Ssp missing from the prgHIJK mutant. DNA sequence analysis of the regions flanking the transposon insertions revealed deduced protein sequences that were similar to IpaB and IpaD of *S. flexneri*. These data suggest that the transposon insertions define an operon in *S. typhimurium* that encodes Ipa homologues.

EXAMPLE 2

*Salmonella typhimurium* Secreted Invasion Determinants

Two *Salmonella typhimurium* secreted protein (Ssp) mutants with transposon insertions located between spaT and prgH were identified. One mutant lacks the 87 kDa Ssp, while the other lacks Ssp of 87, 42, and 36 kDa. The invasiveness of these mutants implicates the 42 and 36 kDa Ssp, but not the 87 kDa Ssp in invasion. DNA sequencing of this region identified two complete and two partial open reading frames (designated sspb, sspC, SspD, and sspA).

The deduced amino acid sequences of sspBCDA are homologous to *Shigella flexneri* secreted proteins IpaB, Ipac, IpaD, and IpaA. Complementation analyses and amino-terminal sequencing showed that sspC and sspA encode the 42 kDa and the 87 kDa Ssp and that both proteins are secreted without amino-terminal processing. SspA is abundantly secreted by wild type bacteria but is completely retained within the cellular fraction of a mutant in prgHIJK encoding part of the Ssp secretion apparatus. A precipitate containing SspC and three major Ssp of 63, 59, and 22 kDa was isolated from culture supernatants of wild type bacteria. These data indicate that major secreted invasion determinants of *S. typhimurium* are structurally and functionally homologous to *S. flexneri* Ipa proteins.

The following reagents and experimental procedures were used to characterize Ssp.

Construction of Plasmids and Strains:

To construct pCH002, pVV8-1 was cut with EcoRI, the 11 kb fragment eluted from a 1% agarose gel and cloned into the EcoRI site of pWSK29. In pCH002, transcription of sspCDA is driven from the lac promoter. pCH004 was constructed by cloning the 3 kb BamHI fragment from pCH002 into the BamHI site of pWSK29. pCH005 contains the 4 kb EcoRI-PvuII fragment from pCH002 cloned into EcoRI-HincII restricted pWSK29. pCH006 was constructed by restriction of pCH005 with NcoI and religation of the 1.7 kb and the 5 kb fragment. The correct orientations of the cloned inserts were confirmed by appropriate restriction analyses.

PCR of a chromosomal fragment of EE638 comprising the 5'-region of Tn5lacZY and adjacent DNA was performed in three independent experiments by using primers OL 1 (5'CGCGGATCCATTATGGGATGTATCGG 3'; SEQ ID NO: 25) and OL2 (5'CCGGCAGCAAAATGTTGCAG 3'; SEQ ID NO: 26). The 0.8 kb amplified DNA fragments were then restricted with BamHI and cloned into pWSK29 for sequencing. All three sequences were identical.

Strain VB122 (hilA::kan-112) was constructed as follows: the mutation was originally constructed on a plasmid by inserting a kan cassette (Pharmacia Biotech, Piscateway, N.J.) in a HincII site in the 5' region of the hilA coding sequence. The plasmid-encoded hilA::kan-112 mutation was recombined into the chromosome, and the chromosomal mutation was confirmed by PCR analysis.

Mutant EE633 (lacZY4) was isolated by screening for oxygen regulated gene fusions created by random Tn5lacZY insertions in *S. typhimurium* VV114 (hilA::kan-114) and further selection for insertions linked to a hilA::kan-114 by P22 transduction into *S. typhimurium* SL1344 and selection for Tet$^R$ and Kan$^R$.

Media and Growth Conditions for Bacterial Cultures:

Bacteria were grown in LB broth at 37° C. If necessary, selection was carried out using 50 μg/ml ampicillin, 10 μg/ml tetracycline, or 25 μg/ml kanamycin.

Preparation and Analysis of *S. typhimurium* Supernatant Proteins:

Bacterial cultures were grown for 16 to 17 hours in 12 ml LB in 1.5×14 cm glass tubes at 37° C. on a TC-7 roller (New Brunswick, Edison, N.J.) at 50 rev./min. Soluble proteins from culture supernatants were obtained as described above. Precipitates in the culture were retrieved, rinsed 5 times with 1 ml H$_2$O, dissolved in sample buffer (4% SDS, 12% glycerol, 5% β-mercaptoethanol, 0.05 M Tris-HCl pH 6.8, 0.01% bromphenol blue), and resolved in 10% polyacrylamide gels using SDS-PAGE and a Tris-Tricine buffer.

Immunoblotting:

Whole cell samples were prepared from overnight cultures using standard methods with the additional step of filtering the culture through a Whatman 1 qualitative paper filter (Whatman International, Maidstone, Kent, England) before centrifugation. The proteins were resolved by SDS-PAGE and transferred to nitrocellulose by electroblotting using a conventional transfer buffer. Western blots were incubated with polyclonal rabbit serum prepared against the 87 kDa Ssp. The immunogen was purified by SDS-PAGE and injected into New Zealand White rabbits (Charles River, Wilmington, Mass.). Serum was collected after two booster injections and subsequently absorbed with an acetone powder prepared from *S. typhimurium* strain EE63. Horseradish peroxidase-labelled goat anti-rabbit antibodies were used to label the primary antibodies and were visualized using chemiluminescence (ECL, Amersham, International, Buckinghamshire, England)

Invasion Assays:

Invasion of HEp-2 epithelial cells was carried out according to the method of Behlau et al. (*J. Bacteriol.* 175:4475–4484, 1993). To minimize epithelial cell detachment from the bottom of the assay wells after bacterial uptake, the following modifications were introduced: invasion time was reduced from 90 to 60 min and gentamicin treatment was performed for 15 min with 100 μg/ml gentamicin, conditions which were shown to kill 99% of a bacterial culture of 2×108 cells/ml.

N-terminal Protein Sequencing:

Proteins separated by SDS-PAGE were blotted on PVDF membranes (Bio-Rad, Hercules, Calif.) and stained with Ponceau-S. Blotted proteins were sequenced using an ABI 470A protein sequencer with 120A PTH-AA analyzer.

TABLE 7

Strains and plasmids used in this example

| | Marker |
|---|---|
| Bacterial strain | |
| *E. coli* DH5α | F-Φ80dlacZΔM15Δ(lacZYA-argF)U169endA1 recA1hsdR17(r$_K$$^-$, m$_K$$^+$)deoRthi-1supE44λgyrA96relA1 |
| *S. typhimurium* SL1344 | wild type |
| VV114 | hil::kan-114 |
| VB122 | Kan$^R$, hilA::Kan-112 |
| EE637 | Tet$^R$, invF::lacZY11-5 |
| EE633 | Tet$^R$, sspA::lacZY4 |
| EE638 | Tet$^R$, sspC::lacZY11-6 |
| *S. typhimurium* (ATCC14028s) | wild type |
| CS451 | 14028sΔhil::Tn5-428 |
| CS022 | pho-24 (PhoP$^c$) |
| IB04 | prgH1::TnphoA |
| Plasmid | |
| pWSK29 | Amp$^R$ |
| pVV8-1 | Tet$^R$ |
| pVV71 | Amp$^R$ |
| pCH002 | Amp$^R$, sspCDA, hilA |
| pCH004 | Amp$^R$, sspC |
| pCH005 | Amp$^R$, sspCD |
| pCH006 | Amp$^R$, sspD |

Identification of *S. typhimurium* Mutants with Transposon Insertions in Genes Encoding Ssp To identify genes encoding Ssp, Tn5lacZY mutants of *S. typhimurium* SL1344 with transposon insertions located within the 40 kb "virulence island" (59–60 min. of the *S. typhimurium* chromosome) were analyzed for changed patterns in Ssp. An insertion in invF (invF::lacZY11-5), the first gene of the inv-spa operon, and a hilA::kan-122 insertion in VB122 led to major defects in the pattern of Ssp similar to a mutation in the prgHIJK operon (prgH1::TnphoA) which has implicated in *S. typhimurium* protein secretion (see Example 1). Specifically, all three mutants lack 5 major Ssp of 36, 38, 42, 63 and 87 kDa, while the hilA::kan-112 insertion leads to loss of some lower molecular weight protein bands in addition to these 5 Ssp (FIG. 8, lanes 4, 5, 6). Two other mutants exhibited detectable loss of only one and of three Ssp, respectively. The supernatants from the mutant strain EE633 containing the fusion lacZY4 were missing a protein of 87 kDa, while supernatants from the mutant strain EE638, containing fusion lacZY11-6, were missing protein species of 87, 42 and 36 kDa. In addition, supernatants from EE638 showed an increased abundance of a 63 kDa Ssp (FIG. 8, lanes 2, 3). Tn5lacZY in EE638 maps approximately 2.5 kb downstream from spaT while in EE633 the transposon maps 5.5 kb downstream from spaT as determined by Southern hybridization and PCR analyses. Both transposons were inserted in the same orientation (FIG. 9). A degenerate pool of oligonucleotides synthesized according to the sequence of the 12 amino-terminal amino acids of the 87 kDa protein (VTSVRTQPPVIM; SEQ ID NO: 27), hybridized specifically to a 5.5 kb BamHI fragment in pVV71 which comprises sequences between hilA and spaT (FIG. 9). These data indicate that the 87 kDa Ssp is encoded in the chromosomal region adjacent to the transposon insertions. Tn5lacZY in EE633 is likely to be directly within the gene encoding the 87 kDa Ssp, while Tn5lacZY in EE638 is likely to be inserted within one of the genes encoding the 42 and the 36 kDa sup having a polar effect on the synthesis of the other two Ssp missing in supernatants of this mutant.

Secretion of the 87 Ssp kDa Ssp is Dependent on prgHIJK

Since it was possible that the absence of the 87 kDa Ssp (Ssp87) in supernatants of EE633 and EE638 was due to impaired secretion rather than expression, whole cell lysates and supernatants of various strains were analyzed by immunoblotting with antiserum raised against partially purified Ssp87. FIG. 11 shows that Ssp87 of wild type *S. typhimurium* is found mainly in the supernatant, although some of the protein is detected in the cellular fraction (FIG. 11, lane 1). In contrast to wild type bacteria, all of the protein is found in the cellular fraction of the prgH1::TnphoA mutant IB040 (lane 3). Ssp87 could not be detected in the cellular fractions nor in supernatants of various invasion and secretion mutants: CS022 (PhoP$^C$), a mutant which constitutively represses PhoP regulated genes (Miller et al., *J. Bacteriol.* 172:2485–2490, 1990, hereby incorporated by reference) (lane 2), CS451 (Δhil::Tn5-428) carrying a 10 kb chromosomal deletion of the hil locus between 59 and 60 min. (lane 4), BE638 (lacZY11-6) (lane 5), and EE633 (lacZY4) (lane 6). The signal at 51 kDa in the supernatant fraction of wild type bacteria might represent a degradation product of ssp87, while the faint band at 34 kDa is likely nonspecific hybridization since it is present in all bacteria analyzed. These results demonstrate that lack of Ssp87 in supernatants of EZ633 and EE638 is due to impaired expression while lack of Ssp87 in supernatants of IB040 (prgH1::TnphoA) is caused by impaired secretion of the protein. These results further show that expression of the gene encoding Ssp87 is affected by the hil deletion ten and that expression of Ssp87, either directly or indirectly, is repressed by PhoP.

Strain EE638, But not EE633, is Markedly Deficient in Invasion

To determine the function of the 87, 42, and 36 kDa Ssp in invasion of epithelial cells, the ability of strain EZ638 and EE633 to invade HEp-2 cells was analyzed. EE638 showed more than a 100-fold reduction in invasiveness when compared to wild type bacteria, while EE633 exhibited invasion levels comparable to wild type bacteria (FIG. 9). These results suggested that the 36 and/or the 42 kDa Ssp but not the 87 kDa Ssp are required for epithelial cell invasion. In addition, observation of interactions between these mutants and PtK2 cells by time-lapse videomicroscopy indicated that the ability of EE638 to induce epithelial cell membrane ruffling is also markedly reduced, while ZE633 induced localized membrane ruffles at a frequency similar to wild type *S. typhimurium*.

The Tn5lacZY Insertions in EE638 and EE633 Define a Chromosomal Region Encoding Ssp *S. typhimurium* Homologues of the Shigella ipaBCDA Operon To determine the gene(s) affected by the transposon insertions in EE638 and EB633, part of a 11 kb EcoRI subclone of pVV8-1 was sequenced. Two complete and two partial open reading frames (ORFs), positioned in the same transcriptional direction, were identified (FIG. 9). The deduced gene products of the complete ORFs exhibit similarity to Shigella secreted proteins IpaC and IpaD (31% identity, 47% similarity; 37% identity, 56% similarity) respectively, and therefore were designated sspC and SspD (see FIG. 13 and FIG. 14). The gene products of the complete open reading frames were designated supC and SspD. The amino acid sequence derived from the 5'-end of sspC was identical to the amino-terminal sequence of the 42 kDa Ssp (underlined in FIG. 13). The deduced gene product of the partial ORF located immediately upstream from sspC shows 47% identity (67% similarity) to the carboxyterminal portion of *S. flexneri* secreted protein IpaB and was designated sspB (FIG. 12). The ORF starting immediately downstream of SspD was designated sapA. The amino acid sequence deduced from the 5' end of an ORF starting immediately downstream from sapD did not exhibit similarity to IpaA. However, DNA sequencing of internal parts of the gene predicted that the protein encoded by this gene, designated sspA, is similar to IpaA. Nevertheless, the sequence of amino acids 2–13 (underlined in FIG. 15) was identical to the amino-terminal sequence of the 87 kDa Ssp (see above). sspB, sspC, sapD, and sspA are separated by 27, 70, and 15 bp, respectively, and putative ribosome binding sites precede sspC, SspD, and sspA.

The amino acid similarities of Ssp to Ipas do not extend over the entire lengths of the proteins. The similarities between SspC/IpaC and SspD/IpaD are highest in the carboxy-terminal regions, while the central parts of SspB and IpaB are conserved (see FIGS. 12, 13, and 14). These similarities could reflect conservation in regions of the proteins required for secretion and/or invasion. Although both SspC and SspD appear to be secreted by the same mechanism, no obvious similarities or motifs common to these proteins were detected, thus implying conformational rather than sequential features in the get secretion of proteins by type III secretion pathways.

The precise insertion of Tn5lacZY in EE638 was determined by cloning and sequencing of a PCR product comprising the 5' region of the transposon and upstream chromosomal sequences and was shown to be located 189 bp downstream from the ATG start codon of sspC. The order of the ssp genes and the sap profile of EE638 indicate that the transposon insertion in sspC is polar on expression of SspD and sspA and that these genes are likely to be organized in a singly transcribed unit.

Both sspC and SspD are Necessary for *S. typhimurium* Invasion of Eithelial Cells A complementation analysis was carried out to determine the minimal fragment necessary for complementation of the epithelial cell invasion defect of EE638 (sspC::lacZY11-6) as well as for reconstitution of Ssp. All analyzed fragments were cloned downstream from the lac promoter in the 6–8 copies/chromosome vector pWSK29. As shown in FIG. 10, a 3.9 kb EcoRI-PvuII fragment comprising sspC and SspD in pCH005 was sufficient to complement the invasion defect of EE638 to wild type levels. When analyzed for Ssp, EE638 [pCH005] showed a pattern of Ssp similar to the wild type strain [pWSK29] except for the missing 87 kDa protein (SspA) (FIG. 16, lane 4). EE638 transformed with pCH002 carrying an 11 kb EcoRI fragment was partially complemented for invasion as well as for all 3 missing sup (FIG. 10 and FIG. 16, lane 6). In contrast, EE638 transformed with plasmids that contained either sspC or SspD alone (pCH004 and pCH006, respectively) were not complemented for invasion but showed reconstitution of the 42 kDa Ssp (SspC) or the 36 kDa Ssp (SspD), respectively (FIG. 10 and FIG. 16, lanes 3 and 5). In addition, the abundancy of a 63 kDa Ssp, which was found to be more abundant in supernatants of EE638, was reduced in supernatants of strains EE638 [pCH005], EE638 [pCH006], and EE638 [pCH002] and of SL1344 [pCH002]. These results demonstrate that both SspC and SspD are necessary for invasion of epithelial cells and indicate that SspC encodes the 42 kDa Ssp while the 36 kDa Ssp is likely to be encoded by SspD. In addition, complementation of the invasion defect of EE638 with pCH005 indicates that invasiveness is not influenced by the observed changes in the abundancy of the 63 kDa Ssp.

A Precipitate Found in *S. typhimurium* Culture Supernatants Contains Highly Abundant SspC and Other Proteins Supernatants from *S. typhimurium* wild type cultures contained a precipitate that, when solubilized in reducing SDS sample buffer, separates into at least four highly abundant protein bands of 63, 59, 42 and 22 kDa on SDS-PAGE (see FIG. 17, lane 1). Protein precipitates were also found in culture supernatants of EE638 and EE633, but not in supernatants of *S. typhimurium* mutants with global defects in protein secretion [CS022 (PhoP$^C$), IB040 (prgH1::TnphoA), CS451 (Δhil::Tn5-428) and VB122 (hilA::kan-112). *S. typhimurium* 14028s, the wild type parent of CS022 and IB040, showed the same protein pattern of precipitated material as SL1344]. The precipitate from EE633 cultures showed a similar composition to that of wild type precipitate by SDS-PAGE analysis. In contrast, a major protein band of 42 kDa was absent from the precipitate isolated from cultures of EE638 (FIG. 17, lane 2). Amino-terminal sequencing of this 42 kDa Ssp identified it as encoded by SspC. The identity of the amino-terminal protein sequence (MLISNVGINPAAYLN; SEQ ID NO: 28) with the amino acid sequence derived from the 5'-region of SspC (FIG. 13) shows that no amino-terminal processing of SspC occurs prior to its release into the supernatant.

SDS-PAGE analyses of precipitated material from culture supernatants of EE638 [pCH004 (SspC)] and EE638 [pCH005 (SspCD)] showed a pattern similar to wild type [pWSK29] material (FIG. 17, lane 3 and 4), confirming that the respective plasmids complemented the mutant for secretion of SspC. Protein patterns of soluble Ssp and precipitates isolated from untransformed cultures of SL1344 or EE638 were identical to those shown in FIGS. 16, 17, lane 1 and 2, respectively. Precipitate of EE638 [pCH006 (SspD) ] was found to be similar to precipitate from EE638 [pWSK29] except for reduced abundancy of a 63 kDa protein band (FIG. 17, lane 5). The precipitate from EE638 [pCH002 (SspCDA)] contained an additional major protein band of approximately 51 kDa, which was also present in precipitate from SL1344 [pCH002] (FIG. 17, lanes 6, 7). Comparison of precipitated proteins to soluble Ssp on SDS-PAGE (FIG. 17, lanes 8, 9) showed that SspC in the precipitate has the same electrophoretic mobility as the 42 kDa soluble Ssp. These data suggest that the 42 kDa soluble Ssp is identical to precipitated SspC.

SspC and SspA are secreted proteins of 42 and 87 kDa, as demonstrated by amino-terminal sequencing and by complementation analyses. It is further likely that the 36 kDa protein encoded by SspD is secreted, since lack of a 36 kDa Ssp in supernatants of ZE638 (lacZY11-6) was complemented by transformation of this mutant with plasmids containing SspD. The 63 kDa Ssp is the protein likely to be encoded by SspB.

SspA, SspB, SspC, and SspD appear to be targets of the inv-spa-prgHIJK encoded secretion apparatus, since these Ssp are missing in supernatants of mutants affecting expression or regulation of inv-spa and prgHIJK (FIG. 8). Typical for proteins secreted by type III secretion pathways, no amino-terminal processing of SspA and SspC was observed. The dependency of Ssp secretion on prgHIJK was further proven by demonstrating that SspA is abundantly secreted by wild type cells, while it is completely retained in the cellular fraction of the prgH1::TnphoA mutant IB040 (FIG. 11). The 38 kDa Ssp of the five major Ssp dependent on the inv-spa-prgHIJK secretion apparatus may be the product of the invJ invasion locus.

The immunoblot analysis of SspA secretion suggests that expression of the gene encoding SspA is negatively controlled by the virulence two component regulatory system PhoP/PhoQ. PhoP/Q has a global effect on protein secretion which is partially due to negative transcriptional regulation of prgHIJK (see Example 1).

The SspBCDA genes are located between the large inv-spa gene cluster and prgHIJK at 59 minutes on the *S. typhimurium* chromosome. FIG. 18 shows the relative positions of the invasion genes in *S. typhimurium* in comparison to their *S. flexneri* homologues, which are clustered in a 31 kb region of a large virulence plasmid. The invasion genes cluster in three groups (inv-spa/mxi-spa, Ssp/ipa, and prgIJK/mxiHIJ) which exhibit conserved gene structure and organization, suggesting that these genes were acquired by horizontal gene transfer. Acquisition by horizontal gene transfer is further supported by the fact that these *S. typhimurium* invasion genes are within a 40 kb "virulence island" which, despite the otherwise high overall genetic similarity between *S. typhimurium* and *E. coli* K-12, is unique to *S. typhimurium*. However, the three invasion gene clusters from *S. flexneri* and *S. typhimurium* are in different relative positions to each other and are interspersed between non-homologous genes, thus implying multi-recombinational events in the evolution of these genetic regions.

In addition to soluble Ssp the supernatants of *S. typhimurium* cultures contained a flocculent precipitate consisting of SspC and three other major protein species of 63 (Ssp 63), 59 (Ssp 59), and 22 (Ssp 22) kDa. The combination and abundancy of Ssp in the precipitate from *S. typhimurium* cultures is strikingly different from that in the soluble fraction (see FIG. 17). Though Ssp, including SspC, are found in both the precipitate and the soluble fraction, SspD, even when overproduced, was not detected in the precipitate. This emphasizes the difference in composition of precipitate and soluble fraction and supports the possibility of specific protein-protein interactions between the four Ssp leading to precipitate formation.

OTHER EMBODIMENTS

Using reagents derived from partial cDNA clones of an Ssp, e.g., SspA, the isolation of a full-length cDNA encoding the Ssp is well within the skill of those skilled in the art of molecular biology. For example, a radiolabelled probe made from a known partial cDNA sequence can be used to identify and isolate from a library of recombinant plasmids cDNAs that contain regions with identical to the previously isolated cDNAs. The screening of cDNA libraries with radiolabelled cDNA probes is routine in the art of molecular biology (see Sambrook et al., 1989, *Molecular Cloning: a Laboratory Manual*, second edition., Cold Spring Harbor Press, Cold Spring Harbor, N.Y). The cDNA can be isolated and subcloned into a plasmid vector, and the plasmid DNA purified by standard techniques. The cDNA insert is sequenced using the dideoxy chain termination method well known in the art (Sambrook et al, supra). Oligonucleotide primers corresponding to bordering vector regions as well as primers prepared from previously isolated cDNA clones can be employed to progressively determine the sequence of the entire gene.

Similar methods can be used to isolate Ssp which are related to SspA, SspB, SspC, or SspD. To isolate related Ssp, a probe having a sequence derived from (or identical to) all or a portion of SspA, SspB, SspC, or SspD can be used to screen a library of Salmonella DNA (or cDNA). DNA encoding a related Ssp will generally hybridize at greater stringincy than DNA encoding other proteins. This approach can be used to identify *Salmonella typhimurium* Ssp as well as Ssp of other Salmonella.

Generation of Monoclonal Antibodies:

Monoclonal antibodies can be generated to purified native or recombinant gene products, e.g., Ssp, by standard procedures, e.g., those described in Coligan et al., eds., *Current Protocols in Immunology*, 1992, Greene Publishing Associates and Wiley-Interscience). To generate monoclonal antibodies, a mouse is immunized with the recombinant protein, and antibody-secreting B cells isolated and immortalized with a non-secretory myeloma cell fusion partner. Hybridomas are then screened for production of specific antibodies and cloned to obtain a homogenous cell population which produces a monoclonal antibody. For example, hybridomas secreting the desired antibodies can be screened by ELISA. Specificities of the monoclonal antibodies can be determined by the use of different protein or peptide antigens in the ELISA. Useful quantities of antibodies can be produced by either the generation of ascites fluid in mice or by large scale in vitro culture of the cloned antibody-producing hybridoma cell line. Antibodies can be purified by various chromatographic procedures known in the art, such as affinity chromatography on either immobilized Protein A or Protein G.

The invention also includes DNA encoding other Ssp (e.g., Ssp 54, Ssp 42, and Ssp 22) found in cell supernatants. Those skilled in the art can readily clone the corresponding genes based on the amino terminal sequence or the corresponding protein. The amino terminal sequence of Ssp54 is MNNLTLSXFXKVG (SEQ ID NO: 29). The amino terminal sequence of Ssp42 is MLISNVGINPAAYLN (SEQ ID NO: 30). The amino terminal sequence of Ssp 22 is TKITL-SPQNFFI (SEQ ID NO: 31).

What is claimed is:

1. An isolated and purified nucleic acid molecule that is free of the nucleic acid sequences that flank the nucleic acid molecule in the naturally-occurring genome of the organism from which the nucleic acid molecule is derived comprising a nucleotide sequence encoding a polypeptide comprising the amino acid sequence of SEQ ID NO:5.

2. The isolated and purified nucleic acid molecule of claim 1 comprising the nucleotide sequence of SEQ ID NO: 1.

3. An isolated and purified nucleic acid molecule that is free of the nucleic acid sequences that flank the nucleic acid molecule in the naturally-occurring genome of the organism from which the nucleic acid molecule is derived, and that hybridizes under conditions of hybridization in 50% formamide at 42° C. and washing in 0.1×SSC at 65° C. to a nucleic acid molecule consisting of the nucleotide sequence of SEQ ID NO:1, and wherein the isolated and purified nucleic acid molecule is at least 50 nucleotides in length.

4. A vector comprising the isolated and purified nucleic acid molecule of any of claims 3, 1, or 2.

5. A host cell comprising the isolated and purified nucleic acid molecule of any of claims 3, 1, or 2.

6. A host cell comprising the vector of claim 4.

7. An isolated and purified nucleic acid molecule that is free of the nucleic acid sequences that flank the nucleic acid molecule in the naturally-occurring genome of the organism from which the nucleic acid molecule is derived comprising a nucleotide sequence encoding a polypeptide comprising the amino acid sequence of SEQ ID NO:6.

8. An isolated and purified nucleic acid molecule that is free of the nucleic acid sequences that flank the nucleic acid molecule in the naturally-occurring genome of the organism from which the nucleic acid molecule is derived comprising the nucleotide sequence of SEQ ID NO: 2.

9. An isolated and purified nucleic acid molecule that is free of the nucleic acid sequences that flank the nucleic acid molecule in the naturally-occurring genome of the organism from which the nucleic acid molecule is derived, and that hybridizes under conditions of hybridization in 50% formamide at 42° C. and washing in 0.1×SSC at 65° C. to a nucleic acid molecule consisting of the nucleotide sequence of SEQ ID NO:2, and wherein the isolated and purified nucleic acid molecule is at least 50 nucleotides in length.

10. A vector comprising the isolated and purified nucleic acid molecule of any of claims 9, 7, or 8.

11. A host cell comprising the isolated and purified nucleic acid molecule of any of claims 9, 7, or 8.

12. A host cell comprising the vector of claim 10.

13. An isolated and purified nucleic acid molecule that is free of the nucleic acid sequences that flank the nucleic acid molecule in the naturally-occurring genome of the organism from which the nucleic acid molecule is derived comprising a nucleotide sequence encoding a polypeptide comprising the amino acid sequence of SEQ ID NO:7.

14. An isolated and purified nucleic acid molecule that is free of the nucleic acid sequences that flank the nucleic acid molecule in the naturally-occurring genome of the organism from which the nucleic acid molecule is derived comprising the nucleotide sequence of SEQ ID NO: 3.

15. An isolated and purified nucleic acid molecule that is free of the nucleic acid sequences that flank the nucleic acid molecule in the naturally-occurring genome of the organism from which the nucleic acid molecule is derived, and that hybridizes under conditions of hybridization in 50% formamide at 42° C. and washing in 0.1×SSC at 65° C. to a nucleic acid molecule consisting of the nucleotide sequence of SEQ ID NO:3, and wherein the isolated and purified nucleic acid molecule is at least 50 nucleotides in length.

16. A vector comprising the isolated and purified nucleic acid molecule of any of claims 15, 13, or 14.

17. A host cell comprising the isolated and purified nucleic acid molecule of any of claims 15, 13, or 14.

18. A host cell comprising the vector of claim 16.

19. An isolated and purified nucleic acid molecule that is free of the nucleic acid sequences that flank the nucleic acid molecule in the naturally-occurring genome of the organism from which the nucleic acid molecule is derived comprising a nucleotide sequence encoding a polypeptide comprising the amino acid sequence of SEQ ID NO:8.

20. The isolated and purified nucleic acid molecule of claim 19 comprising the nucleotide sequence of SEQ ID NO:4.

21. An isolated and purified nucleic acid molecule that is free of the nucleic acid sequences that flank the nucleic acid molecule in the naturally-occurring genome of the organism from which the nucleic acid molecule is derived, and that hybridizes under conditions of hybridization in 50% formamide at 42° C. and washing in 0.1×SSC at 65° C. to a nucleic acid molecule consisting of the nucleotide sequence of SEQ ID NO:4, and wherein the isolated and purified nucleic acid molecule is at least 50 nucleotides in length.

22. A vector comprising the isolated and purified nucleic acid molecule of any of claims 21, 19, or 20.

23. A host cell comprising the isolated and purified nucleic acid molecule of any of claims 21, 19, or 20.

24. A host cell comprising the vector of claim 22.

25. An isolated and purified nucleic acid molecule that is free of the nucleic acid sequences that flank the nucleic acid molecule in the naturally-occurring genome of the organism from which the nucleic acid molecule is derived comprising a nucleotide sequence encoding a polypeptide comprising the amino acid sequence of SEQ ID NO:14.

26. An isolated and purified nucleic acid molecule that is free of the nucleic acid sequences that flank the nucleic acid molecule in the naturally-occurring genome of the organism from which the nucleic acid molecule is derived comprising the nucleotide sequence of SEQ ID NO: 13.

27. An isolated and purified nucleic acid molecule that is free of the nucleic acid sequences that flank the nucleic acid molecule in the naturally-occurring genome of the organism from which the nucleic acid molecule is derived, and that hybridizes under conditions of hybridization in 50% formamide at 42° C. and washing in 0.1×SSC at 65° C. to a nucleic acid molecule consisting of the nucleotide sequence of SEQ ID NO:13, and wherein the isolated and purified nucleic acid molecule is at least 50 nucleotides in length.

28. A vector comprising the isolated and purified nucleic acid molecule of any of claims 27, 25, or 26.

29. A host cell comprising the isolated and purified nucleic acid molecule of any of claims 27, 25, or 26.

30. A host cell comprising the vector of claim 28.

31. An isolated and purified nucleic acid molecule that is free of the nucleic acid sequences that flank the nucleic acid molecule in the naturally-occurring genome of the organism from which the nucleic acid molecule is derived comprising a nucleotide sequence encoding a polypeptide comprising the amino acid sequence of SEQ ID NO: 12.

32. The isolated and purified nucleic acid molecule of claim 31 comprising the nucleotide sequence of SEQ ID NO: 10.

33. An isolated and purified nucleic acid molecule that is free of the nucleic acid sequences that flank the nucleic acid molecule in the naturally-occurring genome of the organism from which the nucleic acid molecule is derived, and that hybridizes under conditions of hybridization in 50% formamide at 42° C. and washing in 0.1×SSC at 65° C. to a nucleic acid molecule consisting of the nucleotide sequence of SEQ ID NO:10, and wherein the isolated and purified nucleic acid molecule is at least 50 nucleotides in length.

34. A vector comprising the isolated and purified nucleic acid molecule of any of claims 33, 31, or 32.

35. A host cell comprising the isolated and purified nucleic acid molecule of any of claims 33, 31, or 32.

36. A host cell comprising the vector of claim 34.

37. An isolated and purified nucleic acid molecule that is free of the nucleic acid sequences that flank the nucleic acid molecule in the naturally-occurring genome of the organism from which the nucleic acid molecule is derived comprising the nucleotide sequence of SEQ ID NO: 15.

38. An isolated and purified nucleic acid molecule that is free of the nucleic acid sequences that flank the nucleic acid molecule in the naturally-occurring genome of the organism from which the nucleic acid molecule is derived, and that hybridizes under conditions of hybridization in 50% formamide at 42° C. and washing in 0.1×SSC at 65° C. to a nucleic acid molecule consisting of the nucleotide sequence of SEQ ID NO:15, and wherein the isolated and purified nucleic acid molecule is at least 50 nucleotides in length.

39. A vector comprising the isolated and purified nucleic acid molecule of any of claims 38 or 37.

40. A host cell comprising the isolated and purified nucleic acid molecule of any of claims 38 or 37.

41. A host cell comprising the vector of claim 39.

42. An isolated and purified nucleic acid consisting of SEQ ID NO:1.

43. The isolated and purified nucleic acid molecule of claim 9 or claim 7, wherein the polypeptide encoded by the nucleic acid molecule, can induce bacterial-mediated endocytosis (BME) when introduced into a bacterium that lacks a wild type SspC polypeptide.

44. The isolated and purified nucleic acid molecule of claim 15 or claim 13, wherein the polypeptide encoded by the nucleic acid molecule can induce bacterial-mediated endocytosis (BME) when introduced into a bacterium that lacks a wild type SspD polypeptide.

45. An isolated and purified nucleic acid molecule consisting of SEQ ID NO:4.

46. The isolated and purified nucleic acid molecule of claim 21 or 19, wherein the polypeptide encoded by the nucleic acid molecule can induce bacterial-mediated endocytosis (BME).

47. An isolated and purified nucleic acid molecule consisting of SEQ ID NO:10.

48. An isolated and purified nucleic acid molecule consisting of SEQ ID NO:2.

49. An isolated and purified nucleic acid molecule consisting of SEQ ID NO:3.

50. An isolated and purified nucleic acid molecule consisting of SEQ ID NO:13.

51. A method of inducing uptake of a bacterial cell by an epithelial cell in a mammal, comprising increasing expression of the nucleic acid molecule of claim 3 or 9 in said bacterial cell and administering said bacterial cell to said mammal.

52. The method of claim 51, wherein said bacterial cell is a Salmonella cell.

* * * * *

UNITED STATES PATENT AND TRADEMARK OFFICE
CERTIFICATE OF CORRECTION

PATENT NO. : 6,861,247 B1
DATED : March 1, 2005
INVENTOR(S) : Miller

It is certified that error appears in the above-identified patent and that said Letters Patent is hereby corrected as shown below:

<u>Title page,</u>
Item [21], Application No., insert -- Appl. Filed May 14, 1998 --.
Item [56], References Cited, OTHER PUBLICATIONS,
"Harris et al. J. of" reference, delete "he", insert -- the --.
"Ank" should read -- Ahn --.
"Collazo et al." reference, delete "identication" and insert -- identification --.
Delete the following references, they are duplicates, "Hermant", "Kaniga" and "Pegues."

<u>Column 1,</u>
Line 7, delete "tqi".

<u>Column 2,</u>
Line 46, insert a space after "amino".
Line 56, delete "An", insert -- an --.
Line 56, delete the space between "Ssp" and "B".

<u>Column 3,</u>
Line 59, delete "sap", insert -- Ssp --.
Line 65, delete "an", insert -- a --.

<u>Column 4,</u>
Line 15, delete "feature", insert -- features --.
Line 16, delete "gene", insert -- genes --.
Line 29, delete "cholorao", insert -- cholerae --.
Line 37, delete "psratyphi", (first occurrence), insert -- paratyphi --.
Line 47, delete "or", insert -- of --.

<u>Column 5,</u>
Line 9, delete "apropriate", insert -- appropriate --.
Line 63, insert -- 35 -- before "amino".

<u>Column 6,</u>
Line 3, delete "university", insert -- University --.
Line 4, delete "biotechnology center", insert -- Biotechnology Center --.
Line 4, delete "university avenue", insert -- University Avenue --.
Line 7, delete "substitutions".
Line 56, delete "the" (first occurrence).

UNITED STATES PATENT AND TRADEMARK OFFICE
CERTIFICATE OF CORRECTION

PATENT NO. : 6,861,247 B1
DATED : March 1, 2005
INVENTOR(S) : Miller

It is certified that error appears in the above-identified patent and that said Letters Patent is hereby corrected as shown below:

Column 6 (cont'd),
Line 63, delete "and".

Column 7,
Line 19, delete "Represents", insert -- represents --.
Line 47, delete "140289", insert -- 140285 --.

Column 8,
Line 1, delete "Δhil", insert -- $_\Delta$hil --.
Line 22, delete "lacSY11-5", insert -- lacZY11-5 --.
Line 48, delete "A" before "indicates", insert -- $_\Delta$ --.

Column 9,
Line 28, delete "(5spCD)", insert -- (sspCD) --.
Line 29, delete "(SspD)", insert -- (sspD) --.
Line 42, delete "lxi", before "spa", insert -- mxi --.
Line 65, delete "prgH", insert -- sspH --.

Column 10,
Line 46, insert -- as -- after "used".
Line 57, insert -- of -- after "presence".

Column 11,
Line 57, delete "A", insert -- an --.
Line 62, delete "ii" after "protein", insert -- is --.

Column 12,
Line 38, delete "by" after "then", insert -- be --.

Column 13,
Line 16, delete "(stpA)", insert -- (StpA) --.
Line 29, insert -- to -- after "useful".
Line 58, insert -- : -- after "Genes".

Column 14,
Line 20, insert -- , -- after "Strains".
Line 34, delete "DATP", insert -- dATP --.
Line 61, delete "a" before "841-bp", insert -- an --.

UNITED STATES PATENT AND TRADEMARK OFFICE
CERTIFICATE OF CORRECTION

PATENT NO. : 6,861,247 B1  Page 3 of 4
DATED : March 1, 2005
INVENTOR(S) : Miller It is certified that error appears in the above-identified patent and that said Letters Patent is hereby corrected as shown below:

<u>Column 14 (cont'd),</u>
Line 66, delete "(51", insert -- (5' --.

<u>Column 15,</u>
Line 1, delete "31)", insert -- 3') --.
Line 8, delete "51", insert -- (5' --.
Line 20, delete "N", after "8", insert -- M --.
Line 42, insert a space between "system" and "or".

<u>Column 16,</u>
Line 38, delete "Eschericnia", insert -- Escherichia --.
Line 47, delete "140288", insert -- 14028s --.
Line 57, delete "pWXSH5", insert -- pWKSH5 --.

<u>Column 17,</u>
Line 43, delete "a" before "2600".
Line 67, delete "31)", insert -- 3') --.

<u>Column 19,</u>
Line 23, delete "PACE", insert -- PAGE --.

<u>Column 20,</u>
Line 28, delete the space between "orfI" and the period.
Line 44, delete "TnpboA", insert -- TnphoA --.

<u>Column 22,</u>
Line 27, delete "SspD", insert -- sspD --.
Line 30, delete "Ipac", insert -- IpaC --.

<u>Column 23,</u>
Line 61, delete "2x108", insert -- $2x10^8$ --.

<u>Column 24,</u>
Line 62, delete "sup", insert -- ssp --.

<u>Column 25,</u>
Line 16, delete "BE638", insert -- EE638 --.
Line 19, delete "ssp87", insert -- Ssp87 --.

UNITED STATES PATENT AND TRADEMARK OFFICE
CERTIFICATE OF CORRECTION

PATENT NO.   : 6,861,247 B1
DATED        : March 1, 2005
INVENTOR(S)  : Miller

It is certified that error appears in the above-identified patent and that said Letters Patent is hereby corrected as shown below:

Column 25 (cont'd),
Line 22, delete "EZ633", insert -- EE633 --.
Line 26, delete "ten" after "deletion".
Line 31, delete "EZ638", insert -- EE638 --.
Line 41, delete "ZE633", insert -- EE633 --.
Line 48, delete "EB633", insert -- EE633 --.
Line 48, delete "a" before "11", insert -- an --.
Lines 55, 58 and 65, delete "SspD", insert -- sspD --.
Line 57, delete "supC", insert -- sspC --.
Line 65, delete "sapA", insert -- sspA --.
Line 67, delete "sapD", insert -- sspD --.

Column 26,
Line 6, delete "sapD", insert -- sspD --.
Lines 8, 27, 30, 38 and 47, delete "SspD", insert -- sspD --.
Line 19, delete "get".
Line 26, delete "sap", insert -- Ssp --.
Line 27, delete "SspD", insert -- sspD --.
Line 31, delete "Eithelial", insert -- Epithelial --.
Line 45, delete "sup", insert -- ssp --.

Column 27,
Line 5, delete "(prgHI::", insert -- (prqH:: --.
Line 26, delete "lane", insert -- lanes --.
Line 43, delete "ZE638", insert -- EE638 --.

Signed and Sealed this

Eleventh Day of April, 2006

JON W. DUDAS
*Director of the United States Patent and Trademark Office*